US008551781B2

(12) United States Patent
Rome et al.

(10) Patent No.: US 8,551,781 B2

(45) Date of Patent: Oct. 8, 2013

(54) VAULT COMPLEXES FOR FACILITATING BIOMOLECULE DELIVERY

(75) Inventors: Leonard H. Rome, Tarzana, CA (US); Valerie A. Kickhoefer, Sherman Oaks, CA (US); Glen R. Nemerow, La Jolla, CA (US); Cheng-Yu Lai, La Jolla, CA (US); Christopher M. Wiethoff, Downers Grove, IL (US); Mu Ri Han, Los Angeles, CA (US)

(73) Assignees: The Regents of the University of California, Oakland, CA (US); The Scripps Research Institute, La Jolla, CA (US)

( * ) Notice: Subject to any disclaimer, the term of this patent is extended or adjusted under 35 U.S.C. 154(b) by 0 days.

(21) Appl. No.: 12/950,994

(22) Filed: Nov. 19, 2010

(65) Prior Publication Data

US 2011/0201112 A1 Aug. 18, 2011

Related U.S. Application Data

(60) Provisional application No. 61/262,667, filed on Nov. 19, 2009, provisional application No. 61/291,081, filed on Dec. 30, 2009.

(51) Int. Cl.
*C12N 5/00* (2006.01)
*C12N 5/07* (2010.01)

(52) U.S. Cl.
USPC .......................................... 435/375; 530/350

(58) Field of Classification Search
USPC .......................................... 435/375; 530/350
See application file for complete search history.

(56) References Cited

PUBLICATIONS

Lai et al. (Vault Nanoparticles Containing an Adenovirus-Derived Membrane Lytic Protein Facilitate Toxin and Gene Transfer. ACS Nano. 2009 3(3): 691-699).*

Allen, T.M. et al., "Drug Delivery Systems: Entering the Mainstream," Science, 2004, pp. 1818-1822, vol. 303.

Barbiei, L. et al., "Ribosome-Inactivating Proteins from Plants," Biochima et Biophysica Acta, 1993, pp. 237-282, vol. 1154.

Berger, W. et al., "Vaults and the Major Vault Protein: Novel Roles in Signal Pathway Regulation and Immunity," Cell. Mol. Life Sci. 2009, pp. 43-61, vol. 66, No. 1.

Blumenthal, R. et al., "pH Dependent Lysis of Liposomes by Adenovirus," Biochemistry, 1986, pp. 2231-2237, vol. 25.

Champion, C.L. et al., "A Vault Nanoparticle Vaccine Induces Protective Mucosal Immunity," PLoS One, Apr. 2009, e5409, 12 pages, vol. 4, No. 4.

Esfandiary, R. et al., "Structural Stability of Vault Particles," Journal of Pharmaceutical Sciences, 2008, pp. 1376-1386, vol. 98, No. 4.

Goldsmith, L. E. et al., "Vault Nanocapsule Dissociation into Halves Triggered at Low pH," Biochemistry, 2007, pp. 2865-2875, vol. 46.

Goodman, R. M. et al., "Assembly of Flexuous Plant Viruses and Their Proteins," Philosophical Transactions of the Royal Society of London, 1976, pp. 173-179, vol. 276.

Griesh, K., "Enhanced Permeability and Retention of Macromolecular Drugs in Solid Tumors: A Royal Gate for Targeted Anticancer Nanomedicines," Journal of Drug Targeting, Aug.-Sep. 2007, pp. 457-464, vol. 15, No. 7-8.

Haidar, M. A., "Tobacco Rattle Virus RNA-Protein Interactions" Philosophical Transactions of the Royal Society of London, 1976, pp. 165-172, vol. 276.

Hed, J. et al., "The Use of Fluorescence Quenching in Flow Cytofluorometry to Measure the Attachment and Ingestion Phases in Phagocytosis in Peripheral Blood Without Prior Cell Separation," Journal of Immunological Methods, 1987, pp. 119-125, vol. 101.

Izquierdo, M.A. et al., "Broad Distribution of the Multidrug Resistance-Related Vault Lung Resistance Protein in Normal Human Tissues and Tumors," American Journal of Pathology, Mar. 1996, pp. 877-887, vol. 148, No. 3.

Kaddis, C. S., et al. "Sizing Large Proteins and Protein Complexes by Electrospray Ionization Mass Spectrometry and Ion Mobility," J. Am. Soc. Mass. Spectrom, 2007, pp. 1206-1216, vol. 18.

Kedersha, N.L. et al., "Isolation and Characterization of a Novel Ribonucleoprotein Particle: Large Structures Contain a Single Species of Small RNA," The Journal of Cell Biology, Sep. 1986, pp. 699-709, vol. 103, No. 3.

Kedersha, N.L. et al., "Vaults. III. Vault Ribonucleoprotein Particles Open into Flower-Like Structures with Octagonal Symmetry," The Journal of Cell Biology, Jan. 1991, pp. 225-235, vol. 112, No. 2.

Kickhoefer, V.A. et al., "Engineering of Vault Nanocapsules with Enzymatic and Fluorescent Properties," Proc. Natl. Acad. Sci. USA, Mar. 22, 2005, pp. 4348-4352, vol. 102, No. 12.

Kickhoefer, V. A. et al., "Targeting Vault Nanoparticles to Specific Cell Surface Receptors," ACS Nano, 2009, pp. 27-36, vol. 3, No. 1.

Kingdon, G. C. et al. "Effects of Listeria Monocytogenes Hemolysin on Phagocytic Cells and Lysosomes," Infection and Immunity, 1970, pp. 356-362, vol. 1, No. 4.

Kong, L.B. et al., "Structure of the Vault, a Ubiquitous Cellular Component," Structure, Mar. 24, 1999, pp. 371-379, vol. 7, No. 4.

Lai, C. Y. et al., "Vault Nanoparticles Containing an Adenovirus-Derived Membrane Lytic Protein Facilitate Toxin and Gene Transfer," ACS Nano, Feb. 18, 2009, pp. 691-699, vol. 3, No. 3.

Lee, J. H. et al., "Delivery of an Adenovirus Vector in a Calcium Phosphate Coprecipitate Enhances the Therapeutic Index of Gene Transfer to Airway Epithelia," Human Gene Therapy, Mar. 1, 1999, pp. 603-613, vol. 10.

Maeda, H. et al., "Tumor Vascular Permeability and the EPR Effect in Macromolecular Therapeutics: A Review," Journal of Controlled Release, 2000, pp. 271-284, vol. 65.

Mikyas, Y. et al., "Cryoelectron Microscopy Imaging of Recombinant and Tissue Derived Vaults: Localization of the MVP N Termini and VPARP," J. Mol. Biol., 2004, pp. 91-105, vol. 344, No. 1.

Poderycki, M.J. et al., "The p80 Homology Region of TEP1 is Sufficient for Its Association with the Telomerase and Vault RNAs, and the Vault Particle," Nucleic Acids Research, 2005, pp. 893-902, vol. 33, No. 3.

(Continued)

*Primary Examiner* — Karen Cochrane Carlson
*Assistant Examiner* — Natalie Moss
(74) *Attorney, Agent, or Firm* — Fenwick & West LLP

(57) ABSTRACT

The invention relates to compositions of vault complexes containing recombinant membrane lytic proteins, such as an adenovirus protein VI lytic domain, and methods of using the vault complexes to facilitate delivery and entry of a biomolecule into a cell or subject.

3 Claims, 17 Drawing Sheets

(56) References Cited

PUBLICATIONS

Poderycki, M. J., et al. "The Vault Exterior Shell is a Dynamic Structure That Allows Incorporation of Vault-Associated Proteins Iinto Its Interior," Biochemistry, 2006, pp. 12184-12193, vol. 45.
Seiler, M. P., et al. "Dendritic Cell Function After Gene Transfer with Adenovirus-Calcium Phosphate Co-precipitates," Molecular Therapy, Feb. 2007, pp. 386-392, vol. 15, No. 2.
Shaughnessy, L. M. et al. "Membrane Perforations Inhibit Lysosome Fusion by Altering pH and Calcium in *Listeria Monocytogenes* Vacuoles," Cellular Microbiology, 2006, pp. 81-92, vol. 8, No. 5.
Stephen, A.G. et al., "Assembly of Vault-like Particles in Insect Cells Expressing Only the Major Vault Protein," The Journal of Biological Chemistry, Jun. 29, 2001, pp. 23217-23220, vol. 276, No. 26.
Suprenant, K.A., "Vault Ribonucleoprotein Particles: Sarcophagi, Gondolas, or Safety Deposit Boxes?" Biochemistry, Dec. 10, 2002, pp. 14447-14454, vol. 41, No. 49.
Toyoda, K. et al., "Calcium Phosphate Precipitates Augment Adenovirus-Mediated Gene Transfer to Blood Vessels in Vitro and in Vivo," Gene Therapy, 2000, pp. 1284-1291, vol. 7.
Walters, R. et al., "Mechanism by Which Calcium Phosphate Coprecipitation Enhances Adenovirus-Mediated Gene Transfer," Gene Therapy, 1999, pp. 1845-1850, vol. 6.
Wells, A., "EGF Receptor," The International Journal of Biochemistry & Cell Biology, 1999, pp. 637-643, vol. 31, No. 6.
Weyergang, A. et al., "Photochemically Stimulated Drug Delivery Increases the Cytotoxicity and Specificity of EGF-Saporin," Journal of Controlled Release, 2006, pp. 165-173, vol. 111.
Wiethoff, C. M. et al., "Adenovirus Protein VI Mediates Membrane Disruption Following Capsid Disassembly," Journal of Virology, Feb. 2005, pp. 1992-2000, vol. 79, No. 4.
Xie, H. et al., "EGF receptor regulation of cell motility: EGF induces disassembly of focal adhesions independently of the motility-associated PLCgamma signaling pathway," J Cell Sci, 1998, 111 (Pt 5),615-24.
Yip, W. L. et al., "Targeted Delivery and Enhanced Cytotoxicity of Cetuximab-Saporin by Photochemical Internalization in EGFR-Positive Cancer Cells," Molecular Pharmaceutics, 2007, pp. 241-251, vol. 4.

* cited by examiner

A
cells
CaPi
CP-MVP
Lipofect-amine 2000
2
4
5
10
25
50
100
250
pVI-MVP Vaults (×10⁵) / cell
B
Lipofectamine 2000
cp-MVP
pVI-MVP
C
cells
CaPi 2µg
CaPi 10µg
CaPi 10µg + cpMVP
pDNA 10µg + Lipofect-amine 2000
CaPi 2µg + pVIMVP
CaPi 6µg + pVIMVP
CaPi 10µg + pVIMVP

VAULT COMPLEXES FOR FACILITATING BIOMOLECULE DELIVERY

CROSS REFERENCE TO RELATED APPLICATIONS

This application claims the benefit of U.S. Provisional Application No. 61/262,667, filed Nov. 19, 2009, and U.S. Provisional Application No. 61/291,081, filed Dec. 30, 2009, the entire disclosures of which are hereby incorporated by reference in their entirety for all purposes.

SEQUENCE LISTING

The instant application contains a Sequence Listing which has been submitted in ASCII format via EFS-Web and is hereby incorporated by reference in its entirety. Said ASCII copy, created on Jan. 3, 2011, is named 17591US CRF sequencelisting.txt and is 129,404 bytes in size.

STATEMENT REGARDING FEDERALLY SPONSORED RESEARCH OR DEVELOPMENT

This invention was made with Government support under Grant No. 0210690, awarded by the National Science Foundation and Grant Nos. EB004553 and HL054352, awarded by the National Institutes of Health. The Government has certain rights in this invention.

BACKGROUND OF THE INVENTION

1. Field of the Invention

The present invention relates generally to non-viral compositions and methods useful for the cellular delivery of one or more molecules of interest. In various embodiments, modified recombinant vault particles are described which comprise a peptide domain that enhances the permeability of the particles across the cell membranes of cells targeted for delivery. Also included in the invention is the use of the compositions as cellular delivery agents for selected molecules of interest, such as nucleic acid.

2. Description of the Related Art

Vaults are cytoplasmic ubiquitous ribonucleoprotein particles first described in 1986 that are found in all eukaryotic cells [1]. Native vaults are 12.9±1 MDa ovoid spheres with overall dimensions of approximately 40 nm in width and 70 nm in length [2,3], present in nearly all-eukaryotic organisms with between $10^4$ and $10^7$ particles per cell [4]. Despite their cellular abundance, vault function remains elusive although they have been linked to many cellular processes, including the innate immune response, multidrug resistance in cancer cells, multifaceted signaling pathways, and intracellular transport [5].

Vaults are highly stable structures in vitro, and a number of studies indicate that the particles are non-immunogenic [6]. Vaults can be engineered and expressed using a baculovirus expression system and heterologous proteins can be encapsulated inside of these recombinant particles using a protein-targeting domain termed INT for vault INTeraction. Several heterologous proteins have been fused to the INT domain (e.g. fluorescent and enzymatic proteins) and these fusion proteins are expressed in the recombinant vaults and retain their native characteristics, thus conferring new properties onto these vaults [7,8].

Vaults are generally described in U.S. Pat. No. 7,482,319, filed on Mar. 10, 2004; U.S. application Ser. No. 12/252,200, filed on Oct. 15, 2008; International Application No. PCT/US2004/007434, filed on Mar. 10, 2004; U.S. Provisional Application No. 60/453,800, filed on Mar. 20, 2003; U.S. Pat. No. 6,156,879, filed on Jun. 3, 1998; U.S. Pat. No. 6,555,347, filed on Jun. 28, 2000; U.S. Pat. No. 6,110,740, filed on Mar. 26, 1999; International Application No. PCT/US1999/06683, filed on Mar. 26, 1999; U.S. Provisional App. No. 60/079,634, filed on Mar. 27, 1998; and International Application No. PCT/US1998/011348, filed on Jun. 3, 1998. Vault compositions for immunization against chlamydia genital infection are described in U.S. application Ser. No. 12/467,255, filed on May 15, 2009. The entire contents of these applications are incorporated by reference in their entirety for all purposes.

SUMMARY OF THE INVENTION

One embodiment of the present invention provides a vault-like particle comprising a modified MVP where the modified MVP comprises a membrane lytic peptide sequence. In one aspect of this embodiment, the vault-like particle has a membrane lytic peptide sequence added to the N-terminus of the modified MVP. In a further aspect, the membrane lytic peptide sequence comprises the membrane lytic domain of adenovirus VI (pVI) (SEQ ID NO:1). In some further aspects, the membrane lytic domain of adenovirus VI (pVI) comprises SEQ ID NO:3 or SEQ ID NO:4. In a yet further aspect, the modified MVP comprises an EGF domain, which can be added to the C-terminus of the modified MVP. In another further aspect, the modified MVP comprises an antibody binding domain, which can be a Z-domain. In some aspects, the Z-domain is added to the C-terminus of the modified MVP. In some aspects, the vault-like particle further comprises a vault poly ADP-ribose polymerase (VPARP), a telomerase vault associated protein 1 (TEP1), or an untranslated RNA molecule (vRNA).

Another embodiment provides a vault-like particle comprising a membrane lytic domain comprising the amino acid sequence of SEQ ID NO:3, a major vault protein comprising the amino acid sequence of SEQ ID NO:16, and an antibody binding Z domain. In one aspect of this embodiment, the membrane lytic domain is fused to the C-terminus of the major vault protein, and the antibody binding Z domain is fused to the N-terminus of the major vault protein, thereby forming a fusion protein. In some aspects, the fusion protein comprises the amino acid sequence of SEQ ID NO:11.

An additional embodiment provides a method of delivering a substance to a cell, comprising introducing the vault-like particle of the above embodiments to the cell.

Yet another embodiment provides an isolated nucleic acid encoding a pVI-MVP fusion protein comprising an adenovirus protein VI membrane lytic domain sequence and an MVP encoding sequence. In some aspects, the MVP encoding sequence comprises the nucleic acid sequence of SEQ ID NO:17 or SEQ ID NO:2. In further aspects, the pVI-MVP fusion protein comprises the nucleic acid sequence of SEQ ID NO:8.

A further embodiment provides an isolated nucleic acid encoding a pVI-MVP-Z fusion protein comprising an adenovirus protein VI membrane lytic domain, an MVP encoding sequence, and a Z domain sequence. In some aspects of this embodiment, the pVI-MVP-Z fusion protein consists of SEQ ID NO:11. In some aspects, the nucleic acids are contained in a vector, which can be a baculovirus expression vector. In other aspects, the nucleic acids or the vectors are contained within a cell.

A further embodiment provides a method of delivering one or more than one substance to an organism, to a tissue, to a cell, or to an environmental medium by providing a composition comprising a pVI membrane lytic domain consisting of SEQ ID NO:3, and administering the composition to the organism, tissue, cell, or environmental medium. In some aspects, the substance is selected from the group consisting of; a therapeutic nucleic acid, a therapeutic compound, or a toxin. In further aspects, the composition is delivered or targeted to a cell.

A yet further embodiment proves a method of delivering one or more than one substance to an organism, to a tissue, to a cell, or to an environmental medium by providing a composition comprising a vault-like particle comprising a modified MVP, where the modified MVP comprises a membrane lytic peptide sequence, administering the composition comprising the one or more than one substance, or in the presence of the one or more than one substance, to the organism, tissue, cell, or environmental medium. In some aspects, the substance is a therapeutic nucleic acid sequence, where the therapeutic nucleic acid sequence can be a calcium phosphate precipitated cDNA plasmid. In other aspects, the vault-like particle facilitates entry of the one or more than one substance into the cell. In some aspects, the cell can be a RAW 264.7 macrophage or a human A549 epithelial cell.

Another embodiment provides a method of delivering one or more than one substance to a targeted organism, a targeted tissue, or a targeted cell, comprising providing a composition comprising a vault-like particle comprising a modified MVP, where the modified MVP comprises a membrane lytic peptide sequence and a Z-domain, functionally incorporating a selected antibody into the vault-like particle via Z-domain binding, administering the composition comprising the one or more than one substance, or in the presence of the one or more than one substance, to the organism, tissue, cells, or environmental medium. In some aspects, the substance is a therapeutic nucleic acid sequence, which can be a calcium phosphate precipitated cDNA plasmid. In further aspects, the vault-like particle facilitates entry of the one or more than one substance into the targeted cell.

A further embodiment provides a vault-like particle comprising a modified INT where the modified INT comprises a membrane lytic peptide sequence.

In one aspect of this embodiment, the vault-like particle has a membrane lytic peptide sequence added to the N-terminus of the modified INT. In a further aspect, the membrane lytic peptide sequence comprises the membrane lytic domain of adenovirus VI (pVI) (SEQ ID NO:1). In some further aspects, the membrane lytic domain of adenovirus VI (pVI) comprises SEQ ID NO:3 or SEQ ID NO:4.

In a yet further aspect, the modified INT comprises an EGF domain, which can be added to the C-terminus of the modified INT. In another further aspect, the modified INT comprises an antibody binding domain, which can be a Z-domain. In some aspects, the Z-domain is added to the C-terminus of the modified INT. In some aspects, the vault-like particle further comprises a MVP, a telomerase vault associated protein 1 (TEP1), or an untranslated RNA molecule (vRNA).

BRIEF DESCRIPTION OF THE SEVERAL VIEWS OF THE DRAWINGS

These and other features, aspects, and advantages of the present invention will become better understood with regard to the following description, and accompanying drawings, where.

DETAILED DESCRIPTION OF THE INVENTION

Figure 1:
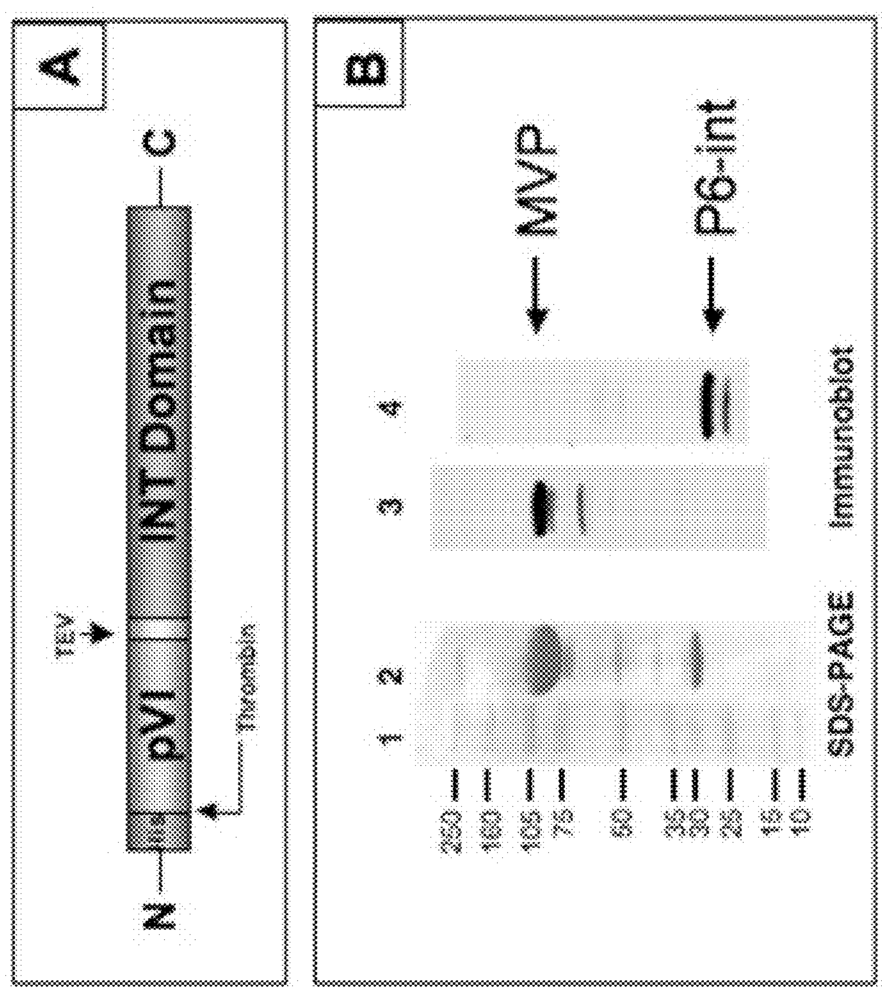
FIG. 1: Incorporation of Ad pVI into recombinant vault particles. (a) Schematic diagram of Ad pVI-INT fusion protein used for vault studies. The N-terminal domain of pVI comprised of residues alanine 34 to glutamic acid 114 were fused to a TEV cleavage site followed by the VPARP INT domain (residues 1563 to 1724). The N-terminal 6His (SEQ ID NO: 55) and thrombin cleavage are derived from the pET28 expression vector. (b) SDS-PAGE and immunoblot of purified pVI-INT vaults. SDS-PAGE (4-15%) and Coomassie blue stain of molecular weight standards (lane 1) and the pVI-INT vaults (lane 2). Immunoblots of pVI-INT vaults probed with anti-MVP monoclonal antibody 1023 (lane 3) or with rabbit polyclonal antisera directed against adenovirus pVI (lane 4).

The descriptions of various aspects of the invention are presented for purposes of illustration, and are not intended to be exhaustive or to limit the invention to the forms disclosed. Persons skilled in the relevant art can appreciate that many modifications and variations are possible in light of the embodiment teachings.

It should be noted that the language used herein has been principally selected for readability and instructional purposes, and it may not have been selected to delineate or circumscribe the inventive subject matter. Accordingly, the disclosure is intended to be illustrative, but not limiting, of the scope of invention.

It must be noted that, as used in the specification, the singular forms "a", "an", and "the" include plural referents unless the context clearly dictates otherwise.

Any terms not directly defined herein shall be understood to have the meanings commonly associated with them as understood within the art of the invention. Certain terms are discussed herein to provide additional guidance to the practitioner in describing the compositions, devices, methods and the like of embodiments of the invention, and how to make or use them. It will be appreciated that the same thing can be said in more than one way. Consequently, alternative language and synonyms can be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the embodiments of the invention herein.

Definitions

Terms used in the claims and specification are defined as set forth below unless otherwise specified.

As used herein, the term "vault" or "vault particle" refers to a large cytoplasmic ribonucleoprotein (RNP) particle found in eukaryotic cells. The vault or vault particle is composed of MVP, VPARP, and/or TEP1 proteins and one or more untranslated vRNA molecules.

As used herein, the term "vault complex" refers to a recombinant vault that encapsulates a small molecule or protein of interest. A vault complex of the invention includes a fusion protein, e.g., an adenovirus protein VI (pVI).

As used herein, the term "vault targeting domain" or "vault interaction domain" is a domain that is responsible for interaction or binding of a heterologous fusion protein with a vault protein, or interaction of a VPARP with a vault protein, such as a MVP. As used herein, the term "mINT domain" is a vault interaction domain from a vault poly ADP-ribose polymerase (VPARP) that is responsible for the interaction of VPARP with a major vault protein (MVP). The term "mINT domain" refers to a major vault protein (MVP) interaction domain.

As used herein, the term "MVP" is major vault protein. The term "cp-MVP" is a cysteine-rich peptide major vault protein.

The term "VPARP" refers to a vault poly ADP-ribose polymerase.

As used herein, the term "TEP-1" is a telomerase/vault associated protein 1.

As used herein, the term "vRNA" is an untranslated RNA molecule found in vaults.

As used herein, the term "fluorescent protein" is a protein that has the property of forming a visible wavelength chromophore from within its polypeptide sequence. Fluorescent proteins can be engineered to be expressed with other proteins, and include, but are not limited to, green fluorescent protein (GFP), red fluorescent protein (mCherry), blue fluorescent protein (EBFP, EBFP2, Azurite, mKalama1), cyan fluorescent protein (ECFP, Cerulean, CyPet) and yellow fluorescent protein derivatives (YFP, Citrine, Venus, YPet).

As used herein, the term "vector" is a DNA or RNA molecule used as a vehicle to transfer foreign genetic material into a cell. The four major types of vectors are plasmids, bacteriophages and other viruses, cosmids, and artificial chromosomes. Vectors can include an origin of replication, a multi-cloning site, and a selectable marker.

As used herein, a "cell" includes eukaryotic and prokaryotic cells.

As used herein, the terms "organism", "tissue" and "cell" include naturally occurring organisms, tissues and cells, genetically modified organisms, tissues and cells, and pathological tissues and cells, such as tumor cell lines in vitro and tumors in vivo.

As used herein, the term "extracellular environment" is the environment external to the cell.

As used herein, the term "in vivo" refers to processes that occur in a living organism.

A "subject" referred to herein can be any animal, including a mammal (e.g., a laboratory animal such as a rat, mouse, guinea pig, rabbit, primates, etc.), a farm or commercial animal (e.g., a cow, horse, goat, donkey, sheep, etc.), a domestic animal (e.g., cat, dog, ferret, etc.), an avian species, or a human.

The term "mammal" as used herein includes both humans and non-humans and include but is not limited to humans, non-human primates, canines, felines, murines, bovines, equines, and porcines.

As used herein, the term "human" refers to "*Homo sapiens.*"

As used herein, the term "sufficient amount" is an amount sufficient to produce a desired effect, e.g., an amount sufficient to modulate protein aggregation in a cell.

As used herein, the term "therapeutically effective amount" is an amount that is effective to ameliorate a symptom of a disease, such as cancer.

A "prophylactically effective amount" refers to an amount that is effective for prophylaxis.

As used herein, the term "stimulating" refers to activating, increasing, or triggering a molecular, cellular or enzymatic activity or response from within a cell or organism.

As used herein, the term "administering" includes any suitable route of administration, as will be appreciated by one of ordinary skill in the art with reference to this disclosure, including direct injection into a solid organ, direct injection into a cell mass such as a tumor, inhalation, intraperitoneal injection, intravenous injection, topical application on a mucous membrane, or application to or dispersion within an environmental medium, and a combination of the preceding.

As used in this disclosure, the term "modified" and variations of the term, such as "modification," means one or more than one change to the naturally occurring sequence of MVP, VPARP or TEP1 selected from the group consisting of addition of a polypeptide sequence to the C-terminal, addition of a polypeptide sequence to the N-terminal, deletion of between about 1 and 100 amino acid residues from the C-terminal, deletion of between about 1 and 100 amino acid residues from the N-terminal, substitution of one or more than one amino acid residue that does not change the function of the polypeptide, as will be appreciated by one of ordinary skill in the art with reference to this disclosure, such as for example, an alanine to glycine substitution, and a combination of the preceding.

As used herein, the term percent "identity," in the context of two or more nucleic acid or polypeptide sequences, refers to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra)

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

As used in this disclosure, the term "comprise" and variations of the term, such as "comprising" and "comprises," are not intended to exclude other additives, components, integers or steps.

It must be noted that, as used in the specification and the appended claims, the singular forms "a," "an" and "the" include plural referents unless the context clearly dictates otherwise.

Compositions of the Invention

As described in more detail below, the invention includes compositions and methods of using vault particles. An embodiment of the invention has recombinant particles having a MVP and a fusion protein, e.g., an adenovirus protein VI (pVI). The vault particle can be used for delivery of a biomolecule, e.g., a vector, to a cell or tumor or subject.

Vaults and Vault Complexes

The compositions of the invention comprise a vault complex. A vault complex is a recombinant particle that encapsulates a small molecule (drug, sensor, toxin, etc.), or a protein of interest, e.g., a peptide, or a protein, including an endogenous protein, a heterologous protein, a recombinant protein, or recombinant fusion protein. Vault complexes are of the invention include an adenovirus protein VI membrane lytic domain. Vault complexes are derived from vault particles.

Vaults, e.g., vault particles are ubiquitous, highly conserved ribonucleoprotein particles found in nearly all eukaryotic tissues and cells, including dendritic cells (DCs), endometrium, and lung, and in phylogeny as diverse as mammals, avians, amphibians, the slime mold *Dictyostelium discoideum*, and the protozoan *Trypanosoma brucei* (Izquierdo et al., *Am. J. Pathol.,* 148(3):877-87 (1996)). Vaults have a hollow, barrel-like structure with two protruding end caps, an invaginated waist, and regular small openings surround the vault cap. These openings are large enough to allow small molecules and ions to enter the interior of the vault. Vaults have a mass of about 12.9±1 MDa (Kedersha et al., *J. Cell Biol.,* 112(2):225-35 (1991)) and overall dimensions of about 42×42×75 nm (Kong et al., *Structure,* 7(4):371-9 (1999)). The volume of the internal vault cavity is approximately $50\times10^3$ $nm^3$, which is large enough to enclose an entire ribosomal protein.

Vaults comprise three different proteins, designated MVP, VPARP and TEP1, and comprise one or more different untranslated RNA molecules, designated vRNAs. The number of vRNA can vary. For example, the rat *Rattus norvegicus* has only one form of vRNA per vault, while humans have three forms of vRNA per vault. The most abundant protein, major vault protein (MVP), is a 95.8 kDa protein in *Rattus norvegicus* and a 99.3 kDa protein in humans which is present in 96 copies per vault and accounts for about 75% of the total protein mass of the vault particle. The two other proteins, the vault poly-ADP ribose polymerase, VPARP, a 193.3 kDa protein in humans, and the telomerase/vault associated protein 1, TEP1, a 292 kDa protein in *Rattus norvegicus* and a 290 kDa protein in humans, are each present in between about 2 and 16 copies per vault.

VPARP, mINT Domain, and mINT Fusion Proteins

A vault poly ADP-ribose polymerase (VPARP) includes a region of about 350 amino acids that shares 28% identity with the catalytic domain of poly ADP-ribosyl polymerase, PARD, a nuclear protein that catalyzes the formation of ADP-ribose polymers in response to DNA damage. VPARP catalyzes an NAD-dependent poly ADP-ribosylation reaction, and purified vaults have poly ADP-ribosylation activity that targets MVP, as well as VPARP itself. VPARP includes a mINT domain (major vault protein (MVP) interaction domain). The mINT domain is responsible for the interaction of VPARP with a major vault protein (MVP).

A vault complex of the invention includes a mINT domain. The mINT domain is responsible for interaction of a protein of interest with a vault protein such as a MVP. In general, the mINT domain is expressed as a fusion protein with a protein of interest. The mINT of the vault complexes of the invention are derived from VPARP sequences. Exemplary VPARP sequences and mINT sequences can be found in Table 1. One of skill in the art understands that the mINT can have the entire naturally occurring sequence or portions of the sequence or fragments thereof. In other embodiments, the mINT has at least 50%, 60%, 70%, 80%, 90%, 95%, 96%, 97%, 98% or 99% sequence identity to any of the VPARP and/or mINT sequences disclosed in Table 1.

In one embodiment, the mINT is derived from a human VPARP, SEQ ID NO:14, GenBank accession number AAD47250, encoded by the cDNA, SEQ ID NO:15, GenBank accession number AF158255. In some embodiments, the vault targeting domain comprises or consists of the INT domain corresponding to residues 1473-1724 of human VPARP protein sequence (full human VPARP amino acid sequence is SEQ ID NO:14). In other embodiments, the vault targeting domain comprises or consists of the mINT domain comprising residues 1563-1724 (SEQ ID NO: 6) of the human VPARP protein sequence. In certain embodiments, the vault targeting domain is at least 90%, 91%, 92%, 93%, 94%, 95%, 96%, 97%, 98%, or 99% identical to SEQ ID NO: 6 or 14.

In alternative embodiments, the mINT domain is derived from TEP1 sequences. One of skill in the art understands that the mINT can have the entire naturally occurring sequence of the vault interaction domain in TEP1 or portions of the sequence or fragments thereof.

MVP

A vault complex of the invention generally includes an MVP. Exemplary MVP sequences can be found in Table 1. One of skill in the art understands that the MVP can have the entire naturally occurring sequence or portions of the sequence or fragments thereof. In other embodiments, the MVP has at least 50%, 60%, 70%, 80%, 90%, 95%, 96%, 97%, 98% or 99% sequence identity to any of the MVP sequences disclosed in Table 1.

In one embodiment, the MVP is human MVP, SEQ ID NO:16, GenBank accession number CAA56256, encoded by the cDNA, SEQ ID NO:17, GenBank accession number X79882. In other embodiments, the MVP is at least 90%, 91%, 92%, 93%, 94%, 95%, 96%, 97%, 98%, or 99% identical to the MVP sequences described herein.

In one embodiment, there is provided a vault complex comprising, consisting essentially of, or consisting of an MVP modified by adding a peptide to the N-terminal to create a one or more than one of heavy metal binding domains. In a preferred embodiment, the heavy metal binding domains bind a heavy metal selected from the group consisting of cadmium, copper, gold and mercury. In a preferred embodiment, the peptide added to the N-terminal is a cysteine-rich peptide (CP), such as for example, SEQ ID NO:18, the MVP is human MVP, SEQ ID NO:16, and the modification results in CP-MVP, SEQ ID NO:19, encoded by the cDNA, SEQ ID NO:20. These embodiments are particularly useful because vault particles consisting of CP-MVP are stable without the presence of other vault proteins.

Any of the vault complexes described herein can include MVPs or modified MVPs disclosed herein.

TEP1

In some embodiments, a vault particle of the invention includes a TEP1 protein. Exemplary TEP1 sequences can be found in Table 1. One of skill in the art understands that the TEP1 can have the entire naturally occurring sequence or portions of the sequence or fragments thereof. In other embodiments, the TEP1 has at least 50%, 60%, 70%, 80%, 90%, 95%, 96%, 97%, 98% or 99% sequence identity to any of the TEP1 sequences disclosed in Table 1.

The TEP1 can be human TEP1, SEQ ID NO:21, GenBank accession number AAC51107, encoded by the cDNA, SEQ ID NO:26, GenBank accession number U86136. Any of the vault complexes described herein can include TEP1 or modifications thereof.

vRNA

A vault complex of the invention can include a vRNA. Exemplary vRNA sequences can be found in Table 1. One of skill in the art understands that the vRNA can have the entire naturally occurring sequence or portions of the sequence or fragments thereof. In other embodiments, the vRNA has at least 50%, 60%, 70%, 80%, 90%, 95%, 96%, 97%, 98% or 99% sequence identity to any of the vRNA sequences disclosed in Table 1.

In one embodiment, the vRNA can be a human vRNA, SEQ ID NO:23, GenBank accession number AF045143, SEQ ID NO:24, GenBank accession number AF045144, or SEQ ID NO:25, GenBank accession number AF045145, or a combination of the preceding.

As will be appreciated by one of ordinary skill in the art with reference to this disclosure, the actual sequence of any of MVP, VPARP, TEP1 and vRNAs can be from any species suitable for the purposes disclosed in this disclosure, even though reference or examples are made to sequences from specific species. Further, as will be appreciated by one of ordinary skill in the art with reference to this disclosure, there are some intraspecies variations in the sequences of MVP, VPARP, TEP1 and vRNAs that are not relevant to the purposes of the present invention. Therefore, references to MVP, VPARP, TEP1 and vRNAs are intended to include such intraspecies variants.

Adenovirus Protein VI

The compositions of the invention include a vault complex including a membrane lytic domain, i.e. the membrane lytic domain of Adenovirus protein VI. In some embodiments, the membrane lytic domain of adenovirus protein VI is fused to an MVP or mINT. [In general, the vault complex includes a membrane lytic domain.]

Biomolecules or Bioactive Agents

As used herein, “biomolecule” or “bioactive agent” refers to any compound or composition having biological, including therapeutic or diagnostic, activity. A bioactive agent may be a pharmaceutical agent, drug, compound, or composition that is useful in medical treatment, diagnosis, or prophylaxis.

The biomolecule or bioactive agent may be any molecule, material, substance, or construct that may be transported into a cell by association with a membrane lytic peptide. The biomolecule or bioactive agent may be, for example, a pharmaceutical agent, a fluorescent moiety, a radioactive moiety, a radiopaque moiety, a paramagnetic moiety, a nanoparticle, a vesicle, a molecular beacon, a marker, a marker enzyme (e.g., horse-radish peroxidase (HRP), beta-galactosidase, or other enzyme suitable for marking a cell), a contrast agent (e.g., for diagnostic imaging), a chemotherapeutic agent, a radiation-sensitizer (e.g., for radiation therapy), a peptide or protein that affects the cell cycle, a protein toxin, or any other other biomolecule suitable for transport into a cell.

Examples of active agents useful as the bioactive agent or biomolecule component of the composition according to the invention include, but are not limited to, .alpha.-adrenergic agonists, .beta.-adrenergic agonists, .alpha.-adrenergic blockers, .beta.-adrenergic blockers, aldose reductase inhibitors, anabolics, analgesics (narcotic and non-narcotic), androgens, anesthetics, anorexics, anthelmintics (e.g., cestode, nematode, onchocerca, schistosoma, and the like), anti-allergics, anti-ameboics, anti-androgens, anti-anginals, anti-arrhythmics, anti-arteriosclerotics, anti-arthritics, antibiotics and other antibacterials, anti-cholinergics, anti-convulsants, anti-depressants, anti-diabetics agents, anti-diarrheals, anti-diuretics, anti-estrogens, antifungals, anti-yeast agents, anti-glaucomas, anti-gonadotropins, anti-gout agents, anti-histaminics, anti-hyperlipoproteinemics, anti-hypertensives, anti-hyperthyroid agents, anti-hypertrophy agents, anti-hypotensives, anti-hypothyroid agents, antiinflammatories, anti-malarials, antimicrobials, anti-migraine agents, anti-nausea agents, anti-neoplastics, antioxidants, antiparasitic agents, anti-parkinsonian agents, anti-pheochromocytoma agents, anti-pneumocytis agents, antiproliferative agents, anti-protozoals (e.g., leishmania, trichomonas, trypansoma, and the like), anti-pruritic agents, anti-psoratic agents, anti-psychotic agents, anti-pyretics, anti-rheumatics, anti ricketts agents, anti-seborrheic agents, antiseptics, anti-spasmodic agents, anti-thrombotic agents, antitussives, anti-ulcer agents, anti-urolithic agents, anti-venins, antivirals, anxiolytics, benzodiazepine antagonists, bronchodilators, calcium channel blockers, calcium regulators, cardiotonics, chelating agents, chemotherapeutics, cholecystokinin antagonists, cholelitholytic agents, choleretics, cholinergics, cholinesterase inhibitors, cholinesterase reactivators, central nervous system stimulants and agents, decongestants, diuretics, dopamine receptor agonists, drugs for treating or preventing pain, ectoparasiticides, enzymes, enzyme inducers, estrogens, gastric secretion inhibitors, glucocorticoids, gonad-stimulating principles, gonadotropic hormones, growth hormones, growth hormone releasing factors, growth stimulants, hemolytics, heparin agonists, hepatoprotectants, hypnotics, immune system boosters, immunomodulators, immunosuppressants, lactation stimulating hormones, LH-RH stimulating agonists, lipotropics, lupus erythmatosus suppressants, mineral corticoids, miotics, monoamine oxidase inhibitors, mucolytics, muscle relaxants, narcotic antagonists, neuroprotectives, neotropics, ovarian hormones, oxytocics, pepsin inhibitors, peristaltic stimulators, progestrogens, prolactin inhibitors, protoglandins, prostoglandin analogs, protease inhibitors, respiratory stimulants, sclerosing agents, sedatives, steroids, thrombolytics, thyrotropic hormones, transdermal penetration enhancers, uricosurics, vasoconstrictors, vasodilators (e.g., cerebral, coronary, peropheral, and the like), vasoprotectants, vitamins, vitamin source extracts, vulneraries (including, but not limited to, those listed in U.S. Pat. No. 5,719,197, the entire disclosure of which is incorporated herein by reference), and combinations thereof. Other additionally or alternately acceptable pharmaceutically active agents can be found, e.g., in U.S. Pat. No. 6,221,383, the entire disclosure of which is incorporated herein by reference.

Fluorescent Proteins

In certain embodiments, the vault complex of the invention includes a fluorescent protein. In some embodiments, the fusion protein comprises a fluorescent protein. Fluorescent proteins can be engineered to be expressed with other proteins, and include, but are not limited to, green fluorescent protein (GFP), red fluorescent protein (mCherry), blue fluorescent protein (EBFP, EBFP2, Azurite, mKalama1), cyan fluorescent protein (ECFP, Cerulean, CyPet) and yellow fluorescent protein derivatives (YFP, Citrine, Venus, YPet). In one embodiment, the fusion protein comprises a mCherry fluorescent protein or a portion of a mCherry fluorescent protein.

Isolated Nucleic Acids and Vectors

Suitable expression vectors generally include DNA plasmids or viral vectors. Expression vectors compatible with eukaryotic cells, preferably those compatible with vertebrate cells, can be used to produce recombinant constructs for the expression of an iRNA as described herein. Eukaryotic cell expression vectors are well known in the art and are available from a number of commercial sources. Typically, such vectors are provided containing convenient restriction sites for insertion of the desired nucleic acid segment. Delivery of expression vectors can be systemic, such as by intravenous or intramuscular administration, by administration to target cells ex-planted from the patient followed by reintroduction into the patient, or by any other means that allows for introduction into a desired target cell.

Plasmids expressing a nucleic acid sequence can be transfected into target cells as a complex with cationic lipid carriers (e.g., Oligofectamine) or non-cationic lipid-based carriers (e.g., Transit-TKO™). Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct may be incorporated into vectors capable of episomal replication, e.g., EPV and EBV vectors. Constructs for the recombinant expression of a nucleic acid encoding a fusion protein will generally require regulatory elements, e.g., promoters, enhancers, etc., to ensure the expression of the fusion nucleic acid in target cells. Other aspects to consider for vectors and constructs are further described below.

Vectors useful for the delivery of a nucleic acid can include regulatory elements (promoter, enhancer, etc.) sufficient for expression of the nucleic acid in the desired target cell or tissue. The regulatory elements can be chosen to provide either constitutive or regulated/inducible expression. A person skilled in the art would be able to choose the appropriate regulatory/promoter sequence based on the intended use of the transgene.

In a specific embodiment, viral vectors that contain the recombinant gene can be used. For example, a retroviral vector can be used (see Miller et al., Meth. Enzymol. 217: 581-599 (1993)). These retroviral vectors contain the components necessary for the correct packaging of the viral genome and integration into the host cell DNA. The nucleic acid sequences encoding a fusion protein are cloned into one or more vectors, which facilitates delivery of the nucleic acid into a patient. More detail about retroviral vectors can be found, for example, in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993). Lentiviral vectors contemplated for use include, for example, the HIV based vectors described in U.S. Pat. Nos. 6,143,520; 5,665,557; and 5,981,276, which are herein incorporated by reference.

Adenoviruses are also contemplated for use in delivery of isolated nucleic acids encoding fusion proteins into a cell. Adenoviruses are especially attractive vehicles for delivering genes to respiratory epithelia or for use in adenovirus-based delivery systems such as delivery to the liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). A suitable AV vector for expressing a nucleic acid molecule featured in the invention, a method for constructing the recombinant AV vector, and a method for delivering the vector into target cells, are described in Xia H et al. (2002), *Nat. Biotech.* 20: 1006-1010.

Use of Adeno-associated virus (AAV) vectors is also contemplated (Walsh et al., Proc. Soc. Exp. Biol. Med. 204:289-300 (1993); U.S. Pat. No. 5,436,146). Suitable AAV vectors for expressing the dsRNA featured in the invention, methods for constructing the recombinant AV vector, and methods for delivering the vectors into target cells are described in Samulski R et al. (1987), J. Virol. 61: 3096-3101; Fisher K J et al. (1996), J. Virol, 70: 520-532; Samulski R et al. (1989), J. Virol. 63: 3822-3826; U.S. Pat. Nos. 5,252,479; 5,139,941; International Patent Application No. WO 94/13788; and International Patent Application No. WO 93/24641, the entire disclosures of which are herein incorporated by reference.

Another preferred viral vector is a pox virus such as a vaccinia virus, for example an attenuated vaccinia such as Modified Virus Ankara (MVA) or NYVAC, an avipox such as fowl pox or canary pox.

The pharmaceutical preparation of a vector can include the vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Examples of additional expression vectors that can be used in the invention include pFASTBAC expression vectors and *E. coli* pET28a expression vectors.

Generally, recombinant vectors capable of expressing genes for recombinant fusion proteins are delivered into and persist in target cells. The vectors or plasmids can be transfected into target cells by a transfection agent, such as Lipofectamine. Examples of cells useful for expressing the nucleic acids encoding the fusion proteins of the invention include Sf9 cells or insect larvae cells. Recombinant vaults based on expression of the MVP protein alone can be produced in insect cells. Stephen, A. G. et al. (2001). *J. Biol. Chem.* 276:23217:23220; Poderycki, M. J., et al. (2006). *Biochemistry* (Mosc). 45: 12184-12193.

Pharmaceutical Compositions of the Invention

In one embodiment, the invention provides methods using pharmaceutical compositions comprising the vault complexes of the invention. These compositions can comprise, in addition to one or more of the vault complexes, a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g. oral, intravenous, cutaneous or subcutaneous, nasal, intramuscular, intraperitoneal routes.

In certain embodiments, the pharmaceutical compositions that are injected intra-tumorally comprise an isotonic or other suitable carrier fluid or solution.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required.

In other embodiments, pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

In some embodiments, administration of the pharmaceutical compositions may be topical, pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; or intracranial, e.g., intraparenchymal, intrathecal or intraventricular, administration. Formulations for parenteral administration may include sterile aqueous solutions which may also contain buffers, diluents and other suitable additives. For intravenous use, the total concentration of solutes should be controlled to render the preparation isotonic.

Methods of Use

Vault complexes described herein can be used to deliver a protein of interest to a cell, a tissue, an environment outside a cell, a tumor, an organism or a subject. In one embodiment, the vault complex comprises an adenovirus pVI domain, and the vault complex is introduced to the cell, tissue, or tumor. In some embodiments, the vault complex is introduced into the extracellular environment surrounding the cell. In other embodiments, the vault complex is introduced into an organism or subject. Delivery of the vault complex of the invention can include administering the vault complex to a specific tissue, specific cells, an environmental medium, or to the organism. In some embodiments, delivery of the vault complex can be detected by a sensor within the cell, tissue, or organism. For example, detection can be performed using standard techniques, such as fluorometry or spectrophotometry. This method can be used, for example, to determine the pH within cells, where the sensor is a pH dependent fluorescent sensor, as will be appreciated by one of ordinary skill in the art with reference to this disclosure.

The methods of the invention comprise delivering a biomolecule to a cell by contacting the cell with any of the vault complexes described herein. Cells of the invention can include, but are not limited to, any eukaryotic cell, mammalian cell, or human cells, including tumor cells. In some embodiments, contacting the cell with a vault complex induces migration of T cells and/or dendritic cells to the cell.

Methods of the invention include delivery of the vault complex to a subject. The delivery of a vault complex to a subject in need thereof can be achieved in a number of different ways. In vivo delivery can be performed directly by administering a vault complex to a subject. Alternatively, delivery can be performed indirectly by administering one or more vectors that encode and direct the expression of the vault complex or components of the vault complex. In one embodiment, the vault complex is administered to a mammal, such as a mouse or rat. In another embodiment, the vault complex is administered to a human.

In one embodiment, the methods of delivery of the invention include systemic injection of vault complexes to tumors, producing the enhanced permeability and retention (EPR) effect. See Maeda et al., *J. of Controlled Release* 2000, 65: 271-284; Griesh, K., *J. of Drug Targeting* 2007, 15(7-8): 457-464; Allen et al., *Science* 2004, 303:1818-1822. Solid tumors possess extensive angiogenesis and hence hypervasculature, defective vascular architecture, impaired lymphatic drainage/recovery systems, and greatly increased production of a number of permeability mediators. Due to the biology of solid tumors, macromolecular anticancer drugs and agents, including vault complexes, administered intravenously can accumulate and are retained in the tumor due to the lack of efficient lymphatic drainage in the solid tumor. The invention includes methods of systemic or targeted delivery of vault complexes described herein to solid tumors, such as those found in lung cancer.

Other methods of the invention include stimulating an immune response in a subject. The method comprises administering the vault complex to a subject. Administering can include intra-tumoral injection of the vault complex in a subject, which is described in detail herein.

Methods of Treatment

The invention features a method of treating or managing disease, such as cancer, by administering the vault complex of the invention to a subject (e.g., patient). In some embodiments, the method of the invention comprises treating or managing cancer in a subject in need of such treatment or management, comprising administering to the subject a therapeutically effective amount of the vault complexes described herein.

The data obtained from cell culture assays and animal studies can be used in formulating a range of dosage for use in humans. For any compound used in the methods featured in the invention, the therapeutically effective dose can be estimated initially from cell culture assays. A dose may be formulated in animal models to achieve a circulating plasma concentration range of the vault complex. Such information can be used to more accurately determine useful doses in humans. Analysis of tumor cell samples of mice administered a vault complex can also indicate a therapeutically effective dose.

The pharmaceutical composition according to the present invention to be given to a subject, administration is preferably in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of protein aggregation disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980. A composition can be administered alone or in combination with other treatments, either simultaneously or sequentially dependent upon the condition to be treated.

In certain embodiments, the dosage of vault complexes is between about 0.1 and 10,000 micrograms per kilogram of body weight or environmental medium. In another embodiment, the dosage of vault complexes is between about 1 and 1,000 micrograms per kilogram of body weight or environmental medium. In another embodiment, the dosage of vault complexes is between about 10 and 1,000 micrograms per kilogram of body weight or environmental medium. For intravenous injection and intraperitoneal injection, the dosage is preferably administered in a final volume of between about 0.1 and 10 ml. For inhalation the dosage is preferably administered in a final volume of between about 0.01 and 1 ml. As will be appreciated by one of ordinary skill in the art with reference to this disclosure, the dose can be repeated a one or multiple times as needed using the same parameters to effect the purposes disclosed in this disclosure.

For instance, the pharmaceutical composition may be administered once for each tumor in a subject, or the vault complex may be administered as two, three, or more subdoses or injections at appropriate intervals. In that case, the vault complexes can be injected in sub-doses in order to achieve the total required dosage.

The vault complexes featured in the invention can be administered in combination with other known agents effective in treatment of cancers, including lung cancer. An administering physician can adjust the amount and timing of vault complex administration or injection on the basis of results observed using standard measures of efficacy known in the art or described herein. The skilled artisan will also appreciate that certain factors may influence the dosage and timing required to effectively treat a subject, including but not limited to the severity of the disease or disorder, previous treatments, the general health and/or age of the subject, and other diseases present.

Methods of Preparing Vault Complexes

The methods of the invention include preparing the vault complexes described herein.

In one embodiment, the vault complexes are derived or purified from natural sources, such as mammalian liver or spleen tissue, using methods known to those with skill in the art, such as for example tissue homogenization, differential centrifugation, discontinuous sucrose gradient fractionation and cesium chloride gradient fractionation. In another embodiment, the vault complexes are made using recombinant technology. Details about the methods for recombinant vault complexes are described below.

In some embodiments, a target of interest, i.e., protein of interest, is selected for packaging in the vault complexes. The target of interest may be selected from the group consisting of an enzyme, a pharmaceutical agent, a plasmid, a polynucleotide, a polypeptide, a sensor and a combination of the preceding. In a preferred embodiment, the target of interest is a recombinant protein, e.g., a membrane lytic protein, e.g., an adenovirus protein VI.

Preferably, if the target of interest is a recombinant protein, the polynucleotide sequences encoding the recombinant protein are used to generate a bacmid DNA, which is used to generate a baculovirus comprising the sequence. The baculovirus is then used to infect insect cells for protein production using an in situ assembly system, such as the baculovirus protein expression system, according to standard techniques, as will be appreciated by one of ordinary skill in the art with reference to this disclosure. Advantageously, the baculovirus protein expression system can be used to produce milligram quantities of vault complexes, and this system can be scaled up to allow production of gram quantities of vault complexes according to the present invention.

In another embodiment, the target of interest is incorporated into the provided vaults. In a preferred embodiment, incorporation is accomplished by incubating the vaults with the target of interest at an appropriate temperature and for an appropriate time, as will be appreciated by one of ordinary skill in the art with reference to this disclosure. The vaults containing the protein of interest are then purified, such as, for example sucrose gradient fractionation, as will be appreciated by one of ordinary skill in the art with reference to this disclosure.

In other embodiments, the vaults comprising the target of interest are administered to an organism, to a specific tissue, to specific cells, or to an environmental medium. Administration is accomplished using any suitable route, as will be appreciated by one of ordinary skill in the art with reference to this disclosure.

In one embodiment, the method comprises preparing the composition of the invention by a) mixing a fusion protein comprising a pVI fused to a mINT generated in Sf9 cells with a rat MVP generated in Sf9 cells to generate a mixture; b) incubating the mixture for a sufficient period of time to allow packaging of the fusion protein inside of vault complexes, thereby generating the composition. Sf9 cells are infected with pVI-MVP encoding recombinant baculoviruses. Lysates containing recombinant pVI-INT and rat MVP generated in Sf-9 cells can be mixed to allow the formation of a macromolecular vault complex containing the pVI-INT fusion protein.

In another embodiment, the composition is prepared by a) mixing a fusion protein comprising a pVI fused to a mINT generated in insect larvae cells with a rat MVP generated in insect larvae cells to generate a mixture; b) incubating the mixture for a sufficient period of time to allow packaging of the fusion protein inside of vault complexes.

Details about methods of preparing vault complexes are further described in the Examples.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* 3$^{rd}$ Ed. (Plenum Press) Vols A and B(1992).

Methods cDNA Constructs for the Expression of Recombinant pVI Proteins cDNA plasmid constructs encoding the mature, full length protein VI (pVI), designated p6, or the N-terminal region of protein VI (NT) corresponding to residues ala-34 to glu-114, designated nt, were cloned into the BamHI and EcoRI sites of the *Escherichia coli* expression vector pET28a (Novagen, Madison, WI.). The constructs also included an N-terminal 6His tag (SEQ ID NO: 55) followed by a thrombin cleavage site. The 5' and 3' primers, containing a BamHI restriction site (underlined) in the 5' primers and a TTA stop codon site (italics) and an EcoRI restriction site (underlined) in the 3' primers were used as indicated:

```
for pVI
                                        (SEQ ID NO: 43)
5'-CGGGATCCGCCTTCAGCTGGGGCTCGCTCTGGAGC-3'
and

                                        (SEQ ID NO: 44)
5'-CGGGAATTCTTACAGACCCACGATGCTGTTCAG-3'

for NT
                                        (SEQ ID NO: 45)
5'-CGGGATCCGCCTTCAGCTGGGGCTCGCTCTGGAGC-3'
and

                                        (SEQ ID NO: 46)
5'-CGGGAATTCTTACTCTCGGGAGGGCGGGGATC-3'
and

for TR
                                        (SEQ ID NO: 47)
5'-AAAGGATCCTATGGCAGCAAGGC-3'
and

                                        (SEQ ID NO: 48)
5'-AAAGAATTCTTACAGACCCACGATGCTGTT-3'.
```

For vault incorporation experiments, we also expressed pVI (amino acid residues 34-53) in *E.Coli*. using 5'CG GGATCCGCCTTCAGCTGGGGCTCGCTGTGGAGCGG CATTAAAAATTTCGGTT CCACCGTTAAGAACTAT GAATTCCGG-3' (SEQ ID NO:49) and 5'-CCGGAATTCATAGTTCTTAACGGTGGAACCGAAATT TTTAATGCCGCTCCACAGCGAGCCCCAGCTGAAGG CGGATCCCG-3' (SEQ ID NO:50) primers. After endonuclease restriction digests with BamHI and EcoRI, the resulting 60 by cDNA fragment was inserted into pET 28a vector containing His tag at the N terminus. All plasmid constructs were confirmed by sequencing.

Cloning, Expression, and Purification of Vault Complexes

The cDNA constructs encoding the INT and MVP were previously described [9, 10, 11, 12]. The INT domain corresponds to the 162-aa C-terminal region of VPARP (amino acids 1563-1724) and is the smallest region identified for interaction with MVP. The INT domain coding region was PCR cloned into the Bam HI and XhoI sites of the *E.coli* expression vector pET28a using the sense primer, 5'-CG GGATTCGGCGGCGAATTCGATTTACGATATCCCAAC GACCGAA-3' (SEQ ID NO:51), with BamHI site (underlined) and EcoRI site (underlined italics). The sense primer contains a dipeptide flexible linker, Gly-Gly, and an added EcoRI site designed for further insertion of recombinant pVI-NT. The antisense primer, 5'-CCCCTCGAGTTAGCCT TGACTGTAATGG AGGACTCTATG-3' (SEQ ID NO:52) contains an XhoI site (underlined) and a stop codon (italics).

The interaction domain chosen for pVI constructs encompassed amino acids 1563-1724 of VPARP. These pVI-INT fusion molecules were expressed in bacteria and purified as described above. Recombinant vaults based on expression of the MVP protein alone were produced in insect cells as previously described [10, 13]. Purified vaults were also analyzed by immunoblot using polyclonal antibodies to MVP, INT, or pVI. The identity of CP-MVP-Z monomer present in vault particles was also confirmed by MALDI-TOF-M8, which is within the error range of expected molecular masses of CP-MCP-Z monomers [12].

Protease Sensitivity and Transmission Electron Microscopy

To examine the protease sensitivity of purified vault particles, 30 μL of purified pVI-vaults (150 μg/ml) were incubated with 6 μL of 10× thrombin cleavage buffer, 3 μL of thrombin (1 U/μL, Novagen, Madison, Wis.) and 21 μL of water to a total volume of 60 μL. The reaction mixture was incubated at 25° C. Aliquots (10 μL) of this mixture were collected after 24 h and analyzed by immunoblot as described above. Purified vault particle morphology was assessed by negative stain transmission electron microscope as previously described [10]. EM grids were examined on a JEOL 1200 EX elecron microscope and micrographs were captured with a BIOScan 600W digital camera (Gatan Inc., Pleasanton, Calif.).

Liposome Disruption Assay

To assess the ability of pVI or pVI-vaults to mediate membrane disruption, we used model membranes (liposomes) containing an entrapped fluorescent dye. Unilamellar liposomes having an average diameter of 500 μm were prepared using bovine liver phosphatidylcholine (PC), and bovine brain phosphatidylserine (PS) (Avanti Polar Lipids) and sulforhodamine B (SulfoS) (Molecular Probes, Invitrogen) as previously described [14] with slight modifications. Lipid vesicles were prepared by mixing lipids in a molar ratio of PC to PS of 4:1 in a total amount of 5.0 μmole) in 1 ml of chloroform. The solution was then evaporated under argon to generate a lipid film which was vacuum-dried for 12 hrs to remove residual chloroform. The dried lipid film was then hydrated for 1 hr in 1 ml solution of sulforhodamine B (100 mM) in HBS buffer (20 mM HEPES/NaOH buffer, 100 mM NaCl, 0.02% sodium azide pH 7.5). Small unilamellar vesicles (SUVs) were prepared by vortexing the reaction tube vigorously to completely resuspend the lipid mixture followed by sonication for 1 hr in a bath sonicator (Laboratory Supplies Inc). This final solution was then gel-filtered on a Sephadex G-25 column and eluted with HBS buffer. The liposomes, which eluted as a pink band, were collected and used within 24 hours. The final lipid concentration was determined by using an inorganic phosphorus assay [15, 16] and then adjusted to 0.15 mM for the vault and pVI-INT assays as described below.

Time-dependent fluorescence was used to analyze liposome disruption using an Aminco Bowman Series Luminescence Spectrometer equipped with 535/20 nm excitation and 585/20 nm emission filters, respectively. Briefly, 12.5 μl of liposome solution was added to HBS buffer (1 ml) in a fluorescence cuvette equipped with a stir bar and fluorescence measurements were taken at 1 second intervals under stirring conditions for a total time of approximately 7 minutes. After 60 seconds to record background fluorescence, 10 μl of the pVI-INT proteins (1 μg total) or vault-pVI complexes at 13.7 mg/mJ (137 μg total) in 50 mM Tris, 300 mM NaCl, pH 8 were added to the liposome solutions. After reaching a plateau in the fluorescence signal, 25 μl of a 10% aqueous solution of Triton X-100 was added and the percentage of SulfoS release was calculated using the following formula: % SulfoS released=$100\times[(F-F_o)/(F_t-F_o)]$, where $F_o$ and F are the fluorescence before and after the addition of protein, respectively, and $F_t$ is the total fluorescence intensity in the presence of Triton X-100.

Preparation of Fluorescent Vault Nanoparticles

Recombinant vaults were fluorescently labeled using the NHS-Ester Cy3.5 bis reactive dye (Amersham Biosciences). Briefly, 1.0 mg of the free bisfunctional NHS-Ester Cy3.5 dye was dissolved in 1 ml of 0.1M carbonate buffer, pH 8.5 and then mixed with 0.65 ml of 13.7 mg/ml purified vaults resulting in the conjugation at a molar ratio of 1.1 dye molecules per 1 MVP molecules. The conjugation mixture was incubated at 4° C. for 40 minutes with occasional rocking and the remaining non-conjugated dye was removed by filtration on a PD-10 column (Amersham Biosciences) pre-equilibrated with buffer A (see above) that was also used for elution of the conjugation product. The colored (pink) fraction containing the dye-conjugated vault nanoparticles was collected and loaded onto a discontinuous 20-60% sucrose density gradient and ultracentrifuged as described above. The pink band corresponding to the 45% fraction was pelleted by centrifugation using a Beckman Ti70 rotor (39,000 rpm for 2 hr at 4° C.) and resuspended in 20 mM MES buffer pH 6.5. The yield of labeled vault particles was estimated by linear regression analyses of the UV absorbance of the labeled vaults assuming Cy3.5 dye $\lambda_{ex}$=581 nm and $\lambda_{ex}$ of proteins at 280 nm resulting in a ratio of 1 Cy3.5 dye molecules per MVP protein subunit.

Vault Interactions with Mammalian Cells

RAW 264.7 mouse macrophages and A549 human epithelial cells were maintained in Dulbecco's complete modified Eagle's medium (DMEM) supplemented with 10 mM HEPES, 2 mM glutamine, 1 mM pyruvate, 0.1 mM nonessential amino acids, 100 U of penicillin G/ml, 0.3 mg of gentamicin/ml, and 10% fetal bovine serum (D-10). U937 human monocytic cells, maintained in RPMI-1640 modified medium, were supplemented with 10 mM HEPES, 2 mM glutamine, and 10% fetal bovine serum.

To measure vault-host cell interactions, cells were cultured 6-well tissue culture plates at a density of $2\times10^5$ cells/well 24 hours prior to measuring vault internalization. The cells were then incubated with varying amounts of Cy3.5-labeled vault nanoparticles in MES buffer for varying times at 37° C. or 4° C. Internalized vaults were then quantified by flow cytometry following the detachment of cells by trypsinization and resuspension in 1 ml of cold $Ca^{2+}$ and $Mg^{2+}$ free PBS buffer, pH 7.0, containing 1 mM EDTA, 25 mM HEPES and 1% heat inactivated fetal bovine serum. Trypan blue dye was then added to each cell sample at a final concentration of 200 μg/ml in cold FACS sort buffer in order to quench the fluorescence of non-internalized Cy3.5-labeled vault particles as previously described [17]. The cell suspensions were analyzed by flow cytometry with a Becton-Dickinson FACSCan cytometer using a 488 nm laser for red emitting fluorochromes excitation. Cy3.5 fluorescence was detected using PL2 channel in conjunction with a 585 nm band-pass filter. An electronic gate was set around cells based on the forward and side scatter properties of the population and a minimum of 10,000 gated events per sample were collected. Data analysis was performed with CellQuest software (BO Bioscience, San Jose, Calif.).

Cell Membrane Penetration Assay

To examine vault mediated endosome penetration we used an assay that measures the co-delivery of a ribotoxin (saporin) into the cytosol of host cells via a membrane lytic virus [18]. RAW 264.7 cells were seeded at a density of 3000 cells per well and allowed to attach for 4 hr in 96-well tissue culture plate. One microgram of vaults alone, or vault-PVI complexes, or pVI protein were incubated with cells in the presence or absence of the ribotoxin saporin [19] in D-1 0 medium for 4 hrs. The saporin concentration was varied from $1.65\times10^{-7}$ M to $8.25\times10^{-9}$ M in two-fold dilutions. The cultured cells were then washed two times with PBS buffer and media and then cultured in medium for 48 hours before measuring cell metabolic activity using the colorimetric XTT assay [22-25] (Promega, Madison, Wis.). The absorbance was measured at 485 nm on a Molecular Devices SpectraMAX 250 microplate reader. All experiments were performed in triplicate.

Vault-Mediated Delivery of CaPi:DNA Complexes

The murine macrophage RAW 264.7 cells were cultured in 60-mm dishes in D-10 medium (DMEM+10% FCS medium and antibiotics) and seeded onto 96-well plates ($6\times10^3$ cells per well, in 0.2 ml growth medium) 24 hrs prior to performing transfection experiments. A plasmid encoding a redshifted variant of GFP (pEGFP-N1—Clontech, Palo Alto, Calif.) was amplified in the *E. coli* (DH5α) and purified according to the manufacturer's protocol (Qiagen, USA). The isolated DNA was resuspended in Tris-EDTA (pH 8.0) at a concentration of 0.5 μg/μl and used for the preparation of calcium phosphate precipitates for transfection experiments as previously described [22-25]. Briefly, 1.5 μl of DNA plasmid encoding GFP (0.75 μg) along with calculated volumes of pVI-Vault solution ($5.39\times10^{-7}$ M, $5.68\times10^6$ particles Icell) and 1.00 μl of a 2 M $CaCl_2$ (Profection®, Calcium-Phosphate mammalian transfection system; Promega, Madison, Wis.) aqueous solution were mixed with of EMEM (11 090-81, GIBCO) in a final volume of 50 μl. The mixtures were allowed to incubate for 30 min at 4° C. The cell culture medium was replaced by 150 μl of fresh EMEM medium and 50 μl of the complex was then applied to cells with gentle agitation. After incubation for 1 hr at 37° C., the transfection mixture was removed by washing the cells with 0.15 M NaCl and cultured with D-10 medium. pEGFP gene expression was measured by FACS after 1 day post-transfection.

Recombinant pVI-MVP Vault Protein Constructs

The pVI lytic peptide (aa 34-53, AFSWGSLWSGIKNFGSTVKN (SEQ ID NO: 3)) was fused to the N-terminus of MVP. The following PCR primers were used: pVI reverse: GGG GCC ATG GCG CTG CCG CGC GGC ACC AGG CCG TTC TTA ACG GTG GAA CCG (SEQ ID NO:53) and pVI forward: CTC TGC TAG CCA CCA TGG CCT TCA GCT GGG GCT CG (SEQ ID NO:54) and the template was pVI-mINT in pFastBac. All the primers used in this study were purchased from Invitrogen. The PCR product was gel purified on a column, ligated to PCR 2.1 vector followed by the amplification and purification by Qiagen miniprep kit. The insert was NcoI digested, gel purified, and ligated to NcoI and phosphatase treated rat MVP cDNA inserted in pFastBAC to form pVI-MVP pFastBac. All constructs were confirmed by DNA sequence analysis carried out by Laragen. The constructs encoding EGF vaults, CP-MVP vaults, CP-MVP-Z vaults, pVI-mINT, and mCherry-mINT were described previously. (refs 26-28). The Z domain was subcloned from CP-MVP-Z using Xho I and KpnI and the gel purified 1 kb fragment was inserted into the same sites in pVI-MVP in pFastBac to form pVI-MVP-Z in pFastBac.

Co-Delivery of CaPi DNA via Recombinant pVI-MVP Vault Protein Constructs

The pVI-MVP and pVI-MVP-Z recombinant vaults were expressed in Sf9 insect cells. The vaults were purified as described previously. In order to eliminate the aggregation into vaultimers, buffer A with 25 mM NaCl was used for the purification. In case of EGF+pVI-INT vault purification, buffer A with 150 mM NaCl was used. pVI pellets were resuspended in Bugbuster (Novagen, USA) protein extraction reagent supplemented with Benzonase (20 U/mL, Novagen, USA), 1.0 mg/mL of lysozyme (Sigma, USA), and one tablet of EDTA-free protease inhibitor cocktail (Roche, Switzerland). In order to incorporate different pVl molecules into the interior of the vaults, ~2 mg of purified pVI-INT proteins in 10 mL of Bugbuster buffer was added to 10 mL of recombinant vault containing Sf9 cell lysates, and the mixture was incubated on ice for 30 min before performing vault purification as previously [29, 30]. The purified vaults were stored at 4° C. in 20 mM MES at pH 6.5 until used.

Expression and Purification of Recombinant pVI-MVP Vault Protein Constructs

The pVIA431 and HeLa cells were grown and maintained in DMEM supplemented with 10% fetal bovine serum. For the transfection with EGF vaults, the cells ($5\times10^4$ cell/well) were seeded on the 24-well culture plates and incubated for 16 h under serum starvation. The determined amounts of EGF vaults were added to the cell culture followed by 1 h incubation at 4° C. with 300 μL of the medium containing 0.2% serum. Then the unbound vaults were washed out with PBS (−) three times and CaPi DNA were added to each well with 400 μL of the medium containing 10% serum. The $CaPO^4$ precipitation of pDNA was followed by the recommended protocol of maker (Mammalian Transfection Kit, Stratagene, USA). Briefly 0.96 μL of 2.5M $CaCl_2$ solution was mixed with 0.8 μg of pDNA. The mixture was incubated for 30 min at RT and then applied to each well for the transfection. After 24 h of incubation (4 h incubation for Lipofectamine as recommended from maker), the medium was replaced with 400 μL of the medium containing 10% serum, followed by an additional 48 h of incubation. For the transfection with pVI-MVP-z vaults, the cells were serum starved for 1 h and the vaults were pre-incubated with anti-EGFR, clone LA22 monoclonal antibody (Millipore, USA) for 16 h before added to cell culture. For the CaPi DNA preparation, 1.8 μL of 2.5M CaCl2 solution was mixed with 1.5 μg of pDNA. The mixture was incubated for 30 min at RT and then applied to each well for the transfection. For non-targeted transfection with pVI-MVP vault, the mouse macrophage RAW 264.7 cells (5×104 cell/well) were seeded on 24-well culture plates and incubated for 16 h in 400 μL of DMEM containing 10% FBS before transfection. The recombinant vaults and CaPi DNA were added to the cell culture and co-incubated for 24 h followed by the 48 h of post-incubation. The luciferase gene expression was then evaluated using the Luciferase Assay System (Promega, USA) and a Lumat LB9507 luminometer (Berthold Technologies, Germany). The amount of protein in each well was concomitantly determined using a Micro BCA Protein Assay Reagent Kit. A plasmid encoding luciferase was amplified in the *E.coli* and purified using Maxiprep kit (Qiagen, USA).

Vault-Mediated Endosome Penetration of Ribotoxin

To evaluate cell membrane penetration, we measured the delivery of a saporin (sigma, USA) into the cytosol of the murine macrophage RAW 264.7 cells via pVI-MVP. The cells (3,000 cells/well) were seeded on 96-well tissue culture plate and incubated overnight in DMEM containing 10% FBS. The calculated amount of vaults was applied to each well in the presence or absence of the saporin in DMEM for 4 h. The cultured cells were washed three times with PBS buffer and cultured in medium for 48 h before measuring cell viability using MTT assay kit (Roche, Switzerland). The absorbance was measured at 560 nm on a Victor3 1420 multilabel counter (PerkinElmer, USA). All experiments were performed in triplicate.

Endocytosis of Recombinant Vaults

A431 or HeLa cells ($4\times10^4$/well) were plated onto 12 mm glass coverslips coated with poly-L-lysine in 4-well Petri dishes and incubated at 37° C. (with 5% $CO_2$) for 16 h. Purified pVI-MVP-Z/mCherry-INT vaults (100 μg) were incubated with anti-EGFR antibody LA22 (1 μg) in PBS containing 0.05% Tween 20 (Fisher Scientific, USA) at 4° C. for 16 h with tumbling. The cells were serum-starved for 1 h before the addition of antibody-bound vaults, followed by 1 h incubation at 4° C. in DMEM (0.25 mL containing 0.2% FBS per well) for specific membrane binding studies. They were washed three times with PBS and incubated with Lysotracker Green DND-26 (Invitrogen, USA) at 37° C. Then the cells were washed three times with cold PBS and fixed in 4% paraformaldehyde and nucleus stained with Hoechst 33342 (Invitrogen, USA). Cells were mounted in Vinol 205 and visualized using fluorescent microscopy (Axio Imager Z1 microscope, Carl Zeiss, Germany).

Example 1

Incorporation of pVI into Recombinant Vault Particles

Despite the potential utility of vaults as gene transfer carriers, these nanoparticles have not been reported to display cell membrane penetrating activity, thus potentially limiting their cell transducing capacity. To overcome this deficiency, we have incorporated the membrane lytic domain of adenovirus protein VI into recombinant vault particles. Adenovirus internalization via endocytosis leads to the partial disassembly of the viral capsid concomitant with the release of protein VI [18]. The N-terminal region of pVI contains a putative amphipathic a-helical domain (amino acid residues 34-53) that exhibits potent membrane lytic activity as measured by the disruption of artificial lipid membranes (liposomes) [18]. The studies reported herein demonstrate that incorporation of the N-terminal domain of pVI into vault particles increases membrane penetration as well as the co-delivery of reporter molecules.

Figure 2:
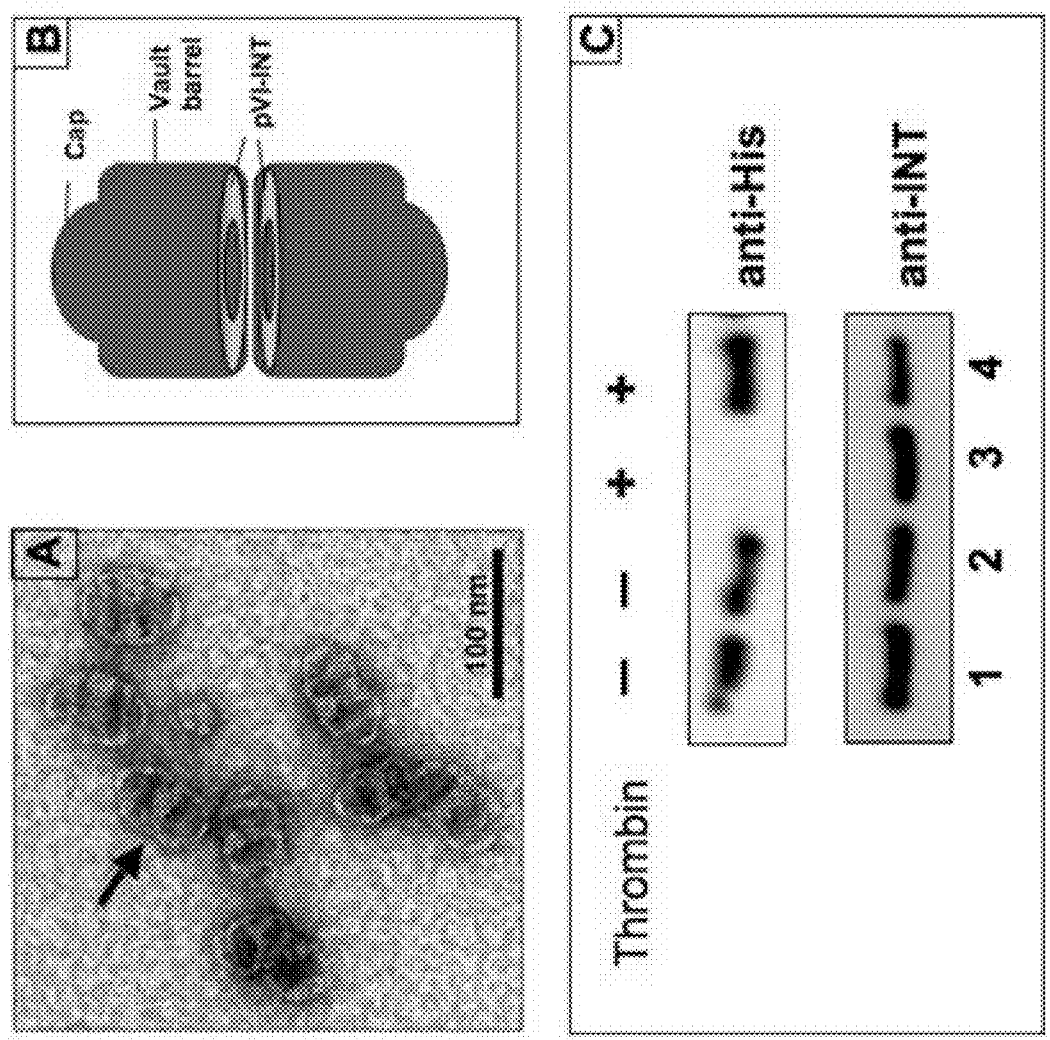
FIG. 2: Transmission electron microscopy and biochemical analysis of vault particles. (a) Negative stain TEM image of vaults containing pVI-INT. Note the presence of additional protein mass in the waist region of the vault barrel (arrow), which based on earlier structural studies, is the expected location of pVI-INT as depicted in (b). (c) Immunoblot using anti-His tag antibody (upper panel) or anti-INT antibody (lower panel) of pVI-INT protein (lane 1), pVI-vaults (lane 2), thrombin-treated pVI-INT (lane 3) or thrombin-treated pVI-vaults (lane 4). Note that since only 17 amino acids are cleaved off of pVI-INT, digestion with thrombin would cause only a minor change in the apparent molecular weight of the fragment observed in the gel.

Previous biochemical studies demonstrated that the interior surface of vaults could be targeted to bind exogenous proteins engineered to contain an MVP interaction domain (INT) derived from the VPARP protein (amino acid residues 1532-1724) [9]. Therefore, we examined whether the membrane lytic domain of adenovirus protein VI (amino acid residues 34-114) [18] could be incorporated into the interior of recombinant vault particles via fusion to the VPARP INT domain (FIG. 1*a*). Incubation of recombinant MVP and pVI-INT proteins allowed the formation of a macromolecular vault complex that could be isolated by density gradient ultracentrifugation. The purified vaults contained both MVP as well as pVI-INT as indicated by immunoblot analyses (FIG. 1*b*). Based on densitometric analysis of stained SDS-PAGE, we estimate that on average, each vault particle contains approximately two molecules of protein VI-INT. The pVI-vault complex also exhibited a very similar sedimentation profile on sucrose gradients as empty vaults or vault particles containing the INT domain fused to eGFP (data not shown) suggesting that incorporation of pVI-INT did not impact the normal structure of recombinant vault particles. To verify this, we examined purified vault-pVI complexes by negative stain transmission electron microscopy (FIG. 2*a*). Vault-pVI complexes exhibited the characteristic barrel shaped morphology with additional density observed near the "waist" of some of these particles (FIGS. 2*a,b*), consistent with the previously established binding site for recombinant-INT fusion proteins.

We next examined whether the pVI-INT protein was located inside vault particles or non-specifically associated with the exterior of the vault. Vault-pVI particles (FIG. 2*c*, lanes 2 and 4) or the purified pVI-INT protein (FIG. 2*c*, lanes 1 and 3) were subjected to digestion with thrombin to determine if specific sites within the pVI-INT fusion protein were accessible to this protease, and the protease-treated samples were then analyzed by immunoblot. Vault-pVI complexes were resistant to thrombin digestion as detected with an anti-His tag MAb (FIG. 2*c*, lane 4). In contrast, soluble recombinant pVI-INT alone that had not been incorporated into vaults was susceptible to thrombin cleavage (FIG. 2*c*, lane 3). Control samples treated with thrombin and analyzed with an anti-INT polyclonal antibody did not reveal protease susceptibility, consistent with the retention of the C-terminal INT domain. These findings indicated that pVI-INT could be incorporated into the interior of recombinant vaults, however a concern was that the membrane lytic activity of this Ad-derived protein might not be retained upon fusion to the relatively large VPARP INT domain.

Example 2

Membrane Lytic Activity of Recombinant Vault Particles

Figure 3:
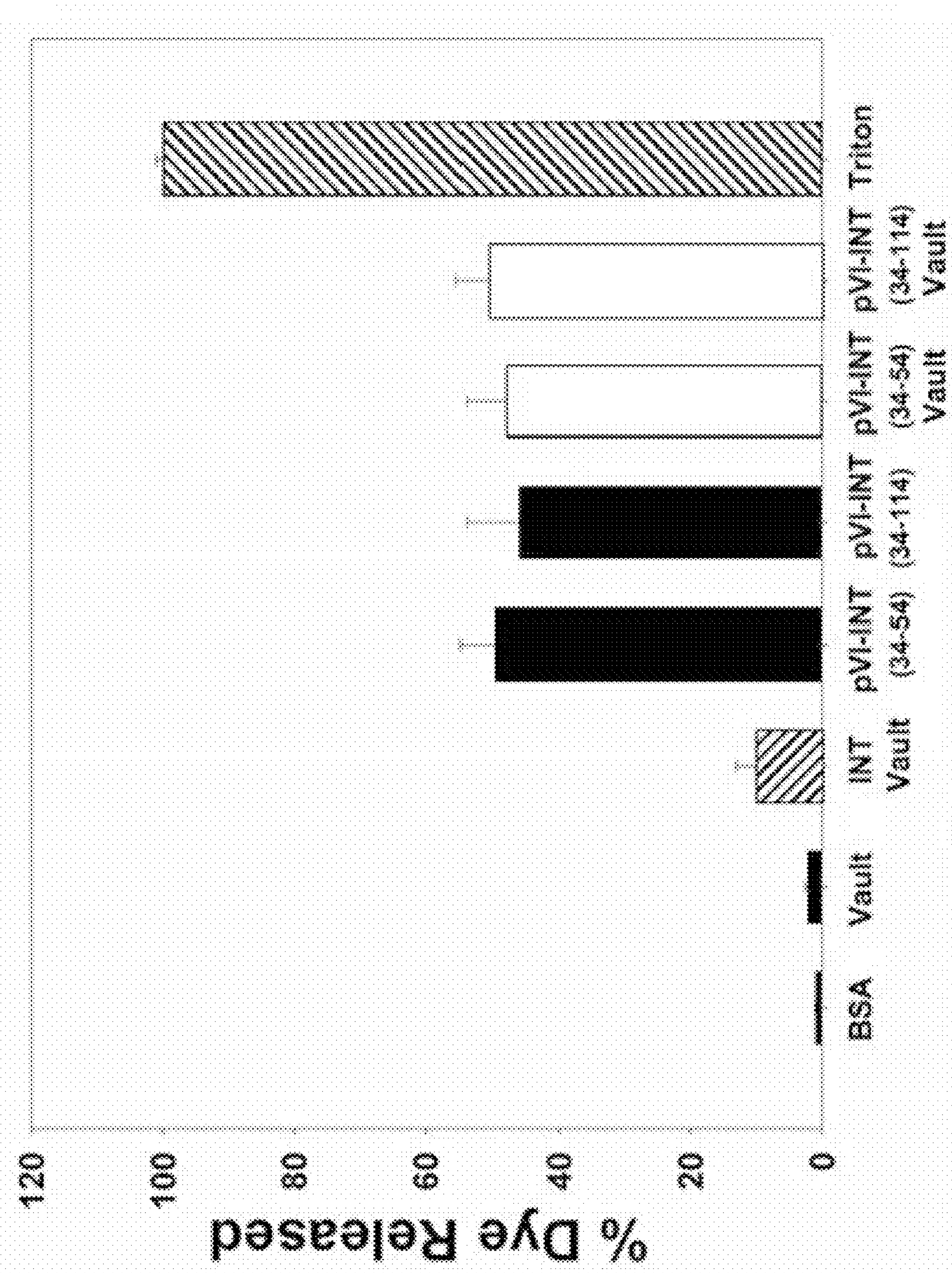
FIG. 3: Disruption of liposomes by recombinant pVI-INT or pVI-INT incorporated into vaults. Unilamellar liposomes containing sulforhodamine B were used to measure fluorescence (dye release) at 585 nm in a cuvette with constant stirring. Background fluorescence was recorded for 60 sec and then the liposomes were incubated at 37° C. with 1 μg of different recombinant pVI-INT proteins (black bars) or 137 μg of vault-INT (grey bar) or 137 μg of different vault-pVI complexes (red bars) was recorded for an interval of 7 minutes. All measurements were performed in triplicate. The membrane lytic activity mediated by the proteins or complexes was expressed as the percentage of dye release relative to that achieved with Triton X-100. Disruption by bovine serum albumin (BSA) or empty vault particles alone were included as a negative control. The data shown is representative of three different experiments.

We measured the membrane lytic activity of pVI-INT fusion proteins alone or pVI-INT fusion proteins incorporated into vault particles using artificial membranes (liposomes) containing an entrapped fluorophore (sulforhodamine B) (FIG. 3). The fluorescence emission of this dye is quenched at the high local concentrations of the liposome but upon membrane disruption and subsequent dilution, it strongly emits fluorescence at 585 nm. The INT domain fused to the N-terminal 34-114 or just the N-terminal 34-53 residues of pVI exhibited substantial membrane lytic activity over a time interval of seven minutes relative to complete release mediated by Triton X-100. The lytic activity of these pVI-INT fusion proteins was also similar to a purified synthetic peptide derived from pVI (pVI-syn, residues 34-54) that lacked the INT domain as well as the full length pVI molecule fused to INT (data not shown). These findings are consistent with previous pVI mutagenesis studies that show the predicted amphipathic a-helical domain (residues 34-53) of pVI is largely responsible for membrane insertion/disruption [18]. The current findings indicate that the membrane lytic domain of pVI retains membrane lytic activity even after fusion to the VPARP INT domain.

Example 3

Liposome Disruption with pVI-INT Vault Particles

Figure 4:
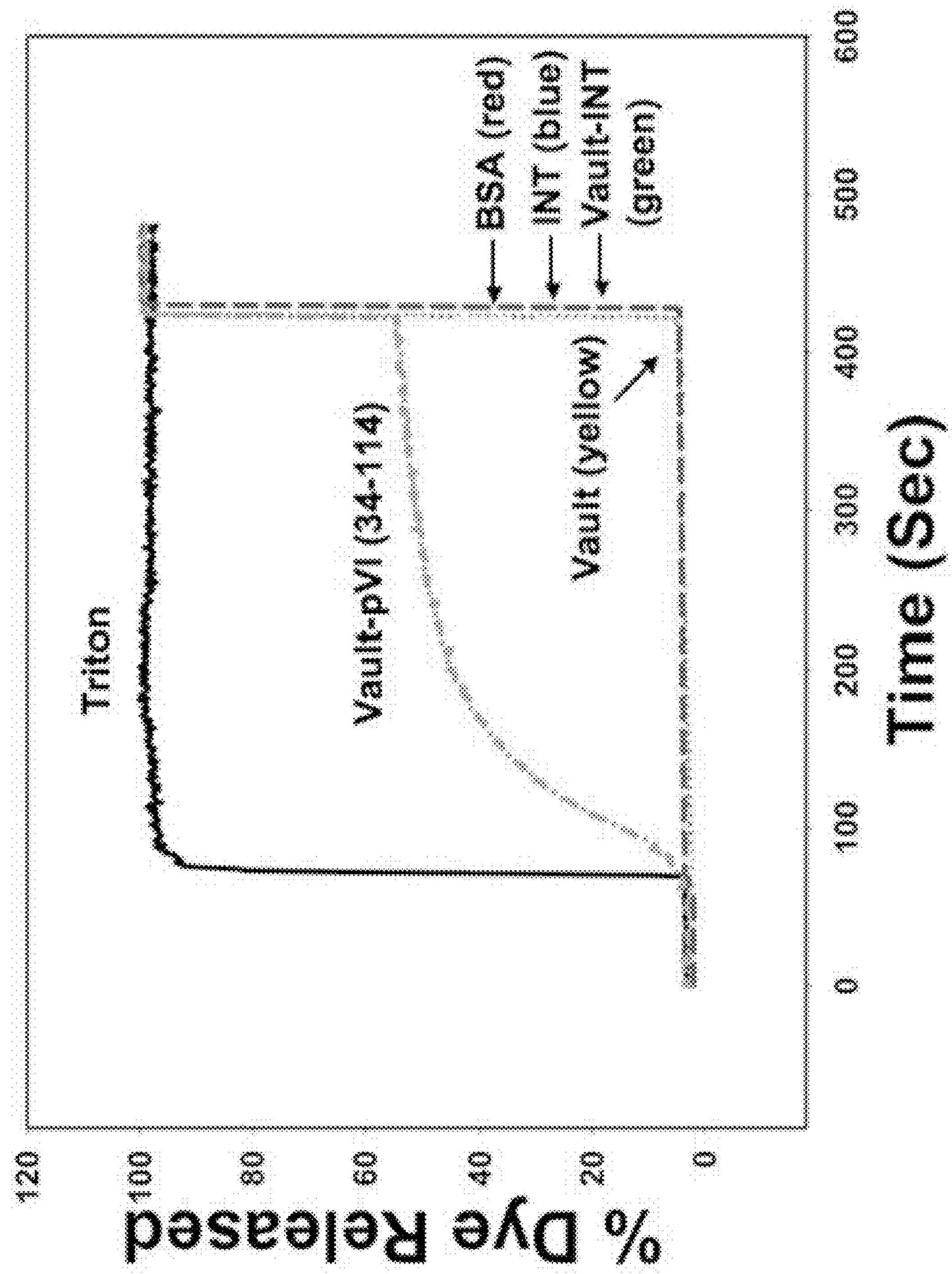
FIG. 4: Time course of liposome disruption by pVI-vaults. Liposomes were incubated for varying lengths of time at 37° C. with 137 μg of empty vault particles (yellow line), vaults containing INT alone (green), or pVI-INT (34-114) (magenta) to disrupt liposomes at 37° C. and the fluorescence emission was recorded as described above. For maximum dye release, triton X-100 was added at the same time (at 420 sec to each sample). Disruption by BSA (red) or INT (blue) alone were included as negative controls.

We sought to determine whether pVI-INT fusion proteins incorporated into recombinant vault particles were capable of mediating liposome disruption (FIG. 3). Vault particles alone showed negligible membrane lytic activity while vaults containing the INT domain exhibited a low level of membrane lysis that was not observed in every experiment. In contrast, vaults containing both the smaller pVI-INT (pVI residues 34-53) and the larger pVI (residues 34-114) fusion proteins caused substantial and consistent membrane disruption. These findings indicate that association of the membrane lytic domain of pVI with vault particles can facilitate membrane disruption. Unexpectedly however, we found that the smaller version of pVI (residues 34-53) was not as efficiently incorporated into vaults (data not shown) as the larger pVI domain (34-114) and therefore we employed the latter construct for additional kinetic and functional analyses. Vaults containing pVI (34-114) caused a rapid and progressive disruption of liposomes as a function of time with 50% maximum disruption occurring at ~2 minutes (FIG. 4). In contrast, empty vaults, the purified INT protein alone, vault-INT, or BSA caused little dye release over this time interval.

Example 4

Cellular Entry of pVI-INT Vault Particles

Figure 5:
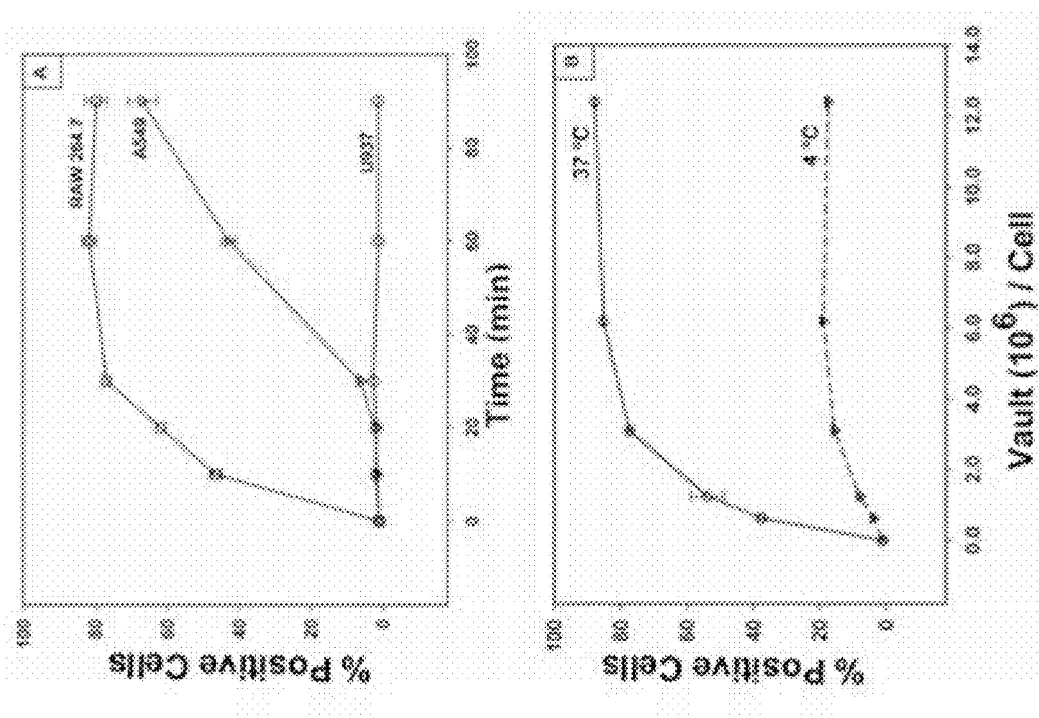
FIG. 5: Analysis of vault internalization into different mammalian cells. (a) Internalization of Cy3.5-labeled fluorescent vaults into different cell types at 37° C. was measured by flow cytometry. The cells were incubated with labeled vaults for various times at 37° C. prior to measuring uptake by flow cytometry in the presence of trypan blue dye to quench the fluorescence of uninternalized particles. (b) Internalization of Cy3.5-labeled vaults into RAW 264.7 cells was measured at 4° C. or 37° C.

We examined whether different cell types could support entry of Cy3-labeled vault (empty) particles (FIG. 5*a*). These studies used trypan blue dye to quench the fluorescence of externally bound vault particles while allowing detection of internalized vault particles. Murine macrophage RAW 264.7 cells exhibited rapid and substantial internalization of labeled vaults whereas human U937 monocytic cells did not readily support vault internalization. Human A549 epithelial cells also supported significant vault uptake; however, this occurred with slower kinetics than that of RAW 264.7 cells. Vault association with RAW 264.7 cells was also substantially greater at 37° C. than at 4° C. (FIG. 5*b*), indicating that the labeled vaults were undergoing internalization into cells rather than simply being bound to the cell surface.

Example 5 pVI-INT Assisted Entry of Selected Biomolecules Into RAW 264.7 Macrophages

Figure 6A:
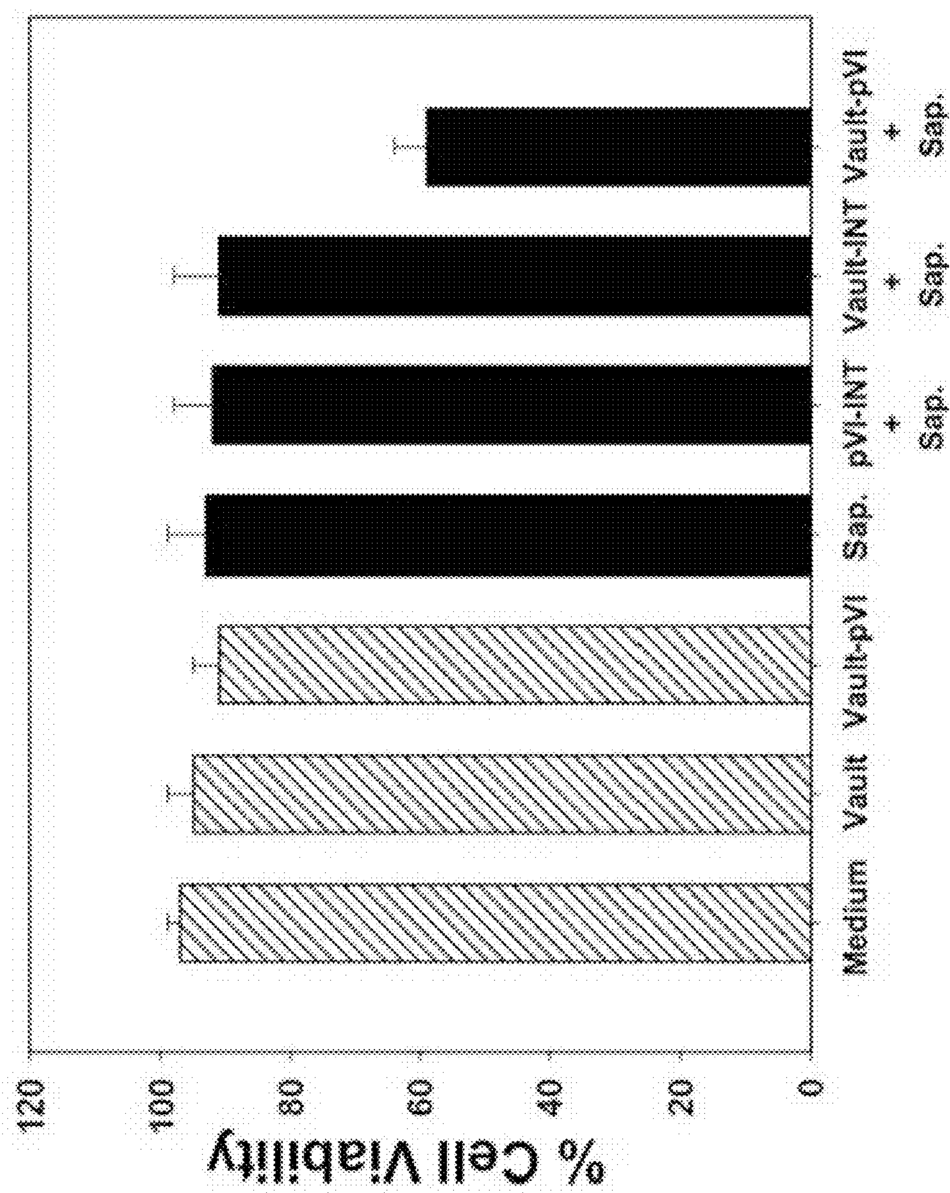
FIG. 6: Co-delivery of a ribotoxin (saporin) into cells via pVI-vault particles. (a) RAW 264.7 cells were incubated with 1 μg of the indicated amounts of pVI INT proteins or 137 μg of pVI-vault particles ($4.310\times10^9$/cell) in the presence (black bars) or absence (stripped bars) of 1.65×10-7 M saporin and cell viability was measured 48 hours later using the XTT assay. All values were normalized to untreated cells. (b) Dose response of cell killing by pVI-vaults ($4.310\times10^9$/cell) in the presence of saporin (open symbols) or with saporin only (closed symbols). Cytoxicity of RAW 264.7 cells was determined by XTT assay at 48 hours following addition of these reagents. (c) Dose response induction of cytotoxicity in RAW 264.7 cells. Cells were incubated with varying amounts of pVI-vaults (solid circles) or INT-vaults (open triangles) in the presence of $1.65\times10^{-7}$ M saporin for 4 hours prior to measuring viability by XTT.

We determined whether pVI-containing vault particles were capable of facilitating entry of selected biomolecules into RAW 264.7 macrophages (FIG. 6*a*). For these studies we assessed vault-mediated delivery of a soluble ribotoxin (saporin), that blocks host cell protein synthesis and therefore decreases cell viability upon entry into the cytoplasm. Saporin alone in the absence of membrane penetrating agents had little effect on cell viability, consistent with its inability to cross cell membranes. Cell viability was also unaffected by vault particles or vault-pVI complexes in the absence of saporin.

Figure 6B:
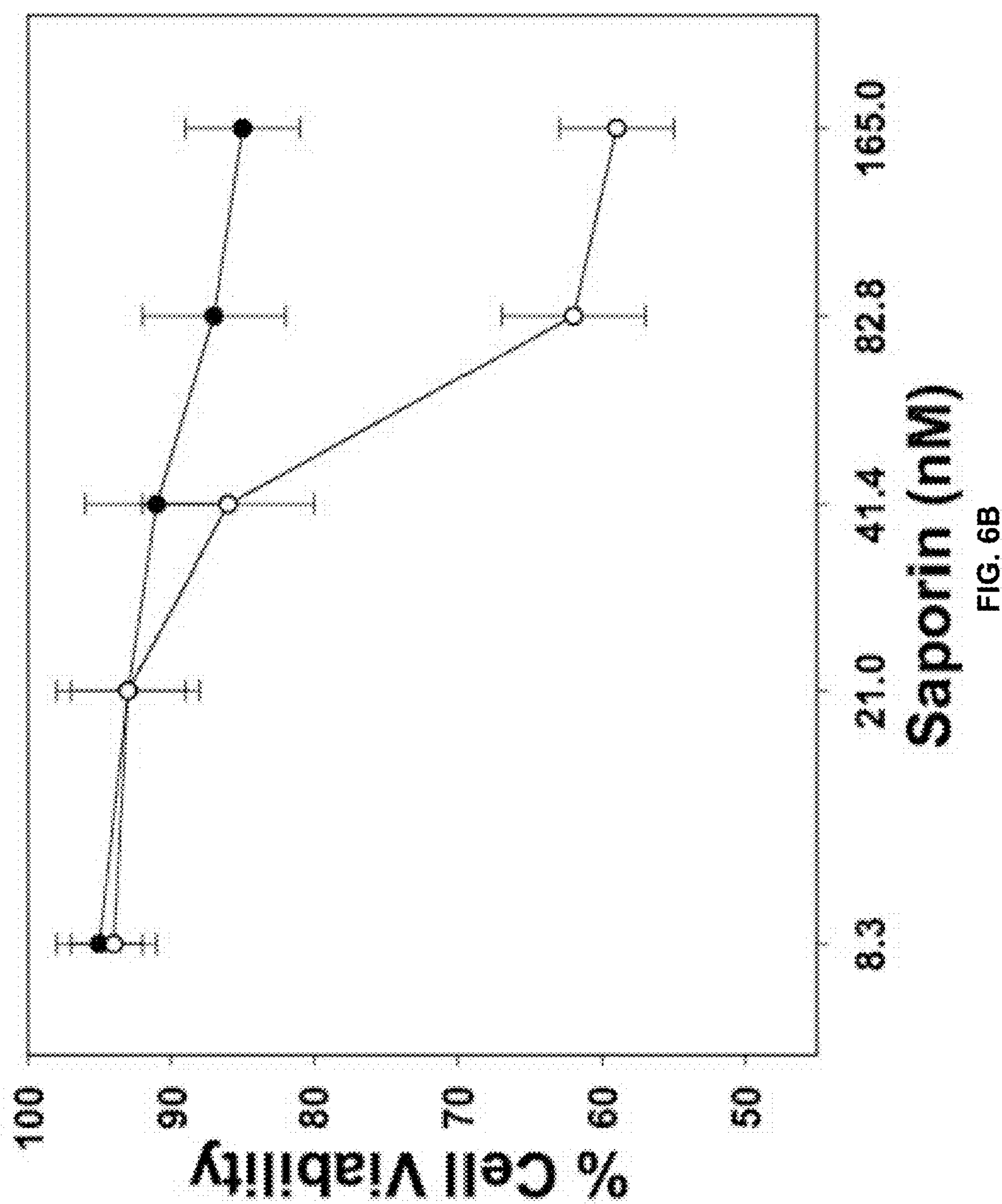
Figure 6C:
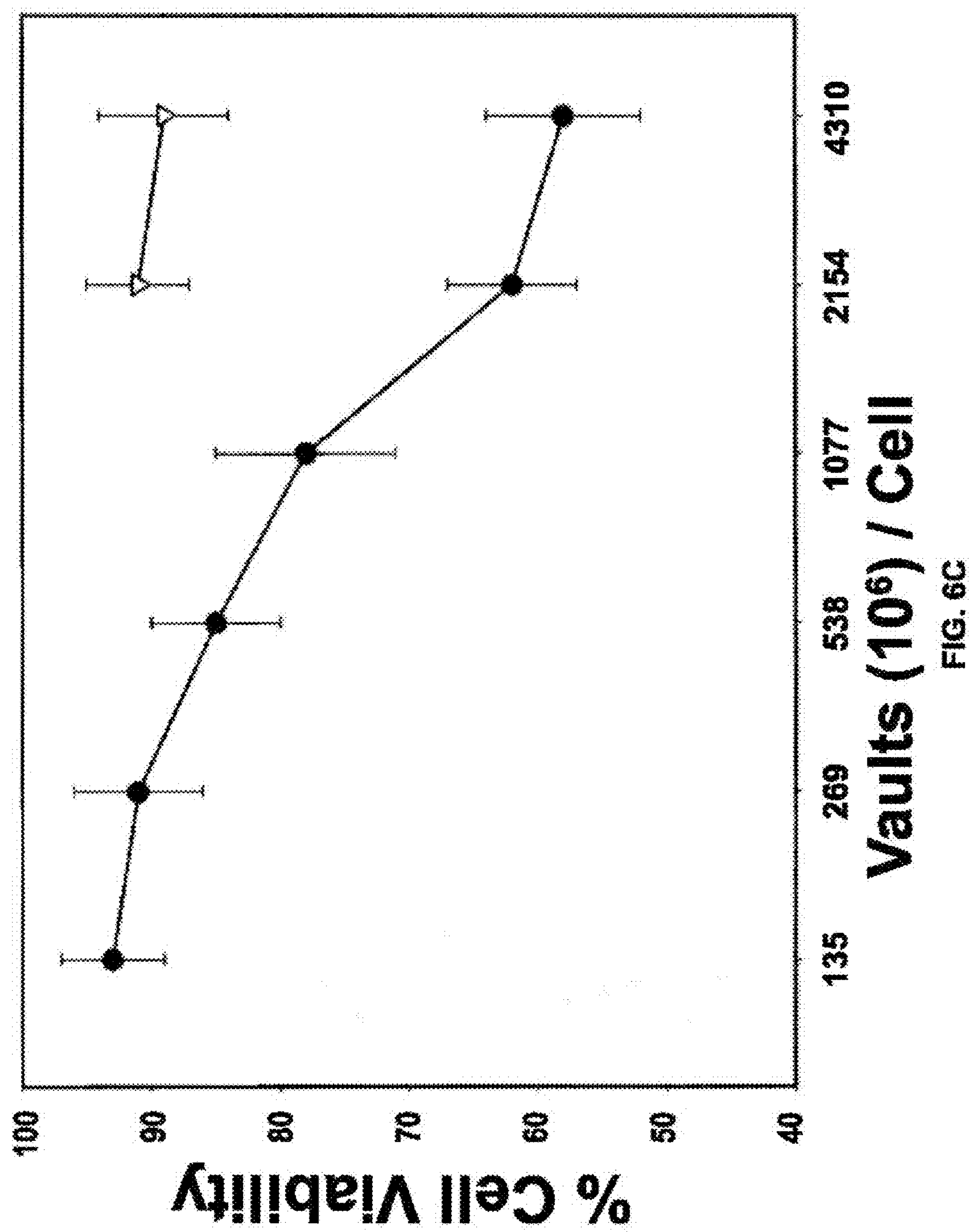

In contrast, vault-pVI (residues 34-114) in the presence of saporin caused a ~40% decrease in cell viability, consistent with significant endosomal membrane disruption by internalized particles. The decrease in cell viability mediated by vault-pVI particles was also directly proportional to the amount of saporin, with a threshold of 21 nM required to reveal RAW 264.7 cell toxicity (FIG. 6*b*). Cytotoxicity was also directly proportional to the amount of vault-pVI particles added per cell (FIG. 6*c*).

Example 6 pVI-INT Assisted Gene Transfer into RAW 264.7 Macrophages

Figure 7A:
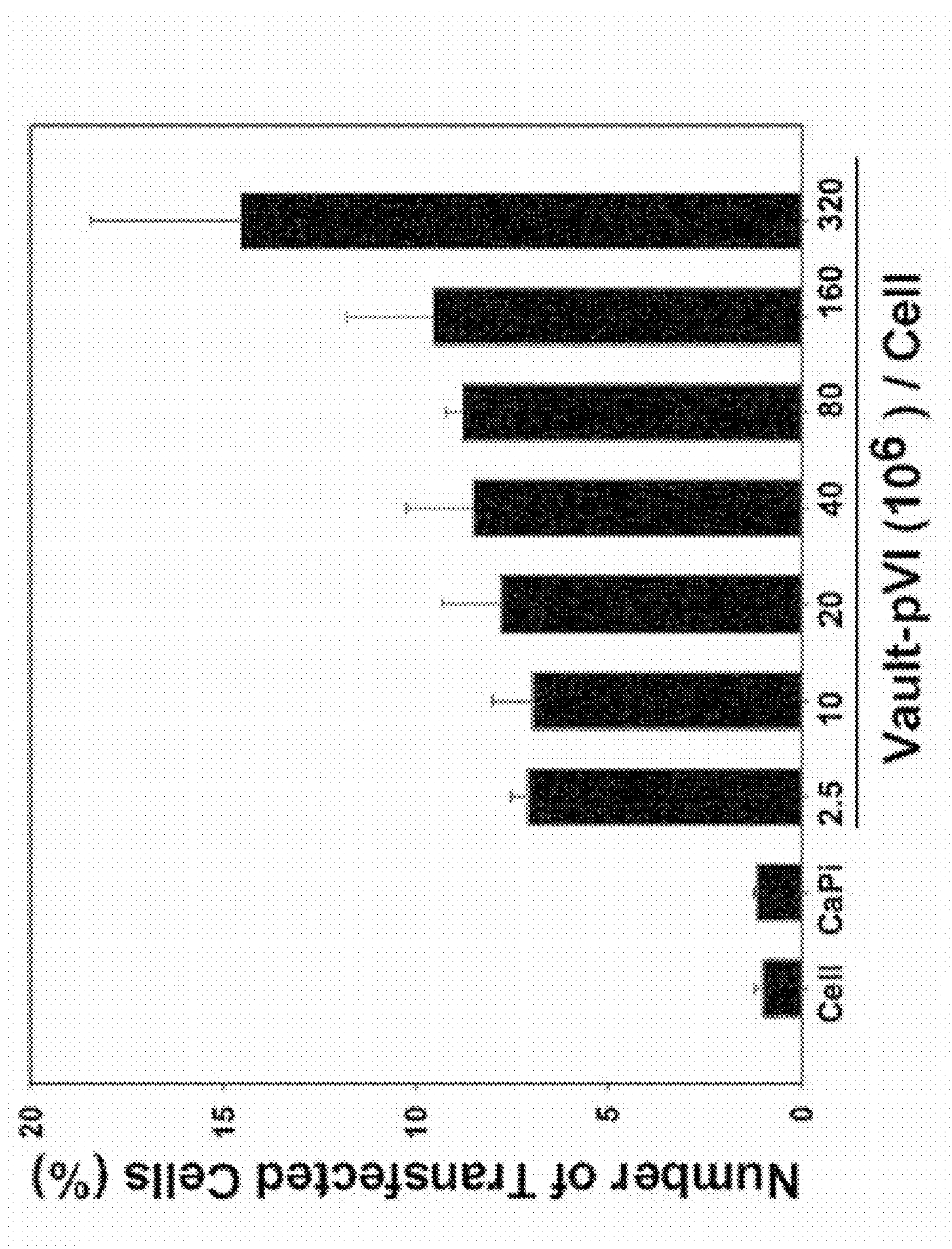
FIG. 7: Enhancement of DNA delivery via pVI-vault particles. Raw 264.7 cells were cultured in the presence of increasing numbers of pVI-vaults (a) or vault-INT particles (b) for 24 hours prior to measuring transgene expression by flow cytometry. For comparison, untransfected cells or cells incubated with calcium phosphate precipitated DNA (CaPi) alone were analyzed in parallel. The data shown are the average of triplicate samples and is representative of at least three experiments.
Figure 7B:
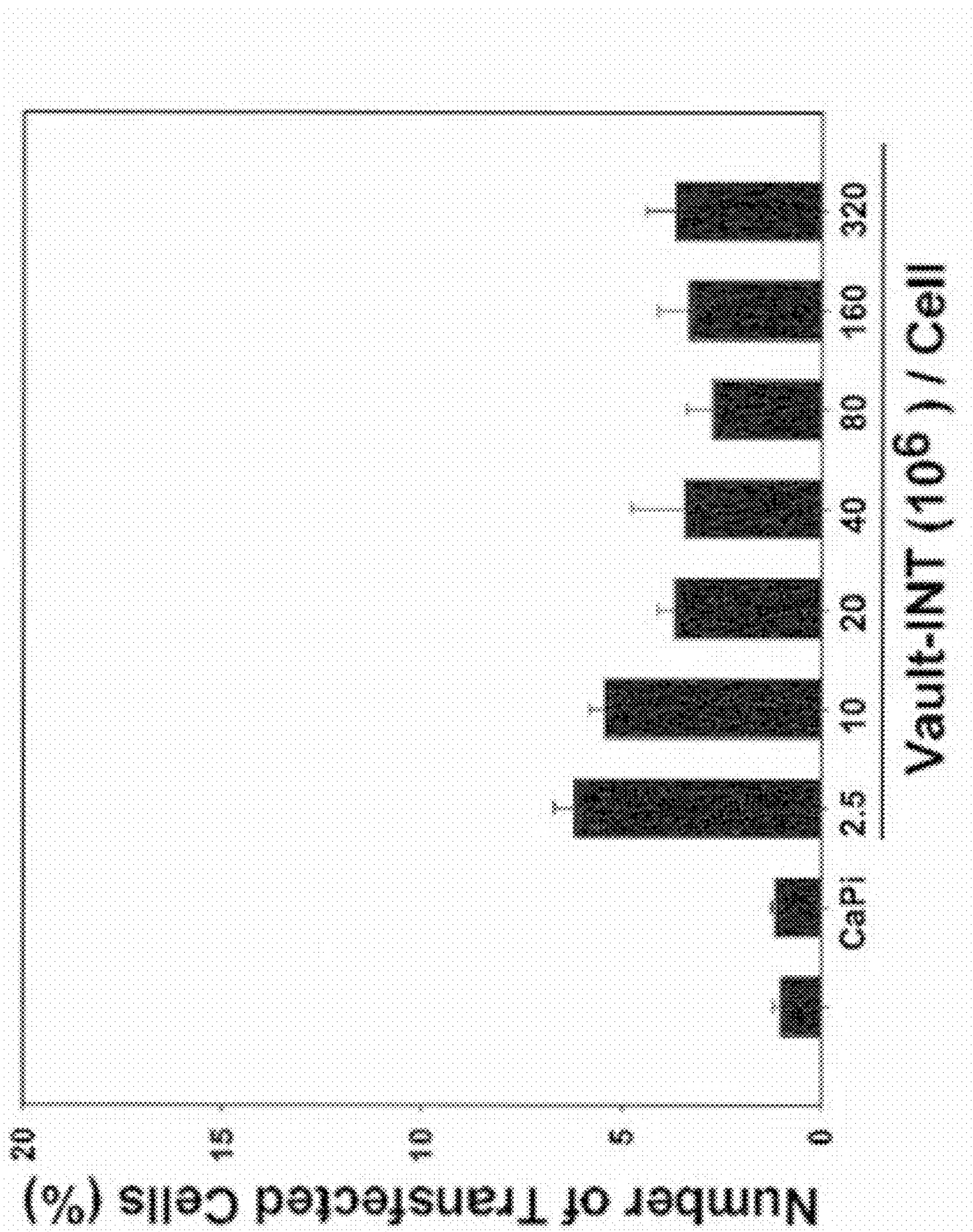

We examined whether pVI-vaults were capable of enhancing gene transfer to RAW 264.7 cells. For these studies, we assessed co-delivery of calcium phosphate precipitated eDNA plasmids encoding GFP (CaPi DNA) in the presence or absence of vaults (FIG. 7). Vault particles containing pVI enhanced delivery of GFP plasmid DNA, achieving a ~7-fold higher level of delivery at the highest dose than that observed with calcium phosphate precipitated DNA alone (FIG. 7*a*). In contrast, vaults containing INT alone conferred relatively low levels (~2-3 fold increase over CaPi alone) of gene transfer and this was independent of input dose (FIG. 7*b*). These findings indicate that vault-pVI particles are capable of stimulating the transfer of calcium-phosphate precipitated DNA into target cells.

Example 7

Co-Delivery of CaPi DNA by EGF/pVI-INT Vaults

Figure 8:
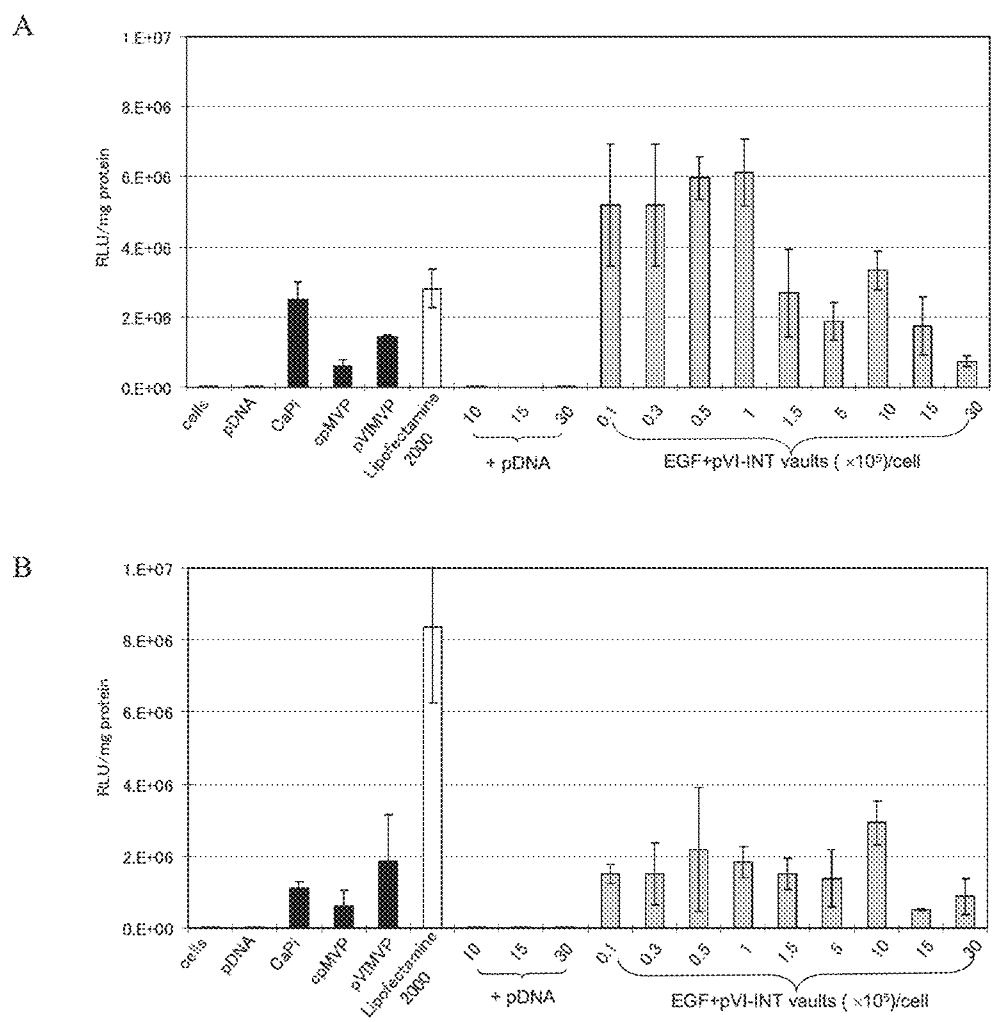
FIG. 8: Targeted co-delivery of calcium phosphate precipitated plasmid DNA (CaPi DNA) by EGF/pVI-INT vaults. (A) Delivery of CaPi DNA to A431 cells expressing more than 106 of EGFR on the cell surfaces. (B) Delivery of CaPi DNA to HeLa cells expressing low numbers of EGFR. Control included: plasmid DNA only, CaPi DNA only, CaPi DNA with $10\times10^{5}$ CP- or pVI-MVP vaults/cell (0.8 μg of CaPi DNA/well), Lipofectamine 2000, and EGF/pVI-INT vaults with plasmid DNA.

As reported previously, vault particles packaged with pVI-INT were able to facilitate delivery of calcium phosphate precipitated plasmid DNA (CaPi DNA) to RAW cells. [35]We also have shown that vaults engineered to display EGF (MVP-EGF vaults) on their external surface can specifically bind to EGFR on A431 cells. [30]To determine whether targeting the vaults would enhance plasmid transfection, the pVI-INT fusion protein was packaged into the lumen of MVP-EGF vaults pVI-INT/MVP-EGF vaults). We used HeLa and A431 epithelial cell lines expressing different numbers of EGFR on their cell surfaces to evaluate the ability of these vaults to facilitate plasmid transfection (FIG. 1). These vault particles showed an increase in transfection activity that exceeded that of Lipofectamine 2000 and CaPi DNA when targeted to EGFR (compare FIGS. 8A and 8B). The highest level of targeted transfection efficiency was seen with 0.1-1× $10^5$ vaults/cell in A431 cells (FIG. 1A). Higher numbers of pVI-INT/MVP-EGF vaults induced lower transfection efficiencies probably due to the toxicity of the pVI protein. When HeLa cells were examined, the transfection efficiency of this vault structure was lower than Lipofectamine 2000 (FIG. 1B). As HeLa cells display many fewer copies of EGFR than A431 cells, this result indicates that the high transfection efficiency of pVI-INT/MVP-EGF vaults in A431 cells resulted from facilitated co-delivery of CaPi DNA to the cells mediated through the ligand-receptor protein interaction.

Example 8

An Alternative pVI Vault Design

Although packaging pVI-INT inside of vaults has been shown to co-deliver various biomolecules, it would be advantageous to develop a particle where the pVI domain is directly attached to the vault particle, leaving the lumen of the particle empty so that additional biomolecules can be packaged inside of these vaults. Towards that goal, we fused a 20 aa lytic peptide derived from pVI (aa 34 to 54) directly onto the N-terminus of MVP (to form pVI-MVP vaults). In these vaults, the pVI would be localized at the waist of the vault particle where other N-terminal tags have been previously shown to localize. [26] Importantly, the INT binding domain on MVP, located above and below the waist of the vault, would be available for binding of additional cargo into these vaults, to add another functional dimension.

Figure 9:
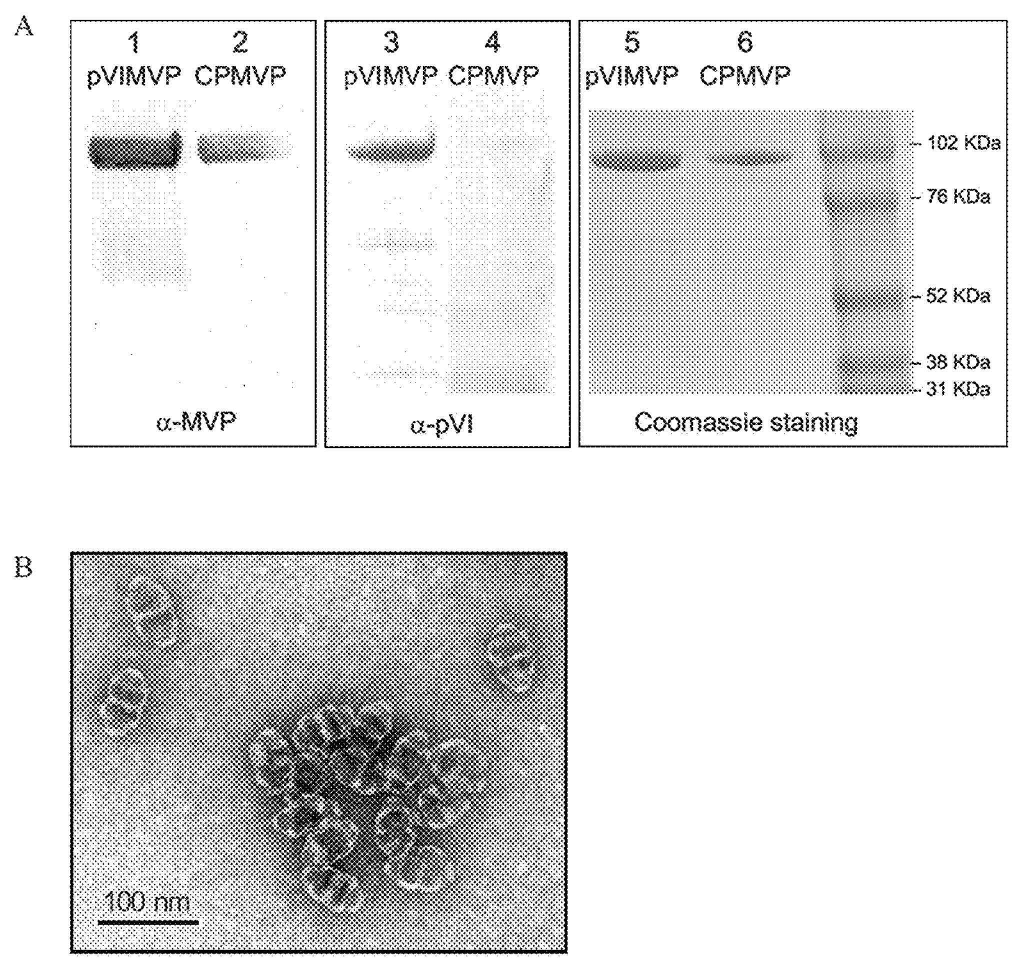
FIG. 9: Analysis of pVI-MVP recombinant vaults. (A) Purified pVI-MVP vaults (lanes 1, 3 and 5) and CP-MVP vaults (lanes 2, 4 and 6) were fractionated by SDS-PAGE and analyzed by Western blot (lanes 1-4) or stained with Coomassie (lanes 5 and 6). The blot from lanes 1 and 2 was probed with an anti-MVP polyclonal antibody, and the blot from lanes 3 and 4 was probed with an anti-pVI polyclonal antibody to confirm the presence of the pVI tag. (B) Negative stain TEM image of pVI-MVP

Expression of pVI-MVP vaults was compared with CP-MVP vaults in Sf9 insect cells. Vaults which self-assembled from these expressed proteins were purified and analyzed by SDS PAGE (FIG. 9A). Gels were either stained with Coomassie (FIG. 9A, lanes 5 and 6) or immunoblotted with an anti-MVP antibody (FIG. 9A, lanes 1 and 2) or with an anti-pVI antibody (FIG. 9A, lanes 3 and 4). The results of the Coomassie stained SDS-PAGE confirmed that pVI-MVP vaults were formed in Sf9 insect cells. The presence of the pVI fused to the N-terminus of MVP (~99 KDa) is clearly shown by immunoblotting with an anti-MVP antibody (FIG. 9A, lane 1) and an anti-pVI antibody (FIG. 9A, lane 3). Most vault purifications are carried out using 75 mM NaCl, however the pVI-MVP vault structure was sensitive to salt concentration resulting in formation of some half vault aggregates, previously described as vaultimers. [31] These aggregates could be mostly eliminated when vaults were purified using a salt concentration of 25 mM. These purified pVI-MVP vaults were examined by negative stain transmission electron microscopy (FIG. 9B). The particles observed had the typical morphology of previously published intact mono-dispersed vault particles. [31]

Example 9

Co-Delivery of Ribotoxin by pVI-MVP Vaults

Figure 10:
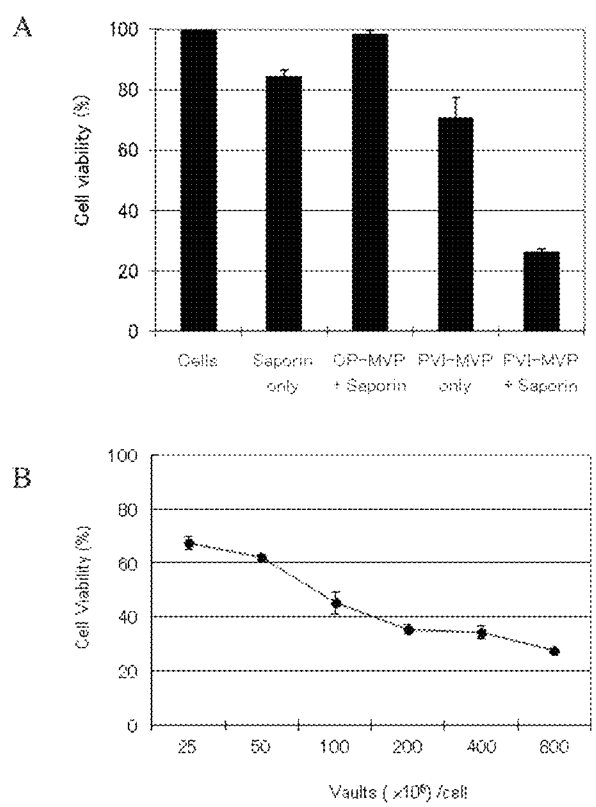
FIG. 10: Enhanced delivery of saporin to the cytosol of RAW 264.7 cells with pVI-MVP vaults. Cell viability was examined using an MTT assay. (A) Effect of pVI-MVP ($800\times10^{6}$ particles/cell) on cell viability in the presence and absence of saporin ($1.65\times10^{-7}$ M). Control included : Saporin only, Saporin with CP-MVP ($800\times10^{6}$ particles/cell), and pVI-MVP ($800\times10^{6}$ particles/cell) only. (B) pVI-MVP vault concentration dependence of the cell viability. Increasing concentration of vaults, as indicated, was added to cells in the presence of saporin ($1.65\times10^{-7}$M) and the viability was examined.

We tested whether pVI-MVP vault particles were able to facilitate the delivery of co-internalized biomolecules into the cytosol of mouse macrophage RAW 264.7 cells (FIG. 10). For this study, we used a soluble ribotoxin, saporin. Entry of saporin into the cytoplasm results in inhibition of protein synthesis and decrease in cell viability. Saporin alone has low cell toxicity due to its inability to cross the cell membrane (FIG. 10A). Control vaults (CP-MVP) are also non-toxic, while pVI-MVP vaults at high concentrations decreased cell viability by up to 30%. When pVI-MVP vaults were added to cells in the presence of saporin, a substantially greater cytotoxicity (70% decrease) was observed due to a bystander effect explained by the pVI-mediated lysis of the endosomal membrane and subsequent release of co-internalized saporin. Co-delivery of the ribotoxin by pVI-MVP vaults was also dose-dependent as indicated by studies shown in FIG. 10B.

Example 10

Co-Delivery of CaPi by pVI-MVP Vaults to RAW Cells

Figure 11:
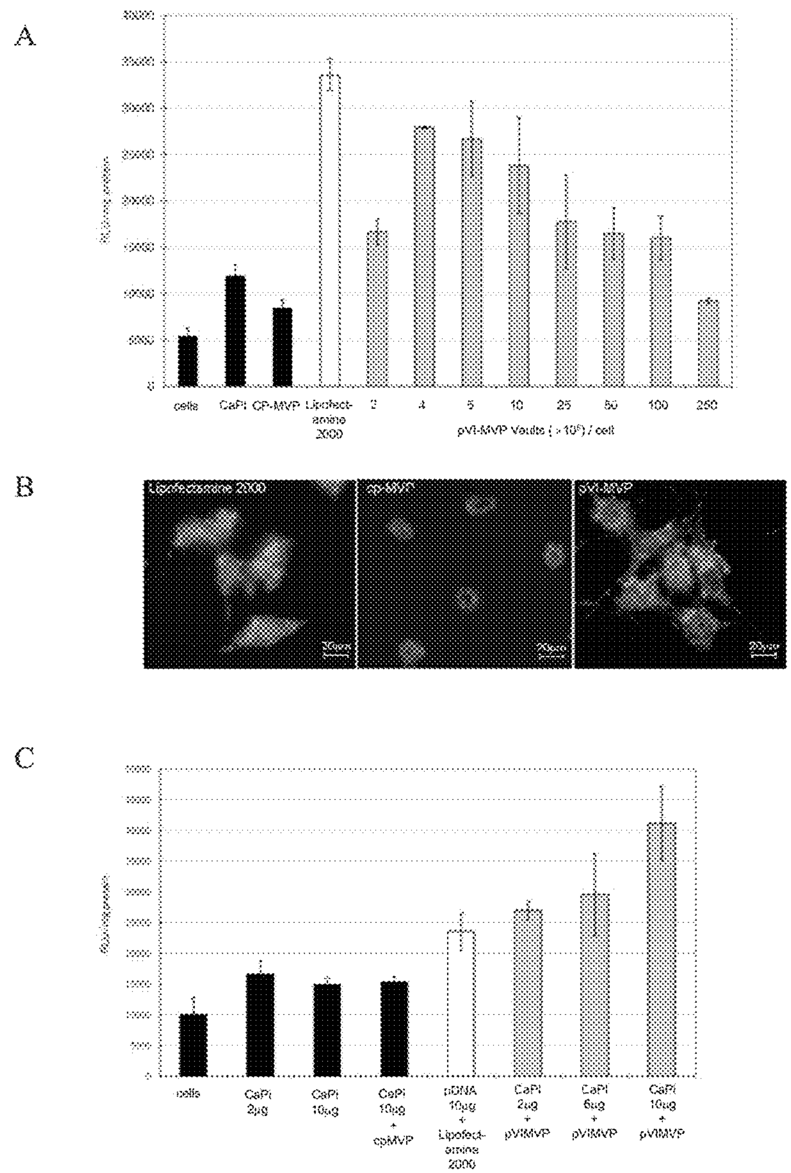
FIG. 11: Facilitated co-delivery of CaPi DNA by pVI-MVP vaults. (A) Transfection by various amounts of pVI-MVP vaults to RAW cells (2 μg of CaPi DNA/well). Controls included: CaPi DNA alone, CaPi DNA with CP-MVP vaults ($250\times10^{5}$ vaults/cell), and Lipofectamine 2000. (B) Expression of GL proteins (green) in RAW cells by pVI-MVP vaults ($4\times10^{5}$ pVI-MVPvaults/cell, 2 μg of CaPi DNA), Lipofectamine 2000 and CP-MVP ($250\times10^{5}$ CP-MVP/cell, 2 μg of CaPi DNA). The nuclei were stained with Hoechst (blue). (C) Enhanced transfection efficiency of pVI-MVP particles with high amount of CaPi DNA.

The co-delivery of CaPi DNA by pVI-MVP vaults into 264.7 RAW cells was evaluated as shown in FIG. 11. For these studies, we assessed delivery of CaPi DNA encoding luciferase in the presence or absence of pVI-MVP vaults. The vault particles containing pVI enhanced delivery of CaPi DNA compared to the addition of CaPi DNA alone or vault particles that did not contain the pVI (FIG. 11A). Optimal delivery occurred using 4 –10×$10^5$ pVI-MVP vaults per cell. When higher numbers of pVI-MVP vaults and/or CaPi DNA were used, lower transfection efficiencies were observed probably due to pVI toxicity. However, pVI-MVP vaults still showed improved transfection efficiencies over CaPi DNA in the range of less than 2×$10^5$ vaults per cell. To visualize the functionality of pVI-MVP vaults, we examined RAW 264.7 cells transfected with Lipofectamine 2000, CP-MVP vaults, and pVI-MVP vaults (FIG. 11B). Using a higher DNA concentration (10 μg vs 2 μg) pVI-MVP vaults displayed higher transfection efficiencies than CaPi DNA or Lipofectamine 2000 (FIG. 11C). Here the lower transfection efficiency of Lipofectamine was due to the increased cytotoxicity, while pVI-MVP vaults still showed high transfection efficiencies even considering the toxicity induced by CaPi DNA. Overall we observed lower cytotoxicity of pVI-MVP vaults compared to the commercial Lipofectamine transfection agent under optimized conditions. The enhanced delivery of biomolecules by pVI-MVP vaults is likely due to the high numbers of pVI fused to MVPs. We estimated that only 20 to 30 pVI were conjugated to one vault particle when the INT targeting domain was used [35] while the conjugation of pVI directly to the N-terminus of MVP provided 78 or more pVI-peptides per vault.

Example 11

Disruption of Endosomes by pVI-MVP in RAW Cells

Figure 12:
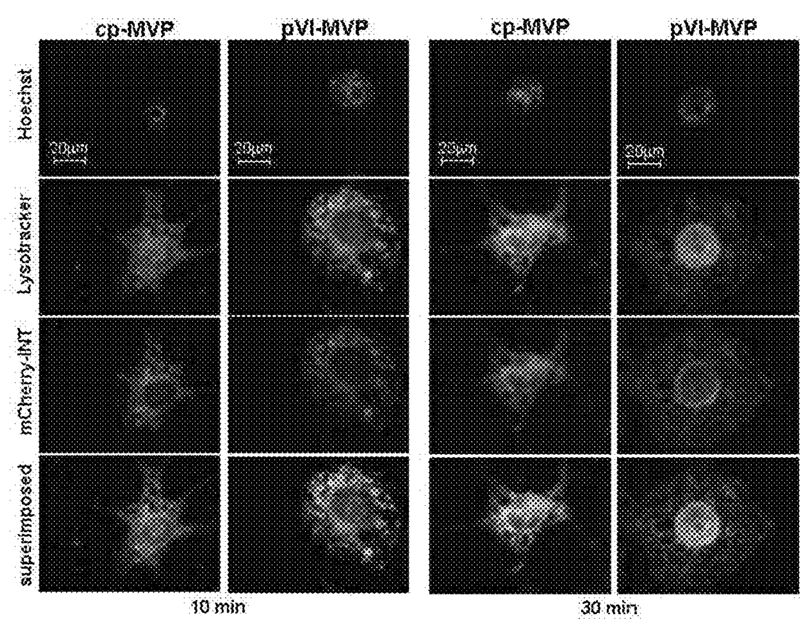
FIG. 12: Swelling and disruption of endosomal/lysosomal membrane by pVI-MVP vaults in RAW cells. Endocytosis of CP-MVP at the identical time points was shown as controls. The nuclei were stained with Hoechst (blue). The lysosomes were stained with Lysotracker (green). The observed red fluorescence is the intrinsic fluorescence from the mCherry protein packaged inside of the vaults.

We examined internalization of pVI-MVP vaults in RAW 264.7 cells by packaging the particles with the red fluorescent, mCherry-INT fusion protein (FIG. 12). Vault particles without pVI (CP-MVP/mCherry-INT vaults) were colocalized with Lysotracker (green) as indicated by punctate fluorescence at 10 and 30 minutes following cellular uptake. This pattern was quite different when vaults containing the pVI were examined. A distinct endosomal/lysosomal swelling occurred as early as 10 min after pVI-MVP vaults were added (FIG. 12). Strikingly, thirty minutes after uptake of pVI vaults, the Lysotracker staining revealed few if any punctate vesicles which indicated severe disruption of endosome/lysosomes by the pVI proteins which is consistent with their likely disruption via the established membrane lytic activity of pVI. [33] In addition, cells incubated with pVI vaults showed morphological changes including swelling and spread of cytosol as observed many during the macrophage's response to bacterial infection. [34, 35] Although quite dramatic, the cells recovered from these morphological changes and remained viable as indicated by the transfection results (FIG. 11B) which were evaluated after 72 h.

Example 12

Multifunctional Recombinant Vaults

With the goal of developing a bifunctional vector that can both target surface receptors and enhance cytosomal release, we designed vault particles combining two functional motifs. Despite the enhanced co-delivery of CaPi DNA facilitated by EGF vaults, those vaults have been shown to stimulate receptor phosphorylation and downstream events such as proliferation. [36,37] To evaluate targeting and facilitated delivery without affecting cell division, we turned to vaults engineered to display the IgG binding, Z domain, on their external surface. [29] Rather than packaging these vaults with the pVI-INT protein, we utilized the strategy described above where a 20 aa lytic peptide derived from pVI is fused to the N-terminus of MVP (to form pVI-MVP-Z vaults)

Figure 13:
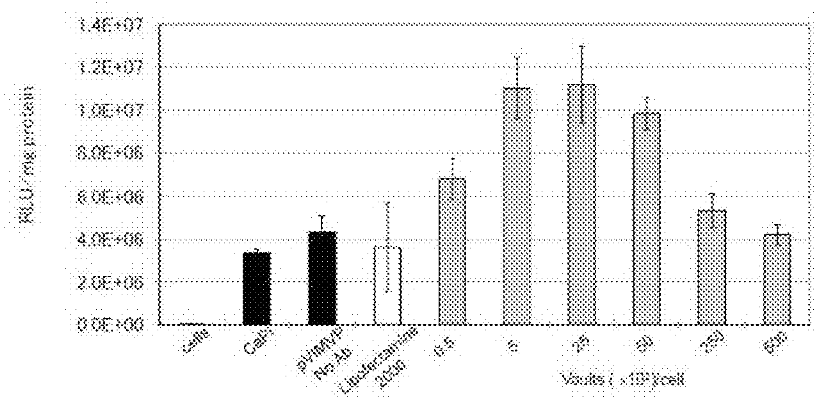
FIG. 13: Transfection efficiencies of pVI-MVP-z and anti-EGFR antibody complexes to A431 cells (1.5 μg of CaPi DNA/well). Control included: CaPi DNA only, pVI-MVP ($500\times10_{2}$ vaults/cell) without antibody, and Lipofectamine 2000.

As shown previously, [29] CP-MVP-Z vaults incubated with anti-EGFR showed high specific binding to A431 cells. We next tested the transfection efficiency of pVI-MVP-Z vaults (FIG. 13). The pVI-MVP-Z vaults were incubated with anti-EGFR antibody overnight at 4° C. to allow binding of antibodies to the Z domain. Antibody bound vaults were incubated with serum starved A431 cells at 4° C. for 1 h to allow surface binding, and the cells were washed to remove unbound complexes prior to the addition of CaPi DNA to the culture media and warming to 37° C. Interestingly, the highest transfection efficiencies that we observed among all the structures tested in this study (pVI-MVP, EGF/pVI-INT, CP-MVP, and pVI-MVP-z), were seen with this engineered vault. As seen in FIG. 13, only 500 pVI-MVP-z vault particles were required to facilitate plasmid expression per cell. As few as 50 pVI-MVP-Z+EGFR mAb vaults per cell achieved greater transfection than Lipofectamine 2000. Furthermore the Lipofectamine 2000 showed high toxicity in this cell line while little or no toxicity was observed with the pVI-MVP-Z+ EGFR mAb vault complexes. This result implies that the targeted vaults are efficiently taken up by the A431 cells where they disrupt endosome/lysosome allowing the co-delivery of CaPi DNA into the cytoplasm where it can presumably be transported to the nucleus for expression. The enhanced uptake of vaults was facilitated by the greater binding between the pVI-MVP-Z+EGFR mAb vaults and the receptors on these cells. The specificity of this process was further demonstrated by pre-incubating A431 cells with free EGFR mAB which significantly blocked the binding of anti EGFR-bound vaults to the cells (not shown).

Example 13

Release of Packaged Protein to Cytosol by pVI-MVP-Z Vaults

Figure 14:
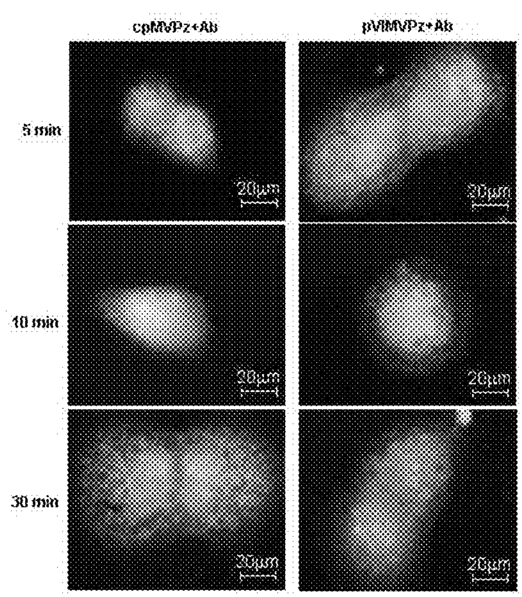
FIG. 14: The enhanced release of vault nanoparticles to cytosol of A431 cells by pVI proteins. The superimposed images were shown. The nuclei were stained with Hoechst (blue). The colocalization of lysosome (Lysotracker with green fluorescence) and vault particles (intrinsic red fluorescence from the mCherry protein packaged inside of the vaults) was shown as yellow.

We observed the endocytosis of antibody bound pVI-MVP-Z vaults in A431 cells by tracking red fluorescent mCherry-INT protein packaged into these particles. The immediate escape of these vaults was observed in areas surrounding the outer rim of cells in less than 5 min after vault addition (FIG. 14). This result is consistent with our previous studies which indicated that vaults containing pVI caused a rapid and progressive disruption of liposomes within ~2 min. [32] We assumed that the instantaneous interaction between pVI and the endosomal membranes occurred shortly after formation of the endosomal/lysosomal compartment. In 30 min, vaults were already released from endosome/lysosomes and located independently within the cytoplasm as shown by the red staining in in FIG. 14, while vault particles without pVI proteins were still trapped in Lysotracker-positive compartments.

Taken together these results show that vaults can be engineered as multifunctional non-toxic delivery vehicles that can be targeted to bind cell-specific receptors, enter via endocytosis and efficiently lyse endosomal membranes to deliver a packaged payload to the cell cytoplasm. These particles have the potential to be used for targeted delivery of therapeutics.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

TABLE 1

| Sequences |
|---|
| pVI Protein sequence (Genbank# AAW65513.1) |
| SEQ ID NO: 1 |
| MEDINFASLAPRHGSRPFMGNWQDIGTSNMSGGAFSWGSLWSGIKNFGSTVKNYGSKAWNSSTGQM |
| LRDKLKEQNFQQKVVDGLASGISGVVDLANQAVQNKINSKLDPRPPVEEPPPAVETVSPEGRGEKR |
| PRPDREETLVTQIDEPPSYEEALKQGLPTTRPIAPMATGVLGQHTPVTLDLPPPADTQQKPVLPGP |
| TAVVVTRPSRASLRRAASGPRSLRPVASGNWQSTLNSIVGLGVQSLKRRRCF |
| pVI lytic peptide (aa 34-53) nucleotide sequence |

TABLE 1-continued

| Sequences | |
|---|---|
| GCC TTC AGC TGG GGC TCG CTG TGG AGC GGC ATT AAA AAT TTC GGT TCC ACC GTT AAG AAC | SEQ ID NO: 2 |
| pVI lytic peptide (aa 34-53) protein sequence | |
| AFSWGSLWSGIKNFGSTVKN | SEQ ID NO: 3 |
| pVI lytic peptide (aa 34-114) nucleotide sequence | |
| AFSWGSLWSGIKNFGSTVKNYGSKAWNSSTGQMLRDKLKEQNFQQKVVDGLASGISGVVDLANQAV QNKINSKLDPRPPVE | SEQ ID NO: 4 |
| mINT DNA sequence | |
| TGC ACA CAA CAC TGG CAG GAT GCT GTG CCT TGG ACA GAA CTC CTC AGT CTA CAG ACA GAG GAT GGC TTC TGG AAA CTT ACA CCA GAA CTG GGA CTT ATA TTA AAT CTT AAT ACA AAT GGT TTG CAC AGC TTT CTT AAA CAA AAA GGC ATT CAA TCT CTA GGT GTA AAA GGA AGA GAA TGT CTC CTG GAC CTA ATT GCC ACA ATG CTG GTA CTA CAG TTT ATT CGC ACC AGG TTG GAA AAA GAG GGA ATA GTG TTC AAA TCA CTG ATG AAA ATG GAT GAC CCT TCT ATT TCC AGG AAT ATT CCC TGG GCT TTT GAG GCA ATA AAG CAA GCA AGT GAA TGG GTA AGA AGA ACT GAA GGA CAG TAC CCA TCT ATC TGC CCA CGG CTT GAA CTG GGG AAC GAC TGG GAC TCT GCC ACC AAG CAG TTG CTG GGA CTC CAG CCC ATA AGC ACT GTG TCC CCT CTT CAT AGA GTC CTC CAT TAC AGT CAA GGC TAA | SEQ ID NO: 5 |
| mINT protein sequence (residues 1563-1724 of the human VPARP protein sequence) | |
| CTQHWQDAVPWTELLSLQTEDGFWKLTPELGLILNLNTNGLHSFLKQKGIQSLGVKGRECLLDLIA TMLVLQFIRTRLEKEGIVFKSLMKMDDPSISRNIPWAFEAIKQASEWVRRTEGQYPSICPRLELGN DWDSATKQLLGLQPISTVSPLHRVLHYSQG | SEQ ID NO: 6 |
| pVI(aa 34-53)-MVP nucleotide sequence | |
| AANNNGNATTTTACTGTTTTCGTACAGTTTTGTAATAAAAAAACCTATAAATATTCCGGATTATTC ATACCGTCCCACCATCGGGCGCGGATCCCGGTCCGAAGCGCGCGGAATTCGCGGCCGCGTCGACTG TGGCTTGCAGCTGCCAGCTACCCTGCTAAATGTTTGGTGGGAAAAGCTTGGGATTCACCATG**GCCT TCAGCTGGGGCTCGCTGTGGAGCGGCATTAAAAATTTCGGTTCCACCGTTAAGAAC**GGCCTGGTGC CGCGCGGCAGCGCCATGGCAACTGAAGAGGCCATCATCCGCATCCCCCCATACCACTACATCCATG TGCTGGACCAGAACAGTAATGTGTCCCGTGTGGAGGTTGGACCAAAGACCTACATCCGGCAGGACA ATGAGAGGGTACTGTTTGCCCCAGTTCGCATGGTGACCGTCCCCCCACGCCACTACTGCATAGTGG CCAACCCTGTGTCCCGGGACACCCAGAGTTCTGTGTTATTTGACATCACAGGACAAGTCCGACTCC GGCACGCTGACCAGGAGATCCGACTAGCCCAGGACCCCTTCCCCCTGTATCCAGGGGAGGTGCTGG AAAAGGACATCACCCCACTGCAGGTGGTTCTGCCCAACACAGCACTGCATCTTAAGGCGTTGCTGG ACTTTGAGGATAAGAATGGAGACAAGGTCATGGCAGGAGACGAGTGGCTATTTGAGGGACCTGGCA CCTACATCCCACAGAAGGAAGTGGAAGTCGTGGAGATCATTCAGGCCACAGTCATCAAACAGAACC | SEQ ID NO: 8 |

TABLE 1-continued

| Sequences |
|---|
| AAGCACTGCGGCTAAGGGCCCGAAAGGAGTGCTTTGACCGGGAGGGCAAGGGGCGCGTGACAGGTG |
| AGGAGTGGCTGGTCCGATCCGTGGGGGCTTACCTCCCAGCTGTCTTTGAAGAGGTGCTGGATCTGG |
| TGGATGCTGTGATCCTTACAGAAAAGACTGCCCTGCACCTCCGGGCTCTGCAGAACTTCAGGGACC |
| TTCGGGGAGTGCTCCACCGCACCGGGGAGGAATGGTTAGTGACAGTGCAGGACACAGAAGCCCATG |
| TTCCAGATGTCTATGAGGAGGTGCTTGGGGTAGTACCCATCACCACCCTGGGACCTCGACACTACT |
| GTGTCATTCTTGACCCAATGGGACCAGACGGCAAGAACCAGCTGGGACAAAAGCGTGTTGTCAAGG |
| GAGAGAAGTCCTTTTTCCTCCAGCCAGGAGAGAGGCTGGAGCGAGGCATCCAGGATGTGTATGTGC |
| TGTCAGAGCAGCAGGGGCTGCTACTGAAGGCACTGCAGCCCCTGGAGGAGGGAGAGAGCGAGGAGA |
| AGGTCTCCCATCAGGCCGGAGACTGCTGGCTCATCCGTGGGCCCCTGGAGTATGTGCCATCTGCAA |
| AAGTGGAGGTGGTGGAGGAGCGTCAGGCTATCCCTCTGGACCAAAATGAGGGCATCTATGTGCAGG |
| ATGTCAAGACGGGGAAGGTGCGGGCTGTGATTGGAAGCACCTACATGCTGACTCAGGATGAAGTCC |
| TGTGGGAAAAGGAGCTGCCTTCTGGGGTGGAGGAGCTGCTGAACTTGGGGCATGACCCTCTGGCAG |
| ACAGGGGTCAGAAGGGCACAGCCAAGCCCCTTCAGCCCTCAGCTCCAAGGAACAAGACCCGAGTGG |
| TCAGCTACCGTGTCCCGCACAATGCAGCGGTGCAGGTCTATGACTACAGAGCCAAGAGAGCCCGTG |
| TGGTCTTTGGGCCCGAGCTAGTGACACTGGATCCTGAGGAGCAGTTCACAGTATTGTCCCTTTCTG |
| CCGGGCGACCCAAGCGTCCTCATGCCCGCCGTGCACTCTGCCTACTGCTGGGACCTGATTTCTTTA |
| CTGATGTCATCACCATCGAAACTGCAGATCATGCCAGGTTGCAGCTGCAGCTTGCCTACAACTGGC |
| ACTTTGAACTGAAGAACCGGAATGACCCTGCAGAGGCAGCCAAGCTTTTCTCCGTGCCTGACTTCG |
| TGGGTGACGCCTGCAAGGCCATTGCATCCCGAGTCCGGGGGGCTGTAGCCTCTGTCACCTTTGATG |
| ACTTCCATAAAAACTCAGCCCGGATCATTCGAATGGCTGTTTTTGGCTTTGAGATGTCTGAAGACA |
| CAGGTCCTGATGGCACACTCCTGCCCAAGGCTCGAGACCAGGCAGTCTTTCCCCAAAACGGGCTGG |
| TAGTCAGCAGTGTGGATGTGCAGTCAGTGGAGCCCGTGGACCAGAGGACCCGGGATGCCCTTCAGC |
| GCAGCGTTCAGCTGGCCATCGAAATTACCACCAACTCCCAGGAGGCAGCAGCCAAGCACGAGGCTC |
| AGAGACTGGAACAGGAAGCCCGTGGTCGGCTTGAGAGGCAGAAGATCTTGGACCAGTCAGAAGCTG |
| AAAAAGCCCGCAAGGAACTCTTGGAGCTTGAGGCTATGAGCATGGCTGTGGAGAGCACGGGTAATG |
| CCAAAGCAGAGGCTGAGTCCCGTGCAGAGGCAGCGAGGATCGAAGGAGAAGGCTCTGTGCTGCAGG |
| CCAAGCTCAAGGCACAGGCGCTAGCCATTGAGACGGAGGCTGAGTTGGAGCGAGTAAAGAAAGTAC |
| GAGAGATGGAACTGATCTATGCCCGGGCCCAGTTGGAGCTGGAGGTGAGCAAGGCGCAGCAGCTTG |
| CCAATGTGGAGGCAAAGAAGTTCAAGGAGATGACAGAGGCACTGGGCCCCGGCACCATCAGGGACC |
| TGGCTGTGGCCGGGCCAGAGATGCAGGTGAAACTTCTCCAGTCCCTGGGCCTGAAATCCACTCTCA |
| TCACCGATGGCTCGTCTCCCATCAACCTCTTCAGCACAGCCTTCGGGTTGCTGGGGCTGGGGTCTG |
| ATGGTCAGCCGCCAGCACAGAAG |
| pVI(aa 34-53)-MVP amino acid sequence |
| SEQ ID NO: 9 |
| M**AFSWGSLWSGIKNFGSTVKN**GLVPRGSAMATEEAIIRIPPYHYIHVLDQNSNVSRVEVGPKTYIR |
| QDNERVLFAPVRMVTVPPRHYCIVANPVSRDTQSSVLFDITGQVRLRHADQEIRLAQDPFPLYPGE |
| VLEKDITPLQVVLPNTALHLKALLDFEDKNGDKVMAGDEWLFEGPGTYIPQKEVEVVEIIQATVIK |
| QNQALRLRARKECFDREGKGRVTGEEWLVRSVGAYLPAVFEEVLDLVDAVILTEKTALHLRALQNF |
| RDLRGVLHRTGEEWLVTVQDTEAHVPDVYEEVLGVVPITTLGPRHYCVILDPMGPDGKNQLGQKRV |

TABLE 1-continued

| Sequences |
| --- |
| VKGEKSFFLQPGERLERGIQDVYVLSEQQGLLLKALQPLEEGESEEKVSHQAGDCWLIRGPLEYVP |
| SAKVEVVEERQAIPLDQNEGIYVQDVKTGKVRAVIGSTYMLTQDEVLWEKELPSGVEELLNLGHDP |
| LADRGQKGTAKPLQPSAPRNKTRVVSYRVPHNAAVQVYDYRAKRARVVFGPELVTLDPEEQFTVLS |
| LSAGRPKRPHARRALCLLLGPDFFTDVITIETADHARLQLQLAYNWHFELKNRNDPAEAAKLFSVP |
| DFVGDACKAIASRVRGAVASVTFDDFHKNSARIIRMAVFGFEMSEDTGPDGTLLPKARDQAVFPQN |
| GLVVSSVDVQSVEPVDQRTRDALQRSVQLAIEITTNSQEAAAKHEAQRLEQEARGRLERQKILDQS |
| EAEKARKELLELEAMSMAVESTGNAKAEAESRAEAARIEGEGSVLQAKLKAQALAIETEAELERVK |
| KVREMELIYARAQLELEVSKAQQLANVEAKKFKEMTEALGPGTIRDLAVAGPEMQVKLLQSLGLKS |
| TLITDGSSPINLFSTAFGLLGLGSDGQPPAQK |
| pVI(aa 34-53)-MVP-Z nucleotide sequence (pVI domain in bold, Z domain underlined) |
| SEQ ID NO: 10 |
| AANNNGNATTTTACTGTTTTCGTACAGTTTTGTAATAAAAAAACCTATAAATATTCCGGATTATTC |
| ATACCGTCCCACCATCGGGCGCGGATCCCGGTCCGAAGCGCGCGGAATTCGCGGCCGCGTCGACTG |
| TGGCTTGCAGCTGCCAGCTACCCTGCTAAATGTTTGGTGGGAAAAGCTTGGGATTCACCATG**GCCT** |
| **TCAGCTGGGGCTCGCTGTGGAGCGGCATTAAAAATTTCGGTTCCACCGTTAAGAAC**GGCCTGGTGC |
| CGCGCGGCAGCGCCATGGCAACTGAAGAGGCCATCATCCGCATCCCCCCATACCACTACATCCATG |
| TGCTGGACCAGAACAGTAATGTGTCCCGTGTGGAGGTTGGACCAAAGACCTACATCCGGCAGGACA |
| ATGAGAGGGTACTGTTTGCCCCAGTTCGCATGGTGACCGTCCCCCCACGCCACTACTGCATAGTGG |
| CCAACCCTGTGTCCCGGGACACCCAGAGTTCTGTGTTATTTGACATCACAGGACAAGTCCGACTCC |
| GGCACGCTGACCAGGAGATCCGACTAGCCCAGGACCCCTTCCCCCTGTATCCAGGGGAGGTGCTGG |
| AAAAGGACATCACCCCACTGCAGGTGGTTCTGCCCAACACAGCACTGCATCTTAAGGCGTTGCTGG |
| ACTTTGAGGATAAGAATGGAGACAAGGTCATGGCAGGAGACGAGTGGCTATTTGAGGGACCTGGCA |
| CCTACATCCCACAGAAGGAAGTGGAAGTCGTGGAGATCATTCAGGCCACAGTCATCAAACAGAACC |
| AAGCACTGCGGCTAAGGGCCCGAAAGGAGTGCTTTGACCGGGAGGGCAAGGGGCGCGTGACAGGTG |
| AGGAGTGGCTGGTCCGATCCGTGGGGGCTTACCTCCCAGCTGTCTTTGAAGAGGTGCTGGATCTGG |
| TGGATGCTGTGATCCTTACAGAAAAGACTGCCCTGCACCTCCGGGCTCTGCAGAACTTCAGGGACC |
| TTCGGGGAGTGCTCCACCGCACCGGGGAGGAATGGTTAGTGACAGTGCAGGACACAGAAGCCCATG |
| TTCCAGATGTCTATGAGGAGGTGCTTGGGGTAGTACCCATCACCACCCTGGGACCTCGACACTACT |
| GTGTCATTCTTGACCCAATGGGACCAGACGGCAAGAACCAGCTGGGACAAAAGCGTGTTGTCAAGG |
| GAGAGAAGTCCTTTTTCCTCCAGCCAGGAGAGAGGCTGGAGCGAGGCATCCAGGATGTGTATGTGC |
| TGTCAGAGCAGCAGGGGCTGCTACTGAAGGCACTGCAGCCCCTGGAGGAGGGAGAGAGCGAGGAGA |
| AGGTCTCCCATCAGGCCGGAGACTGCTGGCTCATCCGTGGGCCCCTGGAGTATGTGCCATCTGCAA |
| AAGTGGAGGTGGTGGAGGAGCGTCAGGCTATCCCTCTGGACCAAAATGAGGGCATCTATGTGCAGG |
| ATGTCAAGACGGGGAAGGTGCGGGCTGTGATTGGAAGCACCTACATGCTGACTCAGGATGAAGTCC |
| TGTGGGAAAAGGAGCTGCCTTCTGGGGTGGAGGAGCTGCTGAACTTGGGGCATGACCCTCTGGCAG |
| ACAGGGGTCAGAAGGGCACAGCCAAGCCCCTTCAGCCCTCAGCTCCAAGGAACAAGACCCGAGTGG |
| TCAGCTACCGTGTCCCGCACAATGCAGCGGTGCAGGTCTATGACTACAGAGCCAAGAGAGCCCGTG |
| TGGTCTTTGGGCCCGAGCTAGTGACACTGGATCCTGAGGAGCAGTTCACAGTATTGTCCCTTTCTG |
| CCGGGCGACCCAAGCGTCCTCATGCCCGCCGTGCACTCTGCCTACTGCTGGGACCTGATTTCTTTA |

TABLE 1-continued

| Sequences |
|---|
| CTGATGTCATCACCATCGAAACTGCAGATCATGCCAGGTTGCAGCTGCAGCTTGCCTACAACTGGC |
| ACTTTGAACTGAAGAACCGGAATGACCCTGCAGAGGCAGCCAAGCTTTTCTCCGTGCCTGACTTCG |
| TGGGTGACGCCTGCAAGGCCATTGCATCCCGAGTCCGGGGGGCTGTAGCCTCTGTCACCTTTGATG |
| ACTTCCATAAAAACTCAGCCCGGATCATTCGAATGGCTGTTTTTGGCTTTGAGATGTCTGAAGACA |
| CAGGTCCTGATGGCACACTCCTGCCCAAGGCTCGAGACCAGGCAGTCTTTCCCCAAAACGGGCTGG |
| TAGTCAGCAGTGTGGATGTGCAGTCAGTGGAGCCCGTGGACCAGAGGACCCGGGATGCCCTTCAGC |
| GCAGCGTTCAGCTGGCCATCGAAATTACCACCAACTCCCAGGAGGCAGCAGCCAAGCACGAGGCTC |
| AGAGACTGGAACAGGAAGCCCGTGGTCGGCTTGAGAGGCAGAAGATCTTGGACCAGTCAGAAGCTG |
| AAAAAGCCCGCAAGGAACTCTTGGAGCTTGAGGCTATGAGCATGGCTGTGGAGAGCACGGGTAATG |
| CCAAAGCAGAGGCTGAGTCCCGTGCAGAGGCAGCGAGGATCGAAGGAGAAGGCTCTGTGCTGCAGG |
| CCAAGCTCAAGGCACAGGCGCTAGCCATTGAGACGGAGGCTGAGTTGGAGCGAGTAAAGAAAGTAC |
| GAGAGATGGAACTGATCTATGCCCGGGCCCAGTTGGAGCTGGAGGTGAGCAAGGCGCAGCAGCTTG |
| CCAATGTGGAGGCAAAGAAGTTCAAGGAGATGACAGAGGCACTGGGCCCCGGCACCATCAGGGACC |
| TGGCTGTGGCCGGGCCAGAGATGCAGGTGAAACTTCTCCAGTCCCTGGGCCTGAAATCCACTCTCA |
| TCACCGATGGCTCGTCTCCCATCAACCTCTTCAGCACAGCCTTCGGGTTGCTGGGGCTGGGGTCTG |
| ATGGTCAGCCGCCAGCACAGAAG*TTT*AACATGCAGCAGCAGCGCCGCTTTTACGAGGCCCTGCACG |
| ACCCCAACCTGAACGAGGAGCAGCGCAACGCCAAGATTAAGAGCATTCGCGACGACTAG*GGTACC*T |
| CAG |
| pVI-MVP-Z amino acid sequence (pVI domain in bold, Z domain underlined) |

SEQ ID NO: 11

MAFSWGSLWSGIKNFGSTVKNGLVPRGSAMATEEAIIRIPPYHYIHVLDQNSNVSRVEVGPKTYIR
QDNERVLFAPVRMVTVPPRHYCIVANPVSRDTQSSVLFDITGQVRLRHADQEIRLAQDPFPLYPGE
VLEKDITPLQVVLPNTALHLKALLDFEDKNGDKVMAGDEWLFEGPGTYIPQKEVEVVEIIQATVIK
QNQALRLRARKECFDREGKGRVTGEEWLVRSVGAYLPAVFEEVLDLVDAVILTEKTALHLRALQNF
RDLRGVLHRTGEEWLVTVQDTEAHVPDVYEEVLGVVPITTLGPRHYCVILDPMGPDGKNQLGQKRV
VKGEKSFFLQPGERLERGIQDVYVLSEQQGLLLKALQPLEEGESEEKVSHQAGDCWLIRGPLEYVP
SAKVEVVEERQAIPLDQNEGIYVQDVKTGKVRAVIGSTYMLTQDEVLWEKELPSGVEELLNLGHDP
LADRGQKGTAKPLQPSAPRNKTRVVSYRVPHNAAVQVYDYRAKRARVVFGPELVTLDPEEQFTVLS
LSAGRPKRPHARRALCLLLGPDFFTDVITIETADHARLQLQLAYNWHFELKNRNDPAEAAKLFSVP
DFVGDACKAIASRVRGAVASVTFDDFHKNSARIIRMAVFGFEMSEDTGPDGTLLPKARDQAVFPQN
GLVVSSVDVQSVEPVDQRTRDALQRSVQLAIEITTNSQEAAAKHEAQRLEQEARGRLERQKILDQS
EAEKARKELLELEAMSMAVESTGNAKAEAESRAEAARIEGEGSVLQAKLKAQALAIETEAELERVK
KVREMELIYARAQLELEVSKAQQLANVEAKKFKEMTEALGPGTIRDLAVAGPEMQVKLLQSLGLKS
TLITDGSSPINLFSTAFGLLGLGSDGQPPAQKFNMQQQRRFYEALHDPNLNEEQRNAKIKSIRDD pVI-mINT fusion DNA sequence (pVI domain in bold, mINT domain underlined)

SEQ ID NO: 12 atg gcc ttc agc tgg ggc tcg ctg tgg agc ggc att aaa aat ttc ggt tcc acc gtt aag aac tat ggc agc aag gcc tgg aac agc agc aca ggc cag atg ctg agg gat aag ttg aaa gag caa aat ttc caa caa aag gtg gta gat ggc ctg gcc tct

TABLE 1-continued

| Sequences |
|---|
| **ggc att agc ggg gtg gtg gac ctg gcc aac cag gca gtg caa aat aag att aac** |
| **agt aag ctt gat ccc cgc cct ccc gta gag** gga tcc gaa ttc ggc acg agg cgg |
| tgc aca caa cac tgg cag gat gct gtg cct tgg aca gaa ctc ctc agt cta cag |
| aca gag gat ggc ttc tgg aaa ctt aca cca gaa ctg gga ctt ata tta aat ctt |
| aat aca aat ggt ttg cac agc ttt ctt aaa caa aaa ggc att caa tct cta ggt |
| gta aaa gga aga gaa tgt ctc ctg gac cta att gcc aca atg ctg gta cta cag |
| ttt att cgc acc agg ttg gaa aaa gag gga ata gtg ttc aaa tca ctg atg aaa |
| atg gat gac cct tct att tcc agg aat att ccc tgg gct ttt gag gca ata aag |
| caa gca agt gaa tgg gta aga aga act gaa gga cag tac cca tct atc tgc cca |
| cgg ctt gaa ctg ggg aac gac tgg gac tct gcc acc aag cag ttg ctg gga ctc |
| cag ccc ata agc act gtg tcc cct ctt cat aga gtc ctc cat tac agt caa ggc |
| taa |
| pVI-mINT fusion Protein sequence (pVI domain in bold, mINT domain underlined) |
| SEQ ID NO: 13 |
| **MAFSWGSLWS GIKNFGSTVK NYGSKAWNSS TGQMLRDKLK EQNFQQKVVD GLASGISGVV** |
| **DLANQAVQNK INSKLDPRPP VE**GSEFGTRR CTQHWQDAVP WTELLSLQTE DGFWKLTPEL |
| GLILNLNTNG LHSFLKQKGI QSLGVKGREC LLDLIATMLV LQFIRTRLEK EGIVFKSLMK |
| MDDPSISRNI PWAFEAIKQA SEWVRRTEGQ YPSICPRLEL GNDWDSATKQ LLGLQPISTV |
| SPLHRVLHYS QG |
| VPARP protein sequence (Genbank #AAD47250) |
| SEQ ID NO: 14 |
| Met Val Met Gly Ile Phe Ala Asn Cys Ile Phe Cys Leu Lys Val Lys Tyr Leu |
| Pro Gln Gln Gln Lys Lys Lys Leu Gln Thr Asp Ile Lys Glu Asn Gly Gly Lys |
| Phe Ser Phe Ser Leu Asn Pro Gln Cys Thr His Ile Ile Leu Asp Asn Ala Asp |
| Val Leu Ser Gln Tyr Gln Leu Asn Ser Ile Gln Lys Asn His Val His Ile Ala |
| Asn Pro Asp Phe Ile Trp Lys Ser Ile Arg Glu Lys Arg Leu Leu Asp Val Lys |
| Asn Tyr Asp Pro Tyr Lys Pro Leu Asp Ile Thr Pro Pro Pro Asp Gln Lys Ala |
| Ser Ser Ser Glu Val Lys Thr Glu Gly Leu Cys Pro Asp Ser Ala Thr Glu Glu |
| Glu Asp Thr Val Glu Leu Thr Glu Phe Gly Met Gln Asn Val Glu Ile Pro His |
| Leu Pro Gln Asp Phe Glu Val Ala Lys Tyr Asn Thr Leu Glu Lys Val Gly Met |
| Glu Gly Gly Gln Glu Ala Val Val Val Glu Leu Gln Cys Ser Arg Asp Ser Arg |
| Asp Cys Pro Phe Leu Ile Ser Ser His Phe Leu Leu Asp Asp Gly Met Glu Thr |
| Arg Arg Gln Phe Ala Ile Lys Lys Thr Ser Glu Asp Ala Ser Glu Tyr Phe Glu |
| Asn Tyr Ile Glu Glu Leu Lys Lys Gln Gly Phe Leu Leu Arg Glu His Phe Thr |
| Pro Glu Ala Thr Gln Leu Ala Ser Glu Gln Leu Gln Ala Leu Leu Leu Glu Glu |
| Val Met Asn Ser Ser Thr Leu Ser Gln Glu Val Ser Asp Leu Val Glu Met Ile |
| Trp Ala Glu Ala Leu Gly His Leu Glu His Met Leu Leu Lys Pro Val Asn Arg |
| Ile Ser Leu Asn Asp Val Ser Lys Ala Glu Gly Ile Leu Leu Leu Val Lys Ala |
| Ala Leu Lys Asn Gly Glu Thr Ala Glu Gln Leu Gln Lys Met Met Thr Glu Phe |
| Tyr Arg Leu Ile Pro His Lys Gly Thr Met Pro Lys Glu Val Asn Leu Gly Leu |

TABLE 1-continued

| Sequences |
|---|
| Leu Ala Lys Lys Ala Asp Leu Cys Gln Leu Ile Arg Asp Met Val Asn Val Cys |
| Glu Thr Asn Leu Ser Lys Pro Asn Pro Pro Ser Leu Ala Lys Tyr Arg Ala Leu |
| Arg Cys Lys Ile Glu His Val Glu Gln Asn Thr Glu Glu Phe Leu Arg Val Arg |
| Lys Glu Val Leu Gln Asn His His Ser Lys Ser Pro Val Asp Val Leu Gln Ile |
| Phe Arg Val Gly Arg Val Asn Glu Thr Thr Glu Phe Leu Ser Lys Leu Gly Asn |
| Val Arg Pro Leu Leu His Gly Ser Pro Val Gln Asn Ile Val Gly Ile Leu Cys |
| Arg Gly Leu Leu Leu Pro Lys Val Val Glu Asp Arg Gly Val Gln Arg Thr Asp |
| Val Gly Asn Leu Gly Ser Gly Ile Tyr Phe Ser Asp Ser Leu Ser Thr Ser Ile |
| Lys Tyr Ser His Pro Gly Glu Thr Asp Gly Thr Arg Leu Leu Leu Ile Cys Asp |
| Val Ala Leu Gly Lys Cys Met Asp Leu His Glu Lys Asp Phe Pro Leu Thr Glu |
| Ala Pro Pro Gly Tyr Asp Ser Val His Gly Val Ser Gln Thr Ala Ser Val Thr |
| Thr Asp Phe Glu Asp Asp Glu Phe Val Val Tyr Lys Thr Asn Gln Val Lys Met |
| Lys Tyr Ile Ile Lys Phe Ser Met Pro Gly Asp Gln Ile Lys Asp Phe His Pro |
| Ser Asp His Thr Glu Leu Glu Glu Tyr Arg Pro Glu Phe Ser Asn Phe Ser Lys |
| Val Glu Asp Tyr Gln Leu Pro Asp Ala Lys Thr Ser Ser Ser Thr Lys Ala Gly |
| Leu Gln Asp Ala Ser Gly Asn Leu Val Pro Leu Glu Asp Val His Ile Lys Gly |
| Arg Ile Ile Asp Thr Val Ala Gln Val Ile Val Phe Gln Thr Tyr Thr Asn Lys |
| Ser His Val Pro Ile Glu Ala Lys Tyr Ile Phe Pro Leu Asp Asp Lys Ala Ala |
| Val Cys Gly Phe Glu Ala Phe Ile Asn Gly Lys His Ile Val Gly Glu Ile Lys |
| Glu Lys Glu Glu Ala Gln Gln Glu Tyr Leu Glu Ala Val Thr Gln Gly His Gly |
| Ala Tyr Leu Met Ser Gln Asp Ala Pro Asp Val Phe Thr Val Ser Val Gly Asn |
| Leu Pro Pro Lys Ala Lys Val Leu Ile Lys Ile Thr Tyr Ile Thr Glu Leu Ser |
| Ile Leu Gly Thr Val Gly Val Phe Phe Met Pro Ala Thr Val Ala Pro Trp Gln |
| Gln Asp Lys Ala Leu Asn Glu Asn Leu Gln Asp Thr Val Glu Lys Ile Cys Ile |
| Lys Glu Ile Gly Thr Lys Gln Ser Phe Ser Leu Thr Met Ser Ile Glu Met Pro |
| Tyr Val Ile Glu Phe Ile Phe Ser Asp Thr His Glu Leu Lys Gln Lys Arg Thr |
| Asp Cys Lys Ala Val Ile Ser Thr Met Glu Gly Ser Ser Leu Asp Ser Ser Gly |
| Phe Ser Leu His Ile Gly Leu Ser Ala Ala Tyr Leu Pro Arg Met Trp Val Glu |
| Lys His Pro Glu Lys Glu Ser Glu Ala Cys Met Leu Val Phe Gln Pro Asp Leu |
| Asp Val Asp Leu Pro Asp Leu Ala Ser Glu Ser Glu Val Ile Ile Cys Leu Asp |
| Cys Ser Ser Ser Met Glu Gly Val Thr Phe Leu Gln Ala Lys Gln Ile Thr Leu |
| His Ala Leu Ser Leu Val Gly Glu Lys Gln Lys Val Asn Ile Ile Gln Phe Gly |
| Thr Gly Tyr Lys Glu Leu Phe Ser Tyr Pro Lys His Ile Thr Ser Asn Thr Thr |
| Ala Ala Glu Phe Ile Met Ser Ala Thr Pro Thr Met Gly Asn Thr Asp Phe Trp |
| Lys Thr Leu Arg Tyr Leu Ser Leu Leu Tyr Pro Ala Arg Gly Ser Arg Asn Ile |
| Leu Leu Val Ser Asp Gly His Leu Gln Asp Glu Ser Leu Thr Leu Gln Leu Val |
| Lys Arg Ser Arg Pro His Thr Arg Leu Phe Ala Cys Gly Ile Gly Ser Thr Ala |
| Asn Arg His Val Leu Arg Ile Leu Ser Gln Cys Gly Ala Gly Val Phe Glu Tyr |
| Phe Asn Ala Lys Ser Lys His Ser Trp Arg Lys Gln Ile Glu Asp Gln Met Thr |

TABLE 1-continued

| Sequences |
|---|
| Arg Leu Cys Ser Pro Ser Cys His Ser Val Ser Val Lys Trp Gln Gln Leu Asn |
| Pro Asp Ala Pro Glu Ala Leu Gln Ala Pro Ala Gln Val Pro Ser Leu Phe Arg |
| Asn Asp Arg Leu Leu Val Tyr Gly Phe Ile Pro His Cys Thr Gln Ala Thr Leu |
| Cys Ala Leu Ile Gln Glu Lys Glu Phe Cys Thr Met Val Ser Thr Thr Glu Leu |
| Gln Lys Thr Thr Gly Thr Met Ile His Lys Leu Ala Ala Arg Ala Leu Ile Arg |
| Asp Tyr Glu Asp Gly Ile Leu His Glu Asn Glu Thr Ser His Glu Met Lys Lys |
| Gln Thr Leu Lys Ser Leu Ile Ile Lys Leu Ser Lys Glu Asn Ser Leu Ile Thr |
| Gln Phe Thr Ser Phe Val Ala Val Glu Lys Arg Asp Glu Asn Glu Ser Pro Phe |
| Pro Asp Ile Pro Lys Val Ser Glu Leu Ile Ala Lys Glu Asp Val Asp Phe Leu |
| Pro Tyr Met Ser Trp Gln Gly Glu Pro Gln Glu Ala Val Arg Asn Gln Ser Leu |
| Leu Ala Ser Ser Glu Trp Pro Glu Leu Arg Leu Ser Lys Arg Lys His Arg Lys |
| Ile Pro Phe Ser Lys Arg Lys Met Glu Leu Ser Gln Pro Glu Val Ser Glu Asp |
| Phe Glu Glu Asp Gly Leu Gly Val Leu Pro Ala Phe Thr Ser Asn Leu Glu Arg |
| Gly Gly Val Glu Lys Leu Leu Asp Leu Ser Trp Thr Glu Ser Cys Lys Pro Thr |
| Ala Thr Glu Pro Leu Phe Lys Lys Val Ser Pro Trp Glu Thr Ser Thr Ser Ser |
| Phe Phe Pro Ile Leu Ala Pro Ala Val Gly Ser Tyr Leu Thr Pro Thr Thr Arg |
| Ala His Ser Pro Ala Ser Leu Ser Phe Ala Ser Tyr Arg Gln Val Ala Ser Phe |
| Gly Ser Ala Ala Pro Pro Arg Gln Phe Asp Ala Ser Gln Phe Ser Gln Gly Pro |
| Val Pro Gly Thr Cys Ala Asp Trp Ile Pro Gln Ser Ala Ser Cys Pro Thr Gly |
| Pro Pro Gln Asn Pro Pro Ser Ala Pro Tyr Cys Gly Ile Val Phe Ser Gly Ser |
| Ser Leu Ser Ser Ala Gln Ser Ala Pro Leu Gln His Pro Gly Gly Phe Thr Thr |
| Arg Pro Ser Ala Gly Thr Phe Pro Glu Leu Asp Ser Pro Gln Leu His Phe Ser |
| Leu Pro Thr Asp Pro Asp Pro Ile Arg Gly Phe Gly Ser Tyr His Pro Ser Ala |
| Tyr Ser Pro Phe His Phe Gln Pro Ser Ala Ala Ser Leu Thr Ala Asn Leu Arg |
| Leu Pro Met Ala Ser Ala Leu Pro Glu Ala Leu Cys Ser Gln Ser Arg Thr Thr |
| Pro Val Asp Leu Cys Leu Leu Glu Glu Ser Val Gly Ser Leu Glu Gly Ser Arg |
| Cys Pro Val Phe Ala Phe Gln Ser Ser Asp Thr Glu Ser Asp Glu Leu Ser Glu |
| Val Leu Gln Asp Ser Cys Phe Leu Gln Ile Lys Cys Asp Thr Lys Asp Asp Ser |
| Ile Pro Cys Phe Leu Glu Leu Lys Glu Glu Asp Glu Ile Val Cys Thr Gln His |
| Trp Gln Asp Ala Val Pro Trp Thr Glu Leu Leu Ser Leu Gln Thr Glu Asp Gly |
| Phe Trp Lys Leu Thr Pro Glu Leu Gly Leu Ile Leu Asn Leu Asn Thr Asn Gly |
| Leu His Ser Phe Leu Lys Gln Lys Gly Ile Gln Ser Leu Gly Val Lys Gly Arg |
| Glu Cys Leu Leu Asp Leu Ile Ala Thr Met Leu Val Leu Gln Phe Ile Arg Thr |
| Arg Leu Glu Lys Glu Gly Ile Val Phe Lys Ser Leu Met Lys Met Asp Asp Pro |
| Ser Ile Ser Arg Asn Ile Pro Trp Ala Phe Glu Ala Ile Lys Gln Ala Ser Glu |
| Trp Val Arg Arg Thr Glu Gly Gln Tyr Pro Ser Ile Cys Pro Arg Leu Glu Leu |
| Gly Asn Asp Trp Asp Ser Ala Thr Lys Gln Leu Leu Gly Leu Gln Pro Ile Ser |
| Thr Val Ser Pro Leu His Arg Val Leu His Tyr Ser Gln Gly |
| VPARP cDNA, Genbank #AF158255 |

TABLE 1-continued

| Sequences |
|---|
| SEQ ID NO: 15 |
| atggtgatgg gaatctttgc aaattgtatc ttctgtttga aagtgaagta cttacctcag |
| cagcagaaga aaaagctaca aactgacatt aaggaaaatg gcggaaagtt ttcctttttcg |
| ttaaatcctc agtgcacaca tataatctta gataatgctg atgttctgag tcagtaccaa |
| ctgaattcta tccaaaagaa ccacgttcat attgcaaacc cagattttat atggaaatct |
| atcagagaaa agagactctt ggatgtaaag aattatgatc cttataagcc cctggacatc |
| acaccacctc ctgatcagaa ggcgagcagt tctgaagtga aaacagaagg tctatgcccg |
| gacagtgcca cagaggagga agacactgtg gaactcactg agtttggtat gcagaatgtt |
| gaaattcctc atcttcctca agattttgaa gttgcaaaat ataacacctt ggagaaagtg |
| ggaatggagg gaggccagga agctgtggtg gtggagcttc agtgttcgcg ggactccagg |
| gactgtcctt tcctgatatc ctcacacttc ctcctggatg atggcatgga gactagaaga |
| cagtttgcta taaagaaaac ctctgaagat gcaagtgaat actttgaaaa ttacattgaa |
| gaactgaaga aacaaggatt tctactaaga gaacatttca cacctgaagc aacccaatta |
| gcatctgaac aattgcaagc attgcttttg gaggaagtca tgaattcaag cactctgagc |
| caagaggtga gcgatttagt agagatgatt tgggcagagg ccctgggcca cctggaacac |
| atgcttctca agccagtgaa caggattagc ctcaacgatg tgagcaaggc agaggggatt |
| ctccttctag taaaggcagc actgaaaaat ggagaaacag cagagcaatt gcaaaagatg |
| atgacagagt tttacagact gatacctcac aaaggcacaa tgcccaaaga agtgaacctg |
| ggactattgg ctaagaaagc agacctctgc cagctaataa gagacatggt taatgtctgt |
| gaaactaatt tgtccaaacc caacccacca tccctggcca aataccgagc tttgaggtgc |
| aaaattgagc atgttgaaca gaatactgaa gaatttctca gggttagaaa agaggttttg |
| cagaatcatc acagtaagag cccagtggat gtcttgcaga tatttagagt tggcagagtg |
| aatgaaacca cagagttttt gagcaaactt ggtaatgtga ggcccttgtt gcatggttct |
| cctgtacaaa acatcgtggg aatcttgtgt cgagggttgc ttttacccaa agtagtggaa |
| gatcgtggtg tgcaaagaac agacgtcgga aaccttggaa gtgggattta tttcagtgat |
| tcgctcagta caagtatcaa gtactcacac ccgggagaga cagatggcac cagactcctg |
| ctcatttgtg acgtagccct cggaaagtgt atggacttac atgagaagga ctttccctta |
| actgaagcac caccaggcta cgacagtgtg catggagttt cacaaacagc ctctgtcacc |
| acagactttg aggatgatga atttgttgtc tataaaacca atcaggttaa aatgaaatat |
| attattaaat tttccatgcc tggagatcag ataaaggact ttcatcctag tgatcatact |
| gaattagagg aatacagacc tgagttttca aatttttcaa aggttgaaga ttaccagtta |
| ccagatgcca aaacttccag cagcaccaag gccggcctcc aggatgcctc tgggaacttg |
| gttcctctgg aggatgtcca catcaaaggg agaatcatag acactgtagc ccaggtcatt |
| gtttttcaga catacacaaa taaaagtcac gtgcccattg aggcaaaata tatctttcct |
| ttggatgaca aggccgctgt gtgtggcttc gaagccttca tcaatgggaa gcacatagtt |
| ggagagatta aagagaagga agaagcccag caagagtacc tagaagccgt gacccagggc |
| catggcgctt acctgatgag tcaggatgct ccggacgttt ttactgtaag tgttggaaac |
| ttacccccta aggctaaggt tcttataaaa attacctaca tcacagaact cagcatcctg |
| ggcactgttg gtgtcttttt catgcccgcc accgtagcac cctggcaaca ggacaaggct |
| ttgaatgaaa accttcagga tacagtagag aagatttgta taaaagaaat aggaacaaag |

TABLE 1-continued

| Sequences |
|---|
| caaagcttct ctttgactat gtctattgag atgccgtatg tgattgaatt cattttcagt |
| gatacacatg aactgaaaca aaagcgcaca gactgcaaag ctgtcattag caccatggaa |
| ggcagctcct tagacagcag tggattttct ctccacatcg gtttgtctgc tgcctatctc |
| ccaagaatgt gggttgaaaa acatccagaa aaagaaagcg aggcttgcat gcttgtcttt |
| caacccgatc tcgatgtcga cctccctgac ctagccagtg agagcgaagt gattatttgt |
| cttgactgct ccagttccat ggagggtgtg acattcttgc aagccaagca aatcaccttg |
| catgcgctgt ccttggtggg tgagaagcag aaagtaaata ttatccagtt cggcacaggt |
| tacaaggagc tattttcgta tcctaagcat atcacaagca ataccacggc agcagagttc |
| atcatgtctg ccacacctac catggggaac acagacttct ggaaaacact ccgatatctt |
| agcttattgt accctgctcg agggtcacgg aacatcctcc tggtgtctga tgggcacctc |
| caggatgaga gcctgacatt acagctcgtg aagaggagcc gcccgcacac caggttattc |
| gcctgcggta tcggttctac agcaaatcgt cacgtcttaa ggattttgtc ccagtgtggt |
| gccggagtat ttgaatattt taatgcaaaa tccaagcata gttggagaaa acagatagaa |
| gaccaaatga ccaggctatg ttctccgagt tgccactctg tctccgtcaa atggcagcaa |
| ctcaatccag atgcgcccga ggccctgcag gccccagccc aggtgccatc cttgtttcgc |
| aatgatcgac tccttgtcta tggattcatt cctcactgca cacaagcaac tctgtgtgca |
| ctaattcaag agaaagaatt ttgtacaatg gtgtcgacta ctgagcttca gaagacaact |
| ggaactatga tccacaagct ggcagcccga gctctaatca gagattatga agatggcatt |
| cttcacgaaa atgaaaccag tcatgagatg aaaaaacaaa ccttgaaatc tctgattatt |
| aaactcagta aagaaaactc tctcataaca caatttacaa gctttgtggc agttgagaaa |
| agggatgaga atgagtcgcc ttttcctgat attccaaaag tttctgaact tattgccaaa |
| gaagatgtag acttcctgcc ctacatgagc tggcaggggg agccccaaga agccgtcagg |
| aaccagtctc ttttagcatc ctctgagtgg ccagaattac gtttatccaa acgaaaacat |
| aggaaaattc cattttccaa aagaaaaatg gaattatctc agccagaagt ttctgaagat |
| tttgaagagg atggcttagg tgtactacca gctttcacat caaatttgga acgtggaggt |
| gtggaaaagc tattggattt aagttggaca gagtcatgta aaccaacagc aactgaacca |
| ctatttaaga aagtcagtcc atgggaaaca tctacttcta gctttttttcc tattttggct |
| ccggccgttg gttcctatct taccccgact acccgcgctc acagtcctgc ttccttgtct |
| tttgcctcat atcgtcaggt agctagtttc ggttcagctg ctcctcccag acagtttgat |
| gcatctcaat tcagccaagg ccctgtgcct ggcacttgtg ctgactggat cccacagtcg |
| gcgtcttgtc ccacaggacc tccccagaac ccaccttctg caccctattg tggcattgtt |
| ttttcaggga gctcattaag ctctgcacag tctgctccac tgcaacatcc tggaggcttt |
| actaccaggc cttctgctgg caccttccct gagctggatt ctccccagct tcatttctct |
| cttcctacag accctgatcc catcagaggt tttgggtctt atcatccctc tgcttactct |
| ccttttcatt ttcaaccttc cgcagcctct ttgactgcca accttaggct gccaatggcc |
| tctgctttac ctgaggctct ttgcagtcag tcccggacta ccccagtaga tctctgtctt |
| ctagaagaat cagtaggcag tctcgaagga agtcgatgtc ctgtctttgc ttttcaaagt |
| tctgacacag aaagtgatga gctatcagaa gtacttcaag acagctgctt tttacaaata |
| aagtgtgata caaaagatga cagtatcccg tgctttctgg aattaaaaga agaggatgaa |

TABLE 1-continued

| Sequences |
|---|
| atagtgtgca cacaacactg gcaggatgct gtgccttgga cagaactcct cagtctacag<br>acagaggatg gcttctggaa acttacacca gaactgggac ttatattaaa tcttaataca<br>aatggtttgc acagctttct taaacaaaaa ggcattcaat ctctaggtgt aaaaggaaga<br>gaatgtctcc tggacctaat tgccacaatg ctggtactac agtttattcg caccaggttg<br>gaaaaagagg gaatagtgtt caaatcactg atgaaaatgg atgacccttc tatttccagg<br>aatattccct gggcttttga ggcaataaag caagcaagtg aatgggtaag aagaactgaa<br>ggacagtacc catctatctg cccacggctt gaactgggga acgactggga ctctgccacc<br>aagcagttgc tgggactcca gcccataagc actgtgtccc ctcttcatag agtcctccat<br>tacagtcaag gctaa |
| MVP (Genbank #CAA56256) |
| SEQ ID NO: 16<br>Met Ala Thr Glu Glu Phe Ile Ile Arg Ile Pro Pro Tyr His Tyr Ile His Val<br>Leu Asp Gln Asn Ser Asn Val Ser Arg Val Glu Val Gly Pro Lys Thr Tyr Ile<br>Arg Gln Asp Asn Glu Arg Val Leu Phe Ala Pro Met Arg Met Val Thr Val Pro<br>Pro Arg His Tyr Cys Thr Val Ala Asn Pro Val Ser Arg Asp Ala Gln Gly Leu<br>Val Leu Phe Asp Val Thr Gly Gln Val Arg Leu Arg His Ala Asp Leu Glu Ile<br>Arg Leu Ala Gln Asp Pro Phe Pro Leu Tyr Pro Gly Glu Val Leu Glu Lys Asp<br>Ile Thr Pro Leu Gln Val Val Leu Pro Asn Thr Ala Leu His Leu Lys Ala Leu<br>Leu Asp Phe Glu Asp Lys Asp Gly Asp Lys Val Val Ala Gly Asp Glu Trp Leu<br>Phe Glu Gly Pro Gly Thr Tyr Ile Pro Arg Lys Glu Val Glu Val Val Glu Ile<br>Ile Gln Ala Thr Ile Ile Arg Gln Asn Gln Ala Leu Arg Leu Arg Ala Arg Lys<br>Glu Cys Trp Asp Arg Asp Gly Lys Glu Arg Val Thr Gly Glu Glu Trp Leu Val<br>Thr Thr Val Gly Ala Tyr Leu Pro Ala Val Phe Glu Glu Val Leu Asp Leu Val<br>Asp Ala Val Ile Leu Thr Glu Lys Thr Ala Leu His Leu Arg Ala Arg Arg Asn<br>Phe Arg Asp Phe Arg Gly Val Ser Arg Arg Thr Gly Glu Glu Trp Leu Val Thr<br>Val Gln Asp Thr Glu Ala His Val Pro Asp Val His Glu Glu Val Leu Gly Val<br>Val Pro Ile Thr Thr Leu Gly Pro His Asn Tyr Cys Val Ile Leu Asp Pro Val<br>Gly Pro Asp Gly Lys Asn Gln Leu Gly Gln Lys Arg Val Val Lys Gly Glu Lys<br>Ser Phe Phe Leu Gln Pro Gly Glu Gln Leu Glu Gln Gly Ile Gln Asp Val Tyr<br>Val Leu Ser Glu Gln Gln Gly Leu Leu Leu Arg Ala Leu Gln Pro Leu Glu Glu<br>Gly Glu Asp Glu Glu Lys Val Ser His Gln Ala Gly Asp His Trp Leu Ile Arg<br>Gly Pro Leu Glu Tyr Val Pro Ser Ala Lys Val Glu Val Val Glu Glu Arg Gln<br>Ala Ile Pro Leu Asp Glu Asn Glu Gly Ile Tyr Val Gln Asp Val Lys Thr Gly<br>Lys Val Arg Ala Val Ile Gly Ser Thr Tyr Met Leu Thr Gln Asp Glu Val Leu<br>Trp Glu Lys Glu Leu Pro Pro Gly Val Glu Glu Leu Leu Asn Lys Gly Gln Asp<br>Pro Leu Ala Asp Arg Gly Glu Lys Asp Thr Ala Lys Ser Leu Gln Pro Leu Ala<br>Pro Arg Asn Lys Thr Arg Val Val Ser Tyr Arg Val Pro His Asn Ala Ala Val<br>Gln Val Tyr Asp Tyr Arg Glu Lys Arg Ala Arg Val Val Phe Gly Pro Glu Leu<br>Val Ser Leu Gly Pro Glu Glu Gln Phe Thr Val Leu Ser Leu Ser Ala Gly Arg |

TABLE 1-continued

| Sequences |
|---|
| Pro Lys Arg Pro His Ala Arg Arg Ala Leu Cys Leu Leu Leu Gly Pro Asp Phe |
| Phe Thr Asp Val Ile Thr Ile Glu Thr Ala Asp His Ala Arg Leu Gln Leu Gln |
| Leu Ala Tyr Asn Trp His Phe Glu Val Asn Asp Arg Lys Asp Pro Gln Glu Thr |
| Ala Lys Leu Phe Ser Val Pro Asp Phe Val Gly Asp Ala Cys Lys Ala Ile Ala |
| Ser Arg Val Arg Gly Ala Val Ala Ser Val Thr Phe Asp Asp Phe His Lys Asn |
| Ser Ala Arg Ile Ile Arg Thr Ala Val Phe Gly Phe Glu Thr Ser Glu Ala Lys |
| Gly Pro Asp Gly Met Ala Leu Pro Arg Pro Arg Asp Gln Ala Val Phe Pro Gln |
| Asn Gly Leu Val Val Ser Ser Val Asp Val Gln Ser Val Glu Pro Val Asp Gln |
| Arg Thr Arg Asp Ala Leu Gln Arg Ser Val Gln Leu Ala Ile Glu Ile Thr Thr |
| Asn Ser Gln Glu Ala Ala Ala Lys His Glu Ala Gln Arg Leu Glu Gln Glu Ala |
| Arg Gly Arg Leu Glu Arg Gln Lys Ile Leu Asp Gln Ser Glu Ala Glu Lys Ala |
| Arg Lys Glu Leu Leu Glu Leu Glu Ala Leu Ser Met Ala Val Glu Ser Thr Gly |
| Thr Ala Lys Ala Glu Ala Glu Ser Arg Ala Glu Ala Ala Arg Ile Glu Gly Glu |
| Gly Ser Val Leu Gln Ala Lys Leu Lys Ala Gln Ala Leu Ala Ile Glu Thr Glu |
| Ala Glu Leu Gln Arg Val Gln Lys Val Arg Glu Leu Glu Leu Val Tyr Ala Arg |
| Ala Gln Leu Glu Leu Glu Val Ser Lys Ala Gln Gln Leu Ala Glu Val Glu Val |
| Lys Lys Phe Lys Gln Met Thr Glu Ala Ile Gly Pro Ser Thr Ile Arg Asp Leu |
| Ala Val Ala Gly Pro Glu Met Gln Val Lys Leu Leu Gln Ser Leu Gly Leu Lys |
| Ser Thr Leu Ile Thr Asp Gly Ser Thr Pro Ile Asn Leu Phe Asn Thr Ala Phe |
| Gly Leu Leu Gly Met Gly Pro Glu Gly Gln Pro Leu Gly Arg Arg Val Ala Ser |
| Gly Pro Ser Pro Gly Glu Gly Ile Ser Pro Gln Ser Ala Gln Ala Pro Gln Ala |
| Pro Gly Asp Asn His Val Val Pro Val Leu Arg |
| MVP cDNA, Genbank #X79882 |
| SEQ ID NO: 17 |
| atggcaactg aagagttcat catccgcatc cccccatacc actatatcca tgtgctggac |
| cagaacagca acgtgtcccg tgtggaggtc gggccaaaga cctacatccg gcaggacaat |
| gagagggtac tgtttgcccc catgcgcatg gtgaccgtcc ccccacgtca ctactgcaca |
| gtggccaacc ctgtgtctcg ggatgcccag ggcttggtgc tgtttgatgt cacagggcaa |
| gttcggcttc gccacgctga cctcgagatc cggctggccc aggacccctt cccccctgtac |
| ccaggggagg tgctggaaaa ggacatcaca cccctgcagg tggttctgcc caacactgcc |
| ctccatctaa aggcgctgct tgattttgag gataaagatg gagacaaggt ggtggcagga |
| gatgagtggc ttttcgaggg acctggcacg tacatccccc ggaaggaagt ggaggtcgtg |
| gagatcattc aggccaccat catcaggcag aaccaggctc tgcggctcag ggcccgcaag |
| gagtgccggg accgggacgg caaggagagg gtgacagggg aagaatggct ggtcaccaca |
| gtaggggcgt acctcccagc ggtgtttgag gaggttctgg atttggtgga cgccgtcatc |
| cttacggaaa agacagccct gcacctccgg gctcggcgga acttccggga cttcagggga |
| gtgtcccgcc gcactgggga ggagtggctg gtaacagtgc aggacacaga ggcccacgtg |
| ccagatgtcc acgaggaggt gctgggggtt gtgcccatca ccaccctggg cccccacaac |
| tactgcgtga ttctcgaccc tgtcggaccg gatggcaaga atcagctggg gcagaagcgc |
| gtggtcaagg gagagaagtc ttttttcctc cagccaggag agcagctgga acaaggcatc |

TABLE 1-continued

| Sequences |
|---|
| caggatgtgt atgtgctgtc ggagcagcag gggctgctgc tgagggccct gcagcccctg |
| gaggaggggg aggatgagga gaaggtctca caccaggctg gggaccactg gctcatccgc |
| ggacccctgg agtatgtgcc atctgccaaa gtggaggtgg tggaggagcg ccaggccatc |
| cctctagacg agaacgaggg catctatgtg caggatgtca agaccggaaa ggtgcgcgct |
| gtgattggaa gcacctacat gctgacccag gacgaagtcc tgtgggagaa agagctgcct |
| cccggggtgg aggagctgct gaacaagggg caggaccctc tggcagacag gggtgagaag |
| gacacagcta agagcctcca gcccttggcg ccccggaaca agacccgtgt ggtcagctac |
| cgcgtgcccc acaacgctgc ggtgcaggtg tacgactacc gagagaagcg agcccgcgtg |
| gtcttcgggc ctgagctggt gtcgctgggt cctgaggagc agttcacagt gttgtccctc |
| tcagctgggc ggcccaagcg tccccatgcc cgccgtgcgc tctgcctgct gctggggcct |
| gacttcttca cagacgtcat caccatcgaa acggcggatc atgccaggct gcaactgcag |
| ctggcctaca actggcactt tgaggtgaat gaccggaagg acccccaaga gacggccaag |
| ctcttttcag tgccagactt tgtaggtgat gcctgcaaag ccatcgcatc ccgggtgcgg |
| ggggccgtgg cctctgtcac tttcgatgac ttccataaga actcagcccg catcattcgc |
| actgctgtct ttggctttga gacctcggaa gcgaagggcc ccgatggcat ggccctgccc |
| aggccccggg accaggctgt cttcccccaa aacgggctgg tggtcagcag tgtggacgtg |
| cagtcagtgg agcctgtgga tcagaggacc cgggacgccc tgcaacgcag cgtccagctg |
| gccatcgaga tcaccaccaa ctcccaggaa gcggcggcca agcatgaggc tcagagactg |
| gagcaggaag cccgcggccg gcttgagcgg cagaagatcc tggaccagtc agaagccgag |
| aaagctcgca aggaactttt ggagctggag gctctgagca tggccgtgga gagcaccggg |
| actgccaagg cggaggccga gtcccgtgcg gaggcagccc ggattgaggg agaagggtcc |
| gtgctgcagg ccaagctaaa agcacaggcc ttggccattg aaacggaggc tgagctccag |
| agggtccaga aggtccgaga gctggaactg gtctatgccc gggcccagct ggagctggag |
| gtgagcaagg ctcagcagct ggctgaggtg gaggtgaaga agttcaagca gatgacagag |
| gccataggcc ccagcaccat cagggacctt gctgtggctg ggcctgagat gcaggtaaaa |
| ctgctccagt ccctgggcct gaaatcaacc ctcatcaccg atggctccac tcccatcaac |
| ctcttcaaca cagcctttgg gctgctgggg atggggcccg agggtcagcc cctgggcaga |
| agggtggcca gtgggcccag ccctggggag gggatatccc cccagtctgc tcaggcccct |
| caagctcctg gagacaacca cgtggtgcct gtactgcgct aa |
| CP Peptide |
| SEQ ID NO: 18<br>Met Ala Gly Cys Gly Cys Pro Cys Gly Cys Gly Ala |
| CP-MVP |
| SEQ ID NO: 19<br>Met Ala Gly Cys Gly Cys Pro Cys Gly Cys Gly Ala Met Ala Thr Glu Glu Phe |
| Ile Ile Arg Ile Pro Pro Tyr His Tyr Ile His Val Leu Asp Gln Asn Ser Asn |
| Val Ser Arg Val Glu Val Gly Pro Lys Thr Tyr Ile Arg Gln Asp Asn Glu Arg |
| Val Leu Phe Ala Pro Met Arg Met Val Thr Val Pro Pro Arg His Tyr Cys Thr |
| Val Ala Asn Pro Val Ser Arg Asp Ala Gln Gly Leu Val Leu Phe Asp Val Thr |
| Gly Gln Val Arg Leu Arg His Ala Asp Leu Glu Ile Arg Leu Ala Gln Asp Pro |

TABLE 1-continued

| Sequences |
| --- |
| Phe Pro Leu Tyr Pro Gly Glu Val Leu Glu Lys Asp Ile Thr Pro Leu Gln Val |
| Val Leu Pro Asn Thr Ala Leu His Leu Lys Ala Leu Leu Asp Phe Glu Asp Lys |
| Asp Gly Asp Lys Val Val Ala Gly Asp Glu Trp Leu Phe Glu Gly Pro Gly Thr |
| Tyr Ile Pro Arg Lys Glu Val Glu Val Val Glu Ile Ile Gln Ala Thr Ile Ile |
| Arg Gln Asn Gln Ala Leu Arg Leu Arg Ala Arg Lys Glu Cys Trp Asp Arg Asp |
| Gly Lys Glu Arg Val Thr Gly Glu Glu Trp Leu Val Thr Thr Val Gly Ala Tyr |
| Leu Pro Ala Val Phe Glu Glu Val Leu Asp Leu Val Asp Ala Val Ile Leu Thr |
| Glu Lys Thr Ala Leu His Leu Arg Ala Arg Arg Asn Phe Arg Asp Phe Arg Gly |
| Val Ser Arg Arg Thr Gly Glu Glu Trp Leu Val Thr Val Gln Asp Thr Glu Ala |
| His Val Pro Asp Val His Glu Glu Val Leu Gly Val Val Pro Ile Thr Thr Leu |
| Gly Pro His Asn Tyr Cys Val Ile Leu Asp Pro Val Gly Pro Asp Gly Lys Asn |
| Gln Leu Gly Gln Lys Arg Val Val Lys Gly Glu Lys Ser Phe Phe Leu Gln Pro |
| Gly Glu Gln Leu Glu Gln Gly Ile Gln Asp Val Tyr Val Leu Ser Glu Gln Gln |
| Gly Leu Leu Leu Arg Ala Leu Gln Pro Leu Glu Glu Gly Glu Asp Glu Glu Lys |
| Val Ser His Gln Ala Gly Asp His Trp Leu Ile Arg Gly Pro Leu Glu Tyr Val |
| Pro Ser Ala Lys Val Glu Val Val Glu Glu Arg Gln Ala Ile Pro Leu Asp Glu |
| Asn Glu Gly Ile Tyr Val Gln Asp Val Lys Thr Gly Lys Val Arg Ala Val Ile |
| Gly Ser Thr Tyr Met Leu Thr Gln Asp Glu Val Leu Trp Glu Lys Glu Leu Pro |
| Pro Gly Val Glu Glu Leu Leu Asn Lys Gly Gln Asp Pro Leu Ala Asp Arg Gly |
| Glu Lys Asp Thr Ala Lys Ser Leu Gln Pro Leu Ala Pro Arg Asn Lys Thr Arg |
| Val Val Ser Tyr Arg Val Pro His Asn Ala Ala Val Gln Val Tyr Asp Tyr Arg |
| Glu Lys Arg Ala Arg Val Val Phe Gly Pro Glu Leu Val Ser Leu Gly Pro Glu |
| Glu Gln Phe Thr Val Leu Ser Leu Ser Ala Gly Arg Pro Lys Arg Pro His Ala |
| Arg Arg Ala Leu Cys Leu Leu Leu Gly Pro Asp Phe Phe Thr Asp Val Ile Thr |
| Ile Glu Thr Ala Asp His Ala Arg Leu Gln Leu Gln Leu Ala Tyr Asn Trp His |
| Phe Glu Val Asn Asp Arg Lys Asp Pro Gln Glu Thr Ala Lys Leu Phe Ser Val |
| Pro Asp Phe Val Gly Asp Ala Cys Lys Ala Ile Ala Ser Arg Val Arg Gly Ala |
| Val Ala Ser Val Thr Phe Asp Asp Phe His Lys Asn Ser Ala Arg Ile Ile Arg |
| Thr Ala Val Phe Gly Phe Glu Thr Ser Glu Ala Lys Gly Pro Asp Gly Met Ala |
| Leu Pro Arg Pro Arg Asp Gln Ala Val Phe Pro Gln Asn Gly Leu Val Val Ser |
| Ser Val Asp Val Gln Ser Val Glu Pro Val Asp Gln Arg Thr Arg Asp Ala Leu |
| Gln Arg Ser Val Gln Leu Ala Ile Glu Ile Thr Thr Asn Ser Gln Glu Ala Ala |
| Ala Lys His Glu Ala Gln Arg Leu Glu Gln Glu Ala Arg Gly Arg Leu Glu Arg |
| Gln Lys Ile Leu Asp Gln Ser Glu Ala Glu Lys Ala Arg Lys Glu Leu Leu Glu |
| Leu Glu Ala Leu Ser Met Ala Val Glu Ser Thr Gly Thr Ala Lys Ala Glu Ala |
| Glu Ser Arg Ala Glu Ala Ala Arg Ile Glu Gly Glu Gly Ser Val Leu Gln Ala |
| Lys Leu Lys Ala Gln Ala Leu Ala Ile Glu Thr Glu Ala Glu Leu Gln Arg Val |
| Gln Lys Val Arg Glu Leu Glu Leu Val Tyr Ala Arg Ala Gln Leu Glu Leu Glu |
| Val Ser Lys Ala Gln Gln Leu Ala Glu Val Glu Val Lys Lys Phe Lys Gln Met |

TABLE 1-continued

| Sequences |
|---|
| Thr Glu Ala Ile Gly Pro Ser Thr Ile Arg Asp Leu Ala Val Ala Gly Pro Glu<br>Met Gln Val Lys Leu Leu Gln Ser Leu Gly Leu Lys Ser Thr Leu Ile Thr Asp<br>Gly Ser Thr Pro Ile Asn Leu Phe Asn Thr Ala Phe Gly Leu Leu Gly Met Gly<br>Pro Glu Gly Gln Pro Leu Gly Arg Arg Val Ala Ser Gly Pro Ser Pro Gly Glu<br>Gly Ile Ser Pro Gln Ser Ala Gln Ala Pro Gln Ala Pro Gly Asp Asn His Val<br>Val Pro Val Leu Arg |
| CP-MVP cDNA |
| SEQ ID NO: 20<br>atggcaggct gcggttgtcc atgcggttgt ggcgccatgg caactgaaga gttcatcatc<br>cgcatccccc cataccacta tatccatgtg ctggaccaga acagcaacgt gtcccgtgtg<br>gaggtcgggc caaagaccta catccggcag gacaatgaga gggtactgtt tgcccccatg<br>cgcatggtga ccgtcccccc acgtcactac tgcacagtgg ccaaccctgt gtctcgggat<br>gcccagggct tggtgctgtt tgatgtcaca gggcaagttc ggcttcgcca cgctgacctc<br>gagatccggc tggcccagga ccccttcccc ctgtacccag ggaggtgct ggaaaaggac<br>atcacacccc tgcaggtggt tctgcccaac actgccctcc atctaaaggc gctgcttgat<br>tttgaggata aagatggaga caaggtggtg gcaggagatg agtggctttt cgagggacct<br>ggcacgtaca tcccccggaa ggaagtggag gtcgtggaga tcattcaggc caccatcatc<br>aggcagaacc aggctctgcg gctcagggcc cgcaaggagt gctgggaccg ggacggcaag<br>gagagggtga caggggaaga atggctggtc accacagtag ggcgtacct cccagcggtg<br>tttgaggagg ttctggattt ggtggacgcc gtcatcctta cggaaaagac agccctgcac<br>ctccgggctc ggcggaactt ccgggacttc aggggagtgt cccgccgcac tggggaggag<br>tggctggtaa cagtgcagga cacagaggcc cacgtgccag atgtccacga ggaggtgctg<br>ggggttgtgc ccatcaccac cctgggcccc cacaactact gcgtgattct cgaccctgtc<br>ggaccggatg gcaagaatca gctggggcag aagcgcgtgg tcaagggaga gaagtctttt<br>ttcctccagc caggagagca gctggaacaa ggcatccagg atgtgtatgt gctgtcggag<br>cagcaggggc tgctgctgag ggccctgcag cccctggagg agggggagga tgaggagaag<br>gtctcacacc aggctgggga ccactggctc atccgcggac ccctggagta tgtgccatct<br>gccaaagtgg aggtggtgga ggagcgccag gccatccctc tagacgagaa cgagggcatc<br>tatgtgcagg atgtcaagac cggaaaggtg cgcgctgtga ttggaagcac ctacatgctg<br>acccaggacg aagtcctgtg ggagaaagag ctgcctcccg ggtggagga gctgctgaac<br>aaggggcagg accctctggc agacaggggt gagaaggaca cagctaagag cctccagccc<br>ttggcgcccc ggaacaagac ccgtgtggtc agctaccgcg tgccccacaa cgctgcggtg<br>caggtgtacg actaccgaga gaagcgagcc cgcgtggtct tcgggcctga gctggtgtcg<br>ctgggtcctg aggagcagtt cacagtgttg tccctctcag ctgggcggcc caagcgtccc<br>catgcccgcc gtgcgctctg cctgctgctg gggcctgact tcttcacaga cgtcatcacc<br>atcgaaacgg cggatcatgc caggctgcaa ctgcagctgg cctacaactg gcactttgag<br>gtgaatgacc ggaaggaccc ccaagagacg gccaagctct tttcagtgcc agactttgta<br>ggtgatgcct gcaaagccat cgcatcccgg gtgcgggggg ccgtggcctc tgtcactttc<br>gatgacttcc ataagaactc agcccgcatc attcgcactg ctgtctttgg ctttgagacc |

TABLE 1-continued

| Sequences |
|---|
| tcggaagcga agggccccga tggcatggcc ctgcccaggc cccgggacca ggctgtcttc |
| ccccaaaacg ggctggtggt cagcagtgtg gacgtgcagt cagtggagcc tgtggatcag |
| aggacccggg acgccctgca acgcagcgtc cagctggcca tcgagatcac caccaactcc |
| caggaagcgg cggccaagca tgaggctcag agactggagc aggaagcccg cggccggctt |
| gagcggcaga agatcctgga ccagtcagaa gccgagaaag ctcgcaagga acttttggag |
| ctggaggctc tgagcatggc cgtggagagc accgggactg ccaaggcgga ggccgagtcc |
| cgtgcggagg cagcccggat tgagggagaa gggtccgtgc tgcaggccaa gctaaaagca |
| caggccttgg ccattgaaac ggaggctgag ctccagaggg tccagaaggt ccgagagctg |
| gaactggtct atgcccgggc ccagctggag ctggaggtga gcaaggctca gcagctggct |
| gaggtggagg tgaagaagtt caagcagatg acagaggcca taggccccag caccatcagg |
| gaccttgctg tggctgggcc tgagatgcag gtaaaactgc tccagtccct gggcctgaaa |
| tcaaccctca tcaccgatgg ctccactccc atcaacctct tcaacacagc ctttgggctg |
| ctggggatgg ggcccgaggg tcagcccctg ggcagaaggg tggccagtgg gcccagccct |
| ggggagggga tatcccccca gtctgctcag gcccctcaag ctcctggaga caaccacgtg |
| gtgcctgtac tgcgctaa |
| TEP1, Genbank #AAC51107 |
| SEQ ID NO: 21 |
| Met Glu Lys Leu His Gly His Val Ser Ala His Pro Asp Ile Leu Ser Leu Glu |
| Asn Arg Cys Leu Ala Met Leu Pro Asp Leu Gln Pro Leu Glu Lys Leu His Gln |
| His Val Ser Thr His Ser Asp Ile Leu Ser Leu Lys Asn Gln Cys Leu Ala Thr |
| Leu Pro Asp Leu Lys Thr Met Glu Lys Pro His Gly Tyr Val Ser Ala His Pro |
| Asp Ile Leu Ser Leu Glu Asn Gln Cys Leu Ala Thr Leu Ser Asp Leu Lys Thr |
| Met Glu Lys Pro His Gly His Val Ser Ala His Pro Asp Ile Leu Ser Leu Glu |
| Asn Arg Cys Leu Ala Thr Leu Pro Ser Leu Lys Ser Thr Val Ser Ala Ser Pro |
| Leu Phe Gln Ser Leu Gln Ile Ser His Met Thr Gln Ala Asp Leu Tyr Arg Val |
| Asn Asn Ser Asn Cys Leu Leu Ser Glu Pro Pro Ser Trp Arg Ala Gln His Phe |
| Ser Lys Gly Leu Asp Leu Ser Thr Cys Pro Ile Ala Leu Lys Ser Ile Ser Ala |
| Thr Glu Thr Ala Gln Glu Ala Thr Leu Gly Arg Trp Phe Asp Ser Glu Glu Lys |
| Lys Gly Ala Glu Thr Gln Met Pro Ser Tyr Ser Leu Ser Leu Gly Glu Glu Glu |
| Glu Val Glu Asp Leu Ala Val Lys Leu Thr Ser Gly Asp Ser Glu Ser His Pro |
| Glu Pro Thr Asp His Val Leu Gln Glu Lys Lys Met Ala Leu Leu Ser Leu Leu |
| Cys Ser Thr Leu Val Ser Glu Val Asn Met Asn Asn Thr Ser Asp Pro Thr Leu |
| Ala Ala Ile Phe Glu Ile Cys Arg Glu Leu Ala Leu Leu Glu Pro Glu Phe Ile |
| Leu Lys Ala Ser Leu Tyr Ala Arg Gln Gln Leu Asn Val Arg Asn Val Ala Asn |
| Asn Ile Leu Ala Ile Ala Ala Phe Leu Pro Ala Cys Arg Pro His Leu Arg Arg |
| Tyr Phe Cys Ala Ile Val Gln Leu Pro Ser Asp Trp Ile Gln Val Ala Glu Leu |
| Tyr Gln Ser Leu Ala Glu Gly Asp Lys Asn Lys Leu Val Pro Leu Pro Ala Cys |
| Leu Arg Thr Ala Met Thr Asp Lys Phe Ala Gln Phe Asp Glu Tyr Gln Leu Ala |
| Lys Tyr Asn Pro Arg Lys His Arg Ala Lys Arg His Pro Arg Arg Pro Pro Arg |
| Ser Pro Gly Met Glu Pro Pro Phe Ser His Arg Cys Phe Pro Arg Tyr Ile Gly |

TABLE 1-continued

| Sequences |
|---|
| Phe Leu Arg Glu Glu Gln Arg Lys Phe Glu Lys Ala Gly Asp Thr Val Ser Glu |
| Lys Lys Asn Pro Pro Arg Phe Thr Leu Lys Lys Leu Val Gln Arg Leu His Ile |
| His Lys Pro Ala Gln His Val Gln Ala Leu Leu Gly Tyr Arg Tyr Pro Ser Asn |
| Leu Gln Leu Phe Ser Arg Ser Arg Leu Pro Gly Pro Trp Asp Ser Ser Arg Ala |
| Gly Lys Arg Met Lys Leu Ser Arg Pro Glu Thr Trp Glu Arg Glu Leu Ser Leu |
| Arg Gly Asn Lys Ala Ser Val Trp Glu Glu Leu Ile Glu Asn Gly Lys Leu Pro |
| Phe Met Ala Met Leu Arg Asn Leu Cys Asn Leu Leu Arg Val Gly Ile Ser Ser |
| Arg His His Glu Leu Ile Leu Gln Arg Leu Gln His Gly Lys Ser Val Ile His |
| Ser Arg Gln Phe Pro Phe Arg Phe Leu Asn Ala His Asp Ala Ile Asp Ala Leu |
| Glu Ala Gln Leu Arg Asn Gln Ala Leu Pro Phe Pro Ser Asn Ile Thr Leu Met |
| Arg Arg Ile Leu Thr Arg Asn Glu Lys Asn Arg Pro Arg Arg Arg Phe Leu Cys |
| His Leu Ser Arg Gln Gln Leu Arg Met Ala Met Arg Ile Pro Val Leu Tyr Glu |
| Gln Leu Lys Arg Glu Lys Leu Arg Val His Lys Ala Arg Gln Trp Lys Tyr Asp |
| Gly Glu Met Leu Asn Arg Tyr Arg Gln Ala Leu Glu Thr Ala Val Asn Leu Ser |
| Val Lys His Ser Leu Pro Leu Leu Pro Gly Arg Thr Val Leu Val Tyr Leu Thr |
| Asp Ala Asn Ala Asp Arg Leu Cys Pro Lys Ser Asn Pro Gln Gly Pro Pro Leu |
| Asn Tyr Ala Leu Leu Leu Ile Gly Met Met Ile Thr Arg Ala Glu Gln Val Asp |
| Val Val Leu Cys Gly Gly Asp Thr Leu Lys Thr Ala Val Leu Lys Ala Glu Glu |
| Gly Ile Leu Lys Thr Ala Ile Lys Leu Gln Ala Gln Val Gln Glu Phe Asp Glu |
| Asn Asp Gly Trp Ser Leu Asn Thr Phe Gly Lys Tyr Leu Leu Ser Leu Ala Gly |
| Gln Arg Val Pro Val Asp Arg Val Ile Leu Leu Gly Gln Ser Met Asp Asp Gly |
| Met Ile Asn Val Ala Lys Gln Leu Tyr Trp Gln Arg Val Asn Ser Lys Cys Leu |
| Phe Val Gly Ile Leu Leu Arg Arg Val Gln Tyr Leu Ser Thr Asp Leu Asn Pro |
| Asn Asp Val Thr Leu Ser Gly Cys Thr Asp Ala Ile Leu Lys Phe Ile Ala Glu |
| His Gly Ala Ser His Leu Leu Glu His Val Gly Gln Met Asp Lys Ile Phe Lys |
| Ile Pro Pro Pro Pro Gly Lys Thr Gly Val Gln Ser Leu Arg Pro Leu Glu Glu |
| Asp Thr Pro Ser Pro Leu Ala Pro Val Ser Gln Gln Gly Trp Arg Ser Ile Arg |
| Leu Phe Ile Ser Ser Thr Phe Arg Asp Met His Gly Glu Arg Asp Leu Leu Leu |
| Arg Ser Val Leu Pro Ala Leu Gln Ala Arg Ala Ala Pro His Arg Ile Ser Leu |
| His Gly Ile Asp Leu Arg Trp Gly Val Thr Glu Glu Glu Thr Arg Arg Asn Arg |
| Gln Leu Glu Val Cys Leu Gly Glu Val Glu Asn Ala Gln Leu Phe Val Gly Ile |
| Leu Gly Ser Arg Tyr Gly Tyr Ile Pro Pro Ser Tyr Asn Leu Pro Asp His Pro |
| His Phe His Trp Ala Gln Gln Tyr Pro Ser Gly Arg Ser Val Thr Glu Met Glu |
| Val Met Gln Phe Leu Asn Arg Asn Gln Arg Leu Gln Pro Ser Ala Gln Ala Leu |
| Ile Tyr Phe Arg Asp Ser Ser Phe Leu Ser Ser Val Pro Asp Ala Trp Lys Ser |
| Asp Phe Val Ser Glu Ser Glu Glu Ala Ala Cys Arg Ile Ser Glu Leu Lys Ser |
| Tyr Leu Ser Arg Gln Lys Gly Ile Thr Cys Arg Arg Tyr Pro Cys Glu Trp Gly |
| Gly Val Ala Ala Gly Arg Pro Tyr Val Gly Gly Leu Glu Glu Phe Gly Gln Leu |
| Val Leu Gln Asp Val Trp Asn Met Ile Gln Lys Leu Tyr Leu Gln Pro Gly Ala |

TABLE 1-continued

| Sequences |
| --- |
| Leu Leu Glu Gln Pro Val Ser Ile Pro Asp Asp Asp Leu Val Gln Ala Thr Phe |
| Gln Gln Leu Gln Lys Pro Pro Ser Pro Ala Arg Pro Arg Leu Leu Gln Asp Thr |
| Val Gln Gln Leu Met Leu Pro His Gly Arg Leu Ser Leu Val Thr Gly Gln Ser |
| Gly Gln Gly Lys Thr Ala Phe Leu Ala Ser Leu Val Ser Ala Leu Gln Ala Pro |
| Asp Gly Ala Lys Val Ala Pro Leu Val Phe Phe His Phe Ser Gly Ala Arg Pro |
| Asp Gln Gly Leu Ala Leu Thr Leu Leu Arg Arg Leu Cys Thr Tyr Leu Arg Gly |
| Gln Leu Lys Glu Pro Gly Ala Leu Pro Ser Thr Tyr Arg Ser Leu Val Trp Glu |
| Leu Gln Gln Arg Leu Leu Pro Lys Ser Ala Glu Ser Leu His Pro Gly Gln Thr |
| Gln Val Leu Ile Ile Asp Gly Ala Asp Arg Leu Val Asp Gln Asn Gly Gln Leu |
| Ile Ser Asp Trp Ile Pro Lys Lys Leu Pro Arg Cys Val His Leu Val Leu Ser |
| Val Ser Ser Asp Ala Gly Leu Gly Glu Thr Leu Glu Gln Ser Gln Gly Ala His |
| Val Leu Ala Leu Gly Pro Leu Glu Ala Ser Ala Arg Ala Arg Leu Val Arg Glu |
| Glu Leu Ala Leu Tyr Gly Lys Arg Leu Glu Glu Ser Pro Phe Asn Asn Gln Met |
| Arg Leu Leu Leu Val Lys Arg Glu Ser Gly Arg Pro Leu Tyr Leu Arg Leu Val |
| Thr Asp His Leu Arg Leu Phe Thr Leu Tyr Glu Gln Val Ser Glu Arg Leu Arg |
| Thr Leu Pro Ala Thr Val Pro Leu Leu Leu Gln His Ile Leu Ser Thr Leu Glu |
| Lys Glu His Gly Pro Asp Val Leu Pro Gln Ala Leu Thr Ala Leu Glu Val Thr |
| Arg Ser Gly Leu Thr Val Asp Gln Leu His Gly Val Leu Ser Val Trp Arg Thr |
| Leu Pro Lys Gly Thr Lys Ser Trp Glu Glu Ala Val Ala Ala Gly Asn Ser Gly |
| Asp Pro Tyr Pro Met Gly Pro Phe Ala Cys Leu Val Gln Ser Leu Arg Ser Leu |
| Leu Gly Glu Gly Pro Leu Glu Arg Pro Gly Ala Arg Leu Cys Leu Pro Asp Gly |
| Pro Leu Arg Thr Ala Ala Lys Arg Cys Tyr Gly Lys Arg Pro Gly Leu Glu Asp |
| Thr Ala His Ile Leu Ile Ala Ala Gln Leu Trp Lys Thr Cys Asp Ala Asp Ala |
| Ser Gly Thr Phe Arg Ser Cys Pro Pro Glu Ala Leu Gly Asp Leu Pro Tyr His |
| Leu Leu Gln Ser Gly Asn Arg Gly Leu Leu Ser Lys Phe Leu Thr Asn Leu His |
| Val Val Ala Ala His Leu Glu Leu Gly Leu Val Ser Arg Leu Leu Glu Ala His |
| Ala Leu Tyr Ala Ser Ser Val Pro Lys Glu Glu Gln Lys Leu Pro Glu Ala Asp |
| Val Ala Val Phe Arg Thr Phe Leu Arg Gln Gln Ala Ser Ile Leu Ser Gln Tyr |
| Pro Arg Leu Leu Pro Gln Gln Ala Ala Asn Gln Pro Leu Asp Ser Pro Leu Cys |
| His Gln Ala Ser Leu Leu Ser Arg Arg Trp His Leu Gln His Thr Leu Arg Trp |
| Leu Asn Lys Pro Arg Thr Met Lys Asn Gln Gln Ser Ser Ser Leu Ser Leu Ala |
| Val Ser Ser Ser Pro Thr Ala Val Ala Phe Ser Thr Asn Gly Gln Arg Ala Ala |
| Val Gly Thr Ala Asn Gly Thr Val Tyr Leu Leu Asp Leu Arg Thr Trp Gln Glu |
| Glu Lys Ser Val Val Ser Gly Cys Asp Gly Ile Ser Ala Cys Leu Phe Leu Ser |
| Asp Asp Thr Leu Phe Leu Thr Ala Phe Asp Gly Leu Leu Glu Leu Trp Asp Leu |
| Gln His Gly Cys Arg Val Leu Gln Thr Lys Ala His Gln Tyr Gln Ile Thr Gly |
| Cys Cys Leu Ser Pro Asp Cys Arg Leu Leu Ala Thr Val Cys Leu Gly Gly Cys |
| Leu Lys Leu Trp Asp Thr Val Arg Gly Gln Leu Ala Phe Gln His Thr Tyr Pro |
| Lys Ser Leu Asn Cys Val Ala Phe His Pro Glu Gly Gln Val Ile Ala Thr Gly |

TABLE 1-continued

| Sequences |
|---|
| Ser Trp Ala Gly Ser Ile Ser Phe Phe Gln Val Asp Gly Leu Lys Val Thr Lys |
| Asp Leu Gly Ala Pro Gly Ala Ser Ile Arg Thr Leu Ala Phe Asn Val Pro Gly |
| Gly Val Val Ala Val Gly Arg Leu Asp Ser Met Val Glu Leu Trp Ala Trp Arg |
| Glu Gly Ala Arg Leu Ala Ala Phe Pro Ala His His Gly Phe Val Ala Ala Ala |
| Leu Phe Leu His Ala Gly Cys Gln Leu Leu Thr Ala Gly Glu Asp Gly Lys Val |
| Gln Val Trp Ser Gly Ser Leu Gly Arg Pro Arg Gly His Leu Gly Ser Leu Ser |
| Leu Ser Pro Ala Leu Ser Val Ala Leu Ser Pro Asp Gly Asp Arg Val Ala Val |
| Gly Tyr Arg Ala Asp Gly Ile Arg Ile Tyr Lys Ile Ser Ser Gly Ser Gln Gly |
| Ala Gln Gly Gln Ala Leu Asp Val Ala Val Ser Ala Leu Ala Trp Leu Ser Pro |
| Lys Val Leu Val Ser Gly Ala Glu Asp Gly Ser Leu Gln Gly Trp Ala Leu Lys |
| Glu Cys Ser Leu Gln Ser Leu Trp Leu Leu Ser Arg Phe Gln Lys Pro Val Leu |
| Gly Leu Ala Thr Ser Gln Glu Leu Leu Ala Ser Ala Ser Glu Asp Phe Thr Val |
| Gln Leu Trp Pro Arg Gln Leu Leu Thr Arg Pro His Lys Ala Glu Asp Phe Pro |
| Cys Gly Thr Glu Leu Arg Gly His Glu Gly Pro Val Ser Cys Cys Ser Phe Ser |
| Thr Asp Gly Gly Ser Leu Ala Thr Gly Gly Arg Asp Arg Ser Leu Leu Cys Trp |
| Asp Val Arg Thr Pro Lys Thr Pro Val Leu Ile His Ser Phe Pro Ala Cys His |
| Arg Asp Trp Val Thr Gly Cys Ala Trp Thr Lys Asp Asn Leu Leu Ile Ser Cys |
| Ser Ser Asp Gly Ser Val Gly Leu Trp Asp Pro Glu Ser Gly Gln Arg Leu Gly |
| Gln Phe Leu Gly His Gln Ser Ala Val Ser Ala Val Ala Ala Val Glu Glu His |
| Val Val Ser Val Ser Arg Asp Gly Thr Leu Lys Val Trp Asp His Gln Gly Val |
| Glu Leu Thr Ser Ile Pro Ala His Ser Gly Pro Ile Ser His Cys Ala Ala Ala |
| Met Glu Pro Arg Ala Ala Gly Gln Pro Gly Ser Glu Leu Leu Val Val Thr Val |
| Gly Leu Asp Gly Ala Thr Arg Leu Trp His Pro Leu Leu Val Cys Gln Thr His |
| Thr Leu Leu Gly His Ser Gly Pro Val Arg Ala Ala Ala Val Ser Glu Thr Ser |
| Gly Leu Met Leu Thr Ala Ser Glu Asp Gly Ser Val Arg Leu Trp Gln Val Pro |
| Lys Glu Ala Asp Asp Thr Cys Ile Pro Arg Ser Ser Ala Ala Val Thr Ala Val |
| Ala Trp Ala Pro Asp Gly Ser Met Ala Val Ser Gly Asn Gln Ala Gly Glu Leu |
| Ile Leu Trp Gln Glu Ala Lys Ala Val Ala Thr Ala Gln Ala Pro Gly His Ile |
| Gly Ala Leu Ile Trp Ser Ser Ala His Thr Phe Phe Val Leu Ser Ala Asp Glu |
| Lys Ile Ser Glu Trp Gln Val Lys Leu Arg Lys Gly Ser Ala Pro Gly Asn Leu |
| Ser Leu His Leu Asn Arg Ile Leu Gln Glu Asp Leu Gly Val Leu Thr Ser Leu |
| Asp Trp Ala Pro Asp Gly His Phe Leu Ile Leu Ala Lys Ala Asp Leu Lys Leu |
| Leu Cys Met Lys Pro Gly Asp Ala Pro Ser Glu Ile Trp Ser Ser Tyr Thr Glu |
| Asn Pro Met Ile Leu Ser Thr His Lys Glu Tyr Gly Ile Phe Val Leu Gln Pro |
| Lys Asp Pro Gly Val Leu Ser Phe Leu Arg Gln Lys Glu Ser Gly Glu Phe Glu |
| Glu Arg Leu Asn Phe Asp Ile Asn Leu Glu Asn Pro Ser Arg Thr Leu Ile Ser |
| Ile Thr Gln Ala Lys Pro Glu Ser Glu Ser Ser Phe Leu Cys Ala Ser Ser Asp |
| Gly Ile Leu Trp Asn Leu Ala Lys Cys Ser Pro Glu Gly Glu Trp Thr Thr Gly |
| Asn Met Trp Gln Lys Lys Ala Asn Thr Pro Glu Thr Gln Thr Pro Gly Thr Asp |

TABLE 1-continued

| Sequences |
|---|
| Pro Ser Thr Cys Arg Glu Ser Asp Ala Ser Met Asp Ser Asp Ala Ser Met Asp |
| Ser Glu Pro Thr Pro His Leu Lys Thr Arg Gln Arg Arg Lys Ile His Ser Gly |
| Ser Val Thr Ala Leu His Val Leu Pro Glu Leu Leu Val Thr Ala Ser Lys Asp |
| Arg Asp Val Lys Leu Trp Glu Arg Pro Ser Met Gln Leu Leu Gly Leu Phe Arg |
| Cys Glu Gly Ser Val Ser Cys Leu Glu Pro Trp Leu Gly Ala Asn Ser Thr Leu |
| Gln Leu Ala Val Gly Asp Val Gln Gly Asn Val Tyr Phe Leu Asn Trp Glu |
| TEP1 cDNA, Genbank #U86136 |
| SEQ ID NO: 22 |
| atggaaaaac tccatgggca tgtgtctgcc catccagaca tcctctcctt ggagaaccgg |
| tgcctggcta tgctccctga cttacagccc ttggagaaac tacatcagca tgtatctacc |
| cactcagata tcctctcctt gaagaaccag tgcctagcca cgcttcctga cctgaagacc |
| atggaaaaac cacatggata tgtgtctgcc cacccagaca tcctctcctt ggagaaccag |
| tgcctggcca cactttctga cctgaagacc atggagaaac cacatggaca tgtttctgcc |
| cacccagaca tcctctcctt ggagaaccgg tgcctggcca ccctccctag tctaaagagc |
| actgtgtctg ccagcccctt gttccagagt ctacagatat ctcacatgac gcaagctgat |
| ttgtaccgtg tgaacaacag caattgcctg ctctctgagc ctccaagttg gagggctcag |
| catttctcta agggactaga cctttcaacc tgccctatag ccctgaaatc catctctgcc |
| acagagacag ctcaggaagc aactttgggt cgttggtttg attcagaaga gaagaaaggg |
| gcagagaccc aaatgccttc ttatagtctg agcttgggag aggaggagga ggtggaggat |
| ctggccgtga agctcacctc tggagactct gaatctcatc cagagcctac tgaccatgtc |
| cttcaggaaa agaagatggc tctactgagc ttgctgtgct ctactctggt ctcagaagta |
| aacatgaaca atacatctga ccccaccctg gctgccattt ttgaaatctg tcgtgaactt |
| gccctcctgg agcctgagtt tatcctcaag gcatctttgt atgccaggca gcagctgaac |
| gtccggaatg tggccaataa catcttggcc attgctgctt tcttgccggc gtgtcgcccc |
| cacctgcgac gatatttctg tgccattgtc cagctgcctt ctgactggat ccaggtggct |
| gagctttacc agagcctggc tgagggagat aagaataagc tggtgcccct gcccgcctgt |
| ctccgtactg ccatgacgga caaatttgcc cagtttgacg agtaccagct ggctaagtac |
| aaccctcgga agcaccgggc caagagacac ccccgccggc cacccgctc tccagggatg |
| gagcctccat tttctcacag atgttttcca aggtacatag ggtttctcag agaagagcag |
| agaaagtttg agaaggccgg tgatacagtg tcagagaaaa agaatcctcc aaggttcacc |
| ctgaagaagc tggttcagcg actgcacatc cacaagcctg cccagcacgt tcaagccctg |
| ctgggttaca gatacccctc caacctacag ctcttttctc gaagtcgcct tcctgggcct |
| tgggattcta gcagagctgg gaagaggatg aagctgtcta ggccagagac ctgggagcgg |
| gagctgagcc tacgggggaa caaagcgtcg gtctgggagg aactcattga aaatgggaag |
| cttcccttca tggccatgct tcggaacctg tgcaacctgc tgcgggttgg aatcagttcc |
| cgccaccatg agctcattct ccagagactc cagcatggga agtcggtgat ccacagtcgg |
| cagtttccat tcagatttct taacgcccat gatgccattg atgccctcga ggctcaactc |
| agaaatcaag cattgccctt tccttcgaat ataacactga tgaggcggat actaactaga |
| aatgaaaaga accgtcccag gcggaggttt ctttgccacc taagccgtca gcagcttcgt |

TABLE 1-continued

| Sequences |
| --- |
| atggcaatga ggatacctgt gttgtatgag cagctcaaga gggagaagct gagagtacac |
| aaggccagac agtggaaata tgatggtgag atgctgaaca ggtaccgaca ggccctagag |
| acagctgtga acctctctgt gaagcacagc ctgcccctgc tgccaggccg cactgtcttg |
| gtctatctga cagatgctaa tgcagacagg ctctgtccaa agagcaaccc acaagggccc |
| ccgctgaact atgcactgct gttgattggg atgatgatca cgagggcgga gcaggtggac |
| gtcgtgctgt gtggaggtga cactctgaag actgcagtgc ttaaggcaga agaaggcatc |
| ctgaagactg ccatcaagct ccaggctcaa gtccaggagt ttgatgaaaa tgatggatgg |
| tccctgaata cttttgggaa atacctgctg tctctggctg gccaaagggt tcctgtggac |
| agggtcatcc tccttggcca aagcatggat gatggaatga taaatgtggc caaacagctt |
| tactggcagc gtgtgaattc caagtgcctc tttgttggta tcctcctaag aagggtacaa |
| tacctgtcaa cagatttgaa tcccaatgat gtgacactct caggctgtac tgatgcgata |
| ctgaagttca ttgcagagca tggggcctcc catcttctgg aacatgtggg ccaaatggac |
| aaaatattca agattccacc acccccagga aagacagggg tccagtctct ccggccactg |
| gaagaggaca ctccaagccc cttggctcct gtttcccagc aaggatggcg cagcatccgg |
| cttttcattt catccacttt ccgagacatg cacggggagc gggacctgct gctgaggtct |
| gtgctgccag cactgcaggc ccgagcggcc cctcaccgta tcagccttca cggaatcgac |
| ctccgctggg gcgtcactga ggaggagacc cgtaggaaca gacaactgga agtgtgcctt |
| ggggaggtgg agaacgcaca gctgtttgtg gggattctgg gctcccgtta tggatacatt |
| ccccccagct acaaccttcc tgaccatcca cacttccact gggcccagca gtacccttca |
| gggcgctctg tgacagagat ggaggtgatg cagttcctga accggaacca acgtctgcag |
| ccctctgccc aagctctcat ctacttccgg gattccagct tcctcagctc tgtgccagat |
| gcctggaaat ctgactttgt ttctgagtct gaagaggccg catgtcggat ctcagaactg |
| aagagctacc taagcagaca gaaagggata acctgccgca gatacccctg tgagtggggg |
| ggtgtggcag ctggccggcc ctatgttggc gggctggagg agtttgggca gttggttctg |
| caggatgtat ggaatatgat ccagaagctc tacctgcagc ctggggccct gctggagcag |
| ccagtgtcca tcccagacga tgacttggtc caggccacct tccagcagct gcagaagcca |
| ccgagtcctg cccggccacg ccttcttcag gacacagtgc aacagctgat gctgccccac |
| ggaaggctga gcctggtgac ggggcagtca ggacagggca agacagcctt cctggcatct |
| cttgtgtcag ccctgcaggc tcctgatggg gccaaggtgg caccattagt cttcttccac |
| ttttctgggg ctcgtcctga ccagggtctt gccctcactc tgctcagacg cctctgtacc |
| tatctgcgtg gccaactaaa agagccaggt gccctcccca gcacctaccg aagcctggtg |
| tgggagctgc agcagaggct gctgcccaag tctgctgagt ccctgcatcc tggccagacc |
| caggtcctga tcatcgatgg ggctgatagg ttagtggacc agaatgggca gctgatttca |
| gactggatcc caaagaagct tccccggtgt gtacacctgg tgctgagtgt gtctagtgat |
| gcaggcctag gggagaccct tgagcagagc cagggtgccc acgtgctggc cttggggcct |
| ctggaggcct ctgctcgggc ccggctggtg agagaggagc tggccctgta cgggaagcgg |
| ctggaggagt caccatttaa caaccagatg cgactgctgc tggtgaagcg ggaatcaggc |
| cggccgctct acctgcgctt ggtcaccgat cacctgaggc tcttcacgct gtatgagcag |
| gtgtctgaga gactccggac cctgcctgcc actgtccccc tgctgctgca gcacatcctg |

TABLE 1-continued

| Sequences |
|---|
| agcacactgg agaaggagca cgggcctgat gtccttcccc aggccttgac tgccctagaa |
| gtcacacgga gtggtttgac tgtggaccag ctgcacggag tgctgagtgt gtggcggaca |
| ctaccgaagg ggactaagag ctgggaagaa gcagtggctg ctggtaacag tggagacccc |
| taccccatgg gcccgtttgc ctgcctcgtc cagagtctgc gcagtttgct aggggagggc |
| cctctggagc gccctggtgc ccggctgtgc ctccctgatg ggcccctgag aacagcagct |
| aaacgttgct atgggaagag gccagggcta gaggacacgg cacacatcct cattgcagct |
| cagctctgga agacatgtga cgctgatgcc tcaggcacct tccgaagttg ccctcctgag |
| gctctgggag acctgcctta ccacctgctc cagagcggga accgtggact tctttcgaag |
| ttccttacca acctccatgt ggtggctgca cacttggaat tgggtctggt ctctcggctc |
| ttggaggccc atgccctcta tgcttcttca gtccccaaag aggaacaaaa gctccccgag |
| gctgacgttg cagtgtttcg caccttcctg aggcagcagg cttcaatcct cagccagtac |
| ccccggctcc tgccccagca ggcagccaac cagcccctgg actcacctct ttgccaccaa |
| gcctcgctgc tctcccggag atggcacctc caacacacac tacgatggct taataaaccc |
| cggaccatga aaaatcagca aagctccagc ctgtctctgg cagtttcctc atcccctact |
| gctgtggcct tctccaccaa tgggcaaaga gcagctgtgg gcactgccaa tgggacagtt |
| tacctgttgg acctgagaac ttggcaggag gagaagtctg tggtgagtgg ctgtgatgga |
| atctctgctt gtttgttcct ctccgatgat acactctttc ttactgcctt cgacgggctc |
| ctggagctct gggacctgca gcatggttgt cgggtgctgc agactaaggc tcaccagtac |
| caaatcactg gctgctgcct gagcccagac tgccggctgc tagccaccgt gtgcttggga |
| ggatgcctaa agctgtggga cacagtccgt gggcagctgg ccttccagca cacctacccc |
| aagtccctga actgtgttgc cttccaccca gaggggcagg taatagccac aggcagctgg |
| gctggcagca tcagcttctt ccaggtggat gggctcaaag tcaccaagga cctgggggca |
| cccggagcct ctatccgtac cttggccttc aatgtgcctg ggggggttgt ggctgtgggc |
| cggctggaca gtatggtgga gctgtgggcc tggcgagaag ggcacggct ggctgccttc |
| cctgcccacc atggctttgt tgctgctgcg cttttcctgc atgcgggttg ccagttactg |
| acggctggag aggatggcaa ggttcaggtg tggtcagggt ctctgggtcg gccccgtggg |
| cacctgggtt ccctttctct ctctcctgcc ctctctgtgg cactcagccc agatggtgat |
| cgggtggctg ttggatatcg agcggatggc attaggatct acaaaatctc ttcaggttcc |
| cagggggctc agggtcaggc actggatgtg gcagtgtccg ccctggcctg gctaagcccc |
| aaggtattgg tgagtggtgc agaagatggg tccttgcagg gctgggcact caaggaatgc |
| tcccttcagt ccctctggct cctgtccaga ttccagaagc ctgtgctagg actggccact |
| tcccaggagc tcttggcttc tgcctcagag gatttcacag tgcagctgtg gccaaggcag |
| ctgctgacgc ggccacacaa ggcagaagac tttccctgtg gcactgagct gcggggacat |
| gagggccctg tgagctgctg tagtttcagc actgatggag gcagcctggc caccgggggc |
| cgggatcgga gtctcctctg ctgggacgtg aggacaccca aaacccctgt tttgatccac |
| tccttccctg cctgtcaccg tgactgggtc actggctgtg cctggaccaa agataaccta |
| ctgatatcct gctccagtga tggctctgtg gggctctggg acccagagtc aggacagcgg |
| cttggtcagt tcctgggtca tcagagtgct gtgagcgctg tggcagctgt ggaggagcac |
| gtggtgtctg tgagccggga tgggaccttg aaagtgtggg accatcaagg cgtggagctg |

TABLE 1-continued

| Sequences |
|---|
| accagcatcc ctgctcactc aggacccatt agccactgtg cagctgccat ggagccccgt |
| gcagctggac agcctgggtc agagcttctg gtggtaaccg tcgggctaga tggggccaca |
| cggttatggc atccactctt ggtgtgccaa acccacaccc tcctgggaca cagcggccca |
| gtccgtgctg ctgctgtttc agaaacctca ggcctcatgc tgaccgcctc tgaggatggt |
| tctgtacggc tctggcaggt tcctaaggaa gcagatgaca catgtatacc aaggagttct |
| gcagccgtca ctgctgtggc ttgggcacca gatggttcca tggcagtatc tggaaatcaa |
| gctggggaac taatcttgtg gcaggaagct aaggctgtgg ccacagcaca ggctccaggc |
| cacattggtg ctctgatctg gtcctcggca cacacctttt ttgtcctcag tgctgatgag |
| aaaatcagcg agtggcaagt gaaactgcgg aagggttcgg cacccggaaa tttgagtctt |
| cacctgaacc gaattctaca ggaggactta ggggtgctga caagtctgga ttgggctcct |
| gatggtcact ttctcatctt ggccaaagca gatttgaagt tactttgcat gaagccaggg |
| gatgctccat ctgaaatctg gagcagctat acagaaaatc ctatgatatt gtccacccac |
| aaggagtatg gcatatttgt cctgcagccc aaggatcctg gagttctttc tttcttgagg |
| caaaaggaat caggagagtt tgaagagagg ctgaactttg atataaactt agagaatcct |
| agtaggaccc taatatcgat aactcaagcc aaacctgaat ctgagtcctc atttttgtgt |
| gccagctctg atgggatcct atggaacctg gccaaatgca gcccagaagg agaatggacc |
| acaggtaaca tgtggcagaa aaaagcaaac actccagaaa cccaaactcc agggacagac |
| ccatctacct gcagggaatc tgatgccagc atggatagtg atgccagcat ggatagtgag |
| ccaacaccac atctaaagac acggcagcgt agaaagattc actcgggctc tgtcacagcc |
| ctccatgtgc tacctgagtt gctggtgaca gcttcgaagg acagagatgt taagctatgg |
| gagagaccca gtatgcagct gctgggcctg ttccgatgcg aagggtcagt gagctgcctg |
| gaaccttggc tgggcgctaa ctccaccctg cagcttgccg tgggagacgt gcagggcaat |
| gtgtactttc tgaattggga atga |
| vRNA, Genbank #AF045143 |
| SEQ ID NO: 23 |
| ggcuggcuuu agcucagcgg uuacuucgac aguucuuuaa uugaaacaag caaccugucu |
| ggguuguucg agacccgcgg gcgcucucca guccuuuu |
| vRNA, Genbank #AF045144 |
| SEQ ID NO: 24 |
| ggcuggcuuu agcucagcgg uuacuucgag uacauuguaa ccaccucucu ggguggUucg |
| agacccgcgg gugcuuucca gcucuuuu |
| vRNA, Genbank #AF045145 |
| SEQ ID NO: 25 |
| ggcuggcuuu agcucagcgg uuacuucgcg ugucaucaaa ccaccucucu ggguuguucg |
| agacccgcgg gcgcucucca gcccucuu |
| mCherry nucleotide sequence |
| SEQ ID NO: 26 |
| ATGGTGAGCA AGGGCGAGGA GGATAACATG GCCATCATCA AGGAGTTCAT GCGCTTCAAG |
| GTGCACATGG AGGGCTCCGT GAACGGCCAC GAGTTCGAGA TCGAGGGCGA GGGCGAGGGC |
| CGCCCCTACG AGGGCACCCA GACCGCCAAG CTGAAGGTGA CCAAGGGTGG CCCCCTGCCC |
| TTCGCCTGGG ACATCCTGTC CCCTCAGTTC ATGTACGGCT CCAAGGCCTA CGTGAAGCAC |

TABLE 1-continued

| Sequences |
|---|
| CCCGCCGACA TCCCCGACTA CTTGAAGCTG TCCTTCCCCG AGGGCTTCAA GTGGGAGCGC |
| GTGATGAACT TCGAGGACGG CGGCGTGGTG ACCGTGACCC AGGACTCCTC CCTGCAGGAC |
| GGCGAGTTCA TCTACAAGGT GAAGCTGCGC GGCACCAACT TCCCCTCCGA CGGCCCCGTA |
| ATGCAGAAGA AGACCATGGG CTGGGAGGCC TCCTCCGAGC GGATGTACCC CGAGGACGGC |
| GCCCTGAAGG GCGAGATCAA GCAGAGGCTG AAGCTGAAGG ACGGCGGCCA CTACGACGCT |
| GAGGTCAAGA CCACCTACAA GGCCAAGAAG CCCGTGCAGC TGCCCGGCGC CTACAACGTC |
| AACATCAAGT TGGACATCAC CTCCCACAAC GAGGACTACA CCATCGTGGA ACAGTACGAA |
| CGCGCCGAGG GCCGCCACTC CACCGGCGGC ATGGACGAGC TGTACAAGTA A |
| mCherry amino acid sequence |
| SEQ ID NO: 27 |
| MVSKGEEDNMAIIKEFMRFKVHMEGSVNGHEFEIEGEGEGRPYEGTQTAKLKVTKGGPLPFAWDILSPQFMYG |
| SKAYVKHPADIPDYLKLSFPEGFKWERVMNFEDGGVVTVTQDSSLQDGEFIYKVKLRGTNFPSDGPVMQKKTM |
| GWEASSERMYPEDGALKGEIKQRLKLKDGGHYDAEVKTTYKAKKPVQLPGAYNVNIKLDITSHNEDYTIVEQY |
| ERAEGRHSTGGMDELYKX |
| mCherry-mINT fusion DNA sequence |
| SEQ ID NO: 28 |
| ATGGTGAGCA AGGGCGAGGA GGATAACATG GCCATCATCA AGGAGTTCAT GCGCTTCAAG |
| GTGCACATGG AGGGCTCCGT GAACGGCCAC GAGTTCGAGA TCGAGGGCGA GGGCGAGGGC |
| CGCCCCTACG AGGGCACCCA GACCGCCAAG CTGAAGGTGA CCAAGGGTGG CCCCCTGCCC |
| TTCGCCTGGG ACATCCTGTC CCCTCAGTTC ATGTACGGCT CCAAGGCCTA CGTGAAGCAC |
| CCCGCCGACA TCCCCGACTA CTTGAAGCTG TCCTTCCCCG AGGGCTTCAA GTGGGAGCGC |
| GTGATGAACT TCGAGGACGG CGGCGTGGTG ACCGTGACCC AGGACTCCTC CCTGCAGGAC |
| GGCGAGTTCA TCTACAAGGT GAAGCTGCGC GGCACCAACT TCCCCTCCGA CGGCCCCGTA |
| ATGCAGAAGA AGACCATGGG CTGGGAGGCC TCCTCCGAGC GGATGTACCC CGAGGACGGC |
| GCCCTGAAGG GCGAGATCAA GCAGAGGCTG AAGCTGAAGG ACGGCGGCCA CTACGACGCT |
| GAGGTCAAGA CCACCTACAA GGCCAAGAAG CCCGTGCAGC TGCCCGGCGC CTACAACGTC |
| AACATCAAGT TGGACATCAC CTCCCACAAC GAGGACTACA CCATCGTGGA ACAGTACGAA |
| CGCGCCGAGG GCCGCCACTC CACCGGCGGC ATGGACGAGC TGTACAAGTA ATGC ACA CAA CAC |
| TGG CAG GAT GCT GTG CCT TGG ACA GAA CTC CTC AGT CTA CAG ACA GAG GAT GGC |
| TTC TGG AAA CTT ACA CCA GAA CTG GGA CTT ATA TTA AAT CTT AAT ACA AAT GGT |
| TTG CAC AGC TTT CTT AAA CAA AAA GGC ATT CAA TCT CTA GGT GTA AAA GGA AGA |
| GAA TGT CTC CTG GAC CTA ATT GCC ACA ATG CTG GTA CTA CAG TTT ATT CGC ACC |
| AGG TTG GAA AAA GAG GGA ATA GTG TTC AAA TCA CTG ATG AAA ATG GAT GAC CCT |
| TCT ATT TCC AGG AAT ATT CCC TGG GCT TTT GAG GCA ATA AAG CAA GCA AGT GAA |
| TGG GTA AGA AGA ACT GAA GGA CAG TAC CCA TCT ATC TGC CCA CGG CTT GAA CTG |
| GGG AAC GAC TGG GAC TCT GCC ACC AAG CAG TTG CTG GGA CTC CAG CCC ATA AGC |
| ACT GTG TCC CCT CTT CAT AGA GTC CTC CAT TAC AGT CAA GGC TAA |
| mCherry-mINT fusion amino acid sequence |
| SEQ ID NO: 29 |
| MVSKGEEDNMAIIKEFMRFKVHMEGSVNGHEFEIEGEGEGRPYEGTQTAKLKVTKGGPLPFAWDILSPQFMYG |
| SKAYVKHPADIPDYLKLSFPEGFKWERVMNFEDGGVVTVTQDSSLQDGEFIYKVKLRGTNFPSDGPVMQKKTM |

TABLE 1-continued

| Sequences |
|---|
| GWEASSERMYPEDGALKGEIKQRLKLKDGGHYDAEVKTTYKAKKPVQLPGAYNVNIKLDITSHNEDYTIVEQY<br>ERAEGRHSTGGMDELYKXCTQHWQDAVPWTELLSLQTEDGFWKLTPELGLILNLNTNGLHSFLKQKGIQSLGV<br>KGRECLLDLIATMLVLQFIRTRLEKEGIVFKSLMKMDDPSISRNIPWAFEAIKQASEWVRRTEGQYPSICPRL<br>ELGNDWDSATKQLLGLQPISTVSPLHRVLHYSQG |
| Full length protein VI (pVI) primer |
| SEQ ID NO: 30<br>CGGGATCCGCCTTCAGCTGGGGCTCGCTCTGGAGC |
| Full length protein VI (pVI) primer |
| SEQ ID NO: 31<br>CGGGAATTCTTACAGACCCACGATGCTGTTCAG |
| N-Term region of protein VI (NT) (aa 34-114) primer |
| SEQ ID NO: 32<br>CGGGATCCGCCTTCAGCTGGGGCTCGCTCTGGAGC |
| N-Term region of protein VI (NT) (aa 34-114) primer |
| SEQ ID NO: 33<br>CGGGAATTCTTACTCTCGGGAGGGCGGGGATC |
| TR primer |
| SEQ ID NO: 34<br>AAAGGATCCTATGGCAGCAAGGC |
| TR primer |
| SEQ ID NO: 35<br>AAAGAATTCTTACAGACCCACGATGCTGTT |
| pVI (aa 34-53) primer |
| SEQ ID NO: 36<br>CGGGATCCGCCTTCAGCTGGGGCTCGCTGTGGAGCGGCATTAAAAATTTCGGTTCCACCGTTAAGA<br>ACTATGAATTCCGG |
| pVI (aa 34-53) primer |
| SEQ ID NO: 37<br>CCGGAATTCATAGTTCTTAACGGTGGAACCGAAATTTTTAATGCCGCTCCACAGCGAGCCCCAGCT<br>GAAGGCGGATCCCG |
| INT domain (aa 1563-1724) primer |
| SEQ ID NO: 38<br>CGGGATTCGGCGGCGAATTCGATTTACGATATCCCAACGACCGAA |
| INT domain (aa 1563-1724) primer |
| SEQ ID NO: 39<br>CCCCTCGAGTTAGCCTTGACTGTAATGGAGGACTCTATG |
| pVI lytic peptide (aa 34-53) Forward primer |
| SEQ ID NO: 40<br>CTC TGC TAG CCA CCA TGG CCT TCA GCT GGG GCT CG |
| pVI lytic peptide (aa 34-53) Reverse primer |
| SEQ ID NO: 41<br>GGG GCC ATG GCG CTG CCG CGC GGC ACC AGG CCG TTC TTA ACG GTG GAA<br>CCG |
| mINT protein sequence (residues 1473-1724 of human<br>VPARP protein sequence) |

TABLE 1-continued

| Sequences |
|---|
| SEQ ID NO: 42 |
| Ala Asn Leu Arg Leu Pro Met Ala Ser Ala Leu Pro Glu Ala Leu Cys Ser Gln |
| Ser Arg Thr Thr Pro Val Asp Leu Cys Leu Leu Glu Glu Ser Val Gly Ser Leu |
| Glu Gly Ser Arg Cys Pro Val Phe Ala Phe Gln Ser Ser Asp Thr Glu Ser Asp |
| Glu Leu Ser Glu Val Leu Gln Asp Ser Cys Phe Leu Gln Ile Lys Cys Asp Thr |
| Lys Asp Asp Ser Ile Pro Cys Phe Leu Glu Leu Lys Glu Glu Asp Glu Ile Val |
| Cys Thr Gln His Trp Gln Asp Ala Val Pro Trp Thr Glu Leu Leu Ser Leu Gln |
| Thr Glu Asp Gly Phe Trp Lys Leu Thr Pro Glu Leu Gly Leu Ile Leu Asn Leu |
| Asn Thr Asn Gly Leu His Ser Phe Leu Lys Gln Lys Gly Ile Gln Ser Leu Gly |
| Val Lys Gly Arg Glu Cys Leu Leu Asp Leu Ile Ala Thr Met Leu Val Leu Gln |
| Phe Ile Arg Thr Arg Leu Glu Lys Glu Gly Ile Val Phe Lys Ser Leu Met Lys |
| Met Asp Asp Pro Ser Ile Ser Arg Asn Ile Pro Trp Ala Phe Glu Ala Ile Lys |
| Gln Ala Ser Glu Trp Val Arg Arg Thr Glu Gly Gln Tyr Pro Ser Ile Cys Pro |
| Arg Leu Glu Leu Gly Asn Asp Trp Asp Ser Ala Thr Lys Gln Leu Leu Gly Leu |
| Gln Pro Ile Ser Thr Val Ser Pro Leu His Arg Val Leu His Tyr Ser Gln Gly |

REFERENCES CITED

1. Kedersha N L, Rome L H: *Isolation and characterization of a novel ribonucleoprotein particle: large structures contain a single species of small RNA. J Cell Biol* 1986, 103(3):699-709.

2. Kong L B, Siva A C, Rome L H, Stewart P L: *Structure of the vault, a ubiquitous celular component. Structure* 1999, 7(4):371-379.

3. Kedersha N L, Heuser J E, Chugani D C, Rome L H: Vaults. III. *Vault ribonucleoprotein particles open into flower-like structures with octagonal symmetry. J Cell Biol* 1991, 112(2):225-235.

4. Suprenant K A: *Vault ribonucleoprotein particles: sarcophagi, gondolas, or safety deposit boxes? Biochemistry* 2002, 41(49):14447-14454.

5. Berger W, Steiner E, Grusch M, Elbling L, Micksche M: *Vaults and the major vault protein: novel roles in signal pathway regulation and immunity. Cell Mol Life Sci* 2009, 66(1):43-61.

6. Champion C I, Kickhoefer V A, Liu G, Moniz R J, Freed A S, Bergmann L L, Vaccari D, Raval-Fernandes S, Chan A M, Rome L H et al: *A vault nanoparticle vaccine induces protective mucosal immunity. PLoS One* 2009, 4(4):e5409. Epub April 2009 5430.

7. Stephen A G, Raval-Fernandes S, Huynh T, Torres M, Kickhoefer V A, Rome L H: *Assembly of vault-like particles in insect cells expressing only the major vault protein. J Biol Chem* 2001, 276(26):23217-23220. Epub 22001 May 23210.

8. Kickhoefer V A, Garcia Y, Mikyas Y, Johansson E, Zhou J C, Raval-Fernandes S, Minoofar P, Zink J I, Dunn B, Stewart P L et al: *Engineering of vault nanocapsules with enzymatic and fluorescent properties. Proc Natl Acad Sci USA* 2005, 102(12):4348-4352. Epub March 2005 4347.

9. Kickhoefer, V. A., et al. (2005). Engineering of vault nanocapsules with enzymatic and fluorescent properties. *Proc. Natl. Acad. Sci. U.S.A.* 102: 4328-4352.

10. Poderycki, M. J., et al. (2006). The vault exterior shell is a dynamic structure that allows incorporation of vault-associated proteins into its interior. *Biochemistry* (*Mosc*).45: 12184-12193.

11. Goldsmith, L. E., Yu, M., Rome, L. H., and Monbouquette, H. G. (2007). Vault nanocapsule dissociation into halves triggered at low pH. *Biochemistry* (*Mose*). 46:2865-2875.

12. Kaddis, C. S., et al. (2007). Sizing large proteins and protein complexes by electrospray ionization mass spectrometry and ion mobility. *J. Am. Soe. Mass. Speetmm.* 18: 1206-1216.

13. Stephen, A G., Raval-Fernandes, S., Huynh, T., Torres, M., Kickhoefer, V. A, and Rome, L. H. (2001). Assembly of vault-like particles in insect cells expressing only the major vault protein. J. *Biol. Chem.* 276: 23217-23220.

14. Blumenthal, R., Seth, P., Willingham, M. C., and Pastan, I. (1986). PH-dependent lysis of liposomes by adenovirus biochemistry. *Biochemistry* (*Mose*). 25: 2231-2237.

15. Haidar, M. A (1976). Tobacco rattle virus RNA-protein interactions. *Philosophical transactions of the Royal Society of London* 276: 165-172.

16. Goodman, R. M., McDonald, J. G., Home, R. W., and Bancroft, J. B. (1976). Assembly of flexuous plant viruses and their proteins. *Philosophical transactions of the Royal Society of London* 276: 173-179.

17. Hed, J., Hallden, G., Johansson, S. G., and Larsson, P. (1987). The use of fluorescence quencing in flow cytofluorometry to measure the attachment and ingestion phases in phagocytosis in peripheral blood without prior cell separation. *J. Immunol. Methods* 101: 119-125.

18. Wiethoff. C. M., Wodrich, H., Gerace. L., and Nemerow, G. R. (2005). Adenovirus protein VI mediates membrane disruption following capsid disassembly. *J. Viral.* 79: 1992-2000.

19. Barbiei, L., Battelli, M. G., and Stirpe, F. (1993). Ribosome-inactivating proteins from plants. *Biochima et Biophysica Acta* 1154: 237-282.

20. Weyergang, A, Selbo, P. K., and Berg, K. (2006). Photochemically stimulated drug delivery increases the cytotoxicity and specificity of EGF-saporin. *J. Controlled Release* 111: 165-173.

21. Yip, W. L., Weyergang, A, Berg, K., Tennesen, H. H" and Selbo, P. K. (2007). Targeted delivery and enhanced cytotoxicity of cetuximab-saporin by photochemical internalization in EGFR-positive cancer cells. *Mol. Pharmacol.* 4: 241-251.

22. Walters, R., and Welsh, M. (1999). Mechanism by which calcium phosphate coprecipitation enhances adenovirus-mediated gene transfer. *Gene Ther.* 6: 1845-1850.

23. Lee, J. H., Zabner, J., and Welsh, M. J. (1999). Delivery of an adenovirus vector in a calcium phosphate coprecipitate enhances the therapeutic index of gene transfer to airway epithelia. *Hum. Gene Ther.* 10: 603-613.

24. Toyoda, K., Andresen, J. J., Zabner, J., Faraci, F. M., and Heistad, D. D. (2007) Calcium phosphate precipitates augment adenovirus-mediated gene transfer to blood vessels in vitro and in vivo. *Gene Ther.* 10: 603-613.

25. Seiler, M. P., et al. (2007). Dendritic cell function after gene transfer with adenovirus-calcium phosphate co-precipitates. Mol. Ther. 15: 386-392.

26. Mikyas, Y.; Makabi, M.; Raval-Fernandes, S.; Harrington, L.; Kickhoefer, V. A.; Rome, L. H.; Stewart, P. L., Cryoelectron microscopy imaging of recombinant and tissue derived vaults: localization of the MVP N termini and VPARP. *J Mol Biol* 2004, 344, (1), 91-105.

27. Champion, C. I.; Kickhoefer, V. A.; Liu, G.; Moniz, R. J.; Freed, A. S.; Bergmann, L. L.; Vaccari, D.; Raval-Fernandes, S.; Chan, A. M.; Rome, L. H.; Kelly, K. A., A vault nanoparticle vaccine induces protective mucosal immunity. *PLoS One* 2009, 4, (4), e5409.

28. Esfandiary, R.; Kickhoefer, V. A.; Rome, L. H.; Joshi, S. B.; Middaugh, C. R., Structural stability of vault particles. *J Pharm Sci* 2009, 98, (4), 1376-86.

29. Kickhoefer, V. A.; Han, M.; Raval-Fernandes, S.; Poderycki, M. J.; Moniz, R. J.; Vaccari, D.; Silvestry, M.; Stewart, P. L.; Kelly, K. A.; Rome, L. H., Targeting vault nanoparticles to specific cell surface receptors. *ACS Nano* 2009, 3, (1), 27-36.

30. Goldsmith, L. E.; Yu, M.; Rome, L. H.; Monbouquette, H. G., Vault nanocapsule dissociation into halves triggered at low pH. *Biochemistry* 2007, 46, (10), 2865-75.

31. Stephen, A. G.; Raval-Fernandes, S.; Huynh, T.; Torres, M.; Kickhoefer, V. A.; Rome, L. H., Assembly of vault-like particles in insect cells expressing only the major vault protein. *J Biol Chem* 2001, 276, (26), 23217-20.

32. Lai, C. Y.; Wiethoff, C. M.; Kickhoefer, V. A.; Rome, L. H.; Nemerow, G. R., Vault nanoparticles containing an adenovirus-derived membrane lytic protein facilitate toxin and gene transfer. *ACS Nano* 2009, 3, (3), 691-9.

33. Wiethoff, C. M.; Wodrich, H.; Gerace, L.; Nemerow, G. R., Adenovirus protein VI mediates membrane disruption following capsid disassembly. *J Virol* 2005, 79, (4), 1992-2000.

34. Shaughnessy, L. M.; Hoppe, A. D.; Christensen, K. A.; Swanson, J. A., Membrane perforations inhibit lysosome fusion by altering pH and calcium in *Listeria monocytogenes* vacuoles. *Cell Microbiol* 2006, 8, (5), 781-92.

35. Kingdon, G. C.; Sword, C. P., Effects of *Listeria monocytogenes* Hemolysin on Phagocytic Cells and Lysosomes. *Infect Immun* 1970, 1, (4), 356-62.

36. Xie, H.; Pallero, M. A.; Gupta, K.; Chang, P.; Ware, M. F.; Witke, W.; Kwiatkowski, D. J.; Lauffenburger, D. A.; Murphy-Ullrich, J. E.; Wells, A., EGF receptor regulation of cell motility: EGF induces disassembly of focal adhesions independently of the motility-associated PLCgamma signaling pathway. *J Cell Sci* 1998, 111 (Pt 5), 615-24.

37. Wells, A., EGF receptor. *Int J Biochem Cell Biol* 1999, 31, (6), 637-43

---

The invention claimed is:

1. A vault-like particle comprising a membrane lytic domain comprising the amino acid sequence of SEQ ID NO:3, a major vault protein comprising the amino acid sequence of SEQ ID NO:16, and an antibody binding Z domain.

2. The vault-like particle of claim 1, wherein the membrane lytic domain is fused to the C-terminus of the major vault protein, and the antibody binding Z domain is fused to the N-terminus of the major vault protein, forming a fusion protein.

3. The vault-like particle of claim 1, wherein said fusion protein comprises the amino acid sequence of SEQ ID NO:11.

* * * * *

SEQUENCE LISTING

```
<160> NUMBER OF SEQ ID NOS: 55

<210> SEQ ID NO 1
<211> LENGTH: 250
<212> TYPE: PRT
<213> ORGANISM: Human adenovirus 5

<400> SEQUENCE: 1

Met Glu Asp Ile Asn Phe Ala Ser Leu Ala Pro Arg His Gly Ser Arg
1               5                   10                  15

Pro Phe Met Gly Asn Trp Gln Asp Ile Gly Thr Ser Asn Met Ser Gly
            20                  25                  30

Gly Ala Phe Ser Trp Gly Ser Leu Trp Ser Gly Ile Lys Asn Phe Gly
        35                  40                  45

Ser Thr Val Lys Asn Tyr Gly Ser Lys Ala Trp Asn Ser Ser Thr Gly
    50                  55                  60

Gln Met Leu Arg Asp Lys Leu Lys Glu Gln Asn Phe Gln Gln Lys Val
65                  70                  75                  80

Val Asp Gly Leu Ala Ser Gly Ile Ser Gly Val Val Asp Leu Ala Asn
                85                  90                  95

Gln Ala Val Gln Asn Lys Ile Asn Ser Lys Leu Asp Pro Arg Pro Pro
            100                 105                 110

Val Glu Glu Pro Pro Pro Ala Val Glu Thr Val Ser Pro Glu Gly Arg
        115                 120                 125
```

```
Gly Glu Lys Arg Pro Arg Pro Asp Arg Glu Glu Thr Leu Val Thr Gln
    130                 135                 140

Ile Asp Glu Pro Pro Ser Tyr Glu Glu Ala Leu Lys Gln Gly Leu Pro
145                 150                 155                 160

Thr Thr Arg Pro Ile Ala Pro Met Ala Thr Gly Val Leu Gly Gln His
                165                 170                 175

Thr Pro Val Thr Leu Asp Leu Pro Pro Pro Ala Asp Thr Gln Gln Lys
            180                 185                 190

Pro Val Leu Pro Gly Pro Thr Ala Val Val Val Thr Arg Pro Ser Arg
        195                 200                 205

Ala Ser Leu Arg Arg Ala Ala Ser Gly Pro Arg Ser Leu Arg Pro Val
    210                 215                 220

Ala Ser Gly Asn Trp Gln Ser Thr Leu Asn Ser Ile Val Gly Leu Gly
225                 230                 235                 240

Val Gln Ser Leu Lys Arg Arg Arg Cys Phe
                245                 250


<210> SEQ ID NO 2
<211> LENGTH: 60
<212> TYPE: DNA
<213> ORGANISM: Human adenovirus 5

<400> SEQUENCE: 2

gccttcagct ggggctcgct gtggagcggc attaaaaatt tcggttccac cgttaagaac     60


<210> SEQ ID NO 3
<211> LENGTH: 20
<212> TYPE: PRT
<213> ORGANISM: Human adenovirus 5

<400> SEQUENCE: 3

Ala Phe Ser Trp Gly Ser Leu Trp Ser Gly Ile Lys Asn Phe Gly Ser
1               5                   10                  15

Thr Val Lys Asn
            20


<210> SEQ ID NO 4
<211> LENGTH: 81
<212> TYPE: PRT
<213> ORGANISM: Human adenovirus 5

<400> SEQUENCE: 4

Ala Phe Ser Trp Gly Ser Leu Trp Ser Gly Ile Lys Asn Phe Gly Ser
1               5                   10                  15

Thr Val Lys Asn Tyr Gly Ser Lys Ala Trp Asn Ser Ser Thr Gly Gln
            20                  25                  30

Met Leu Arg Asp Lys Leu Lys Glu Gln Asn Phe Gln Gln Lys Val Val
        35                  40                  45

Asp Gly Leu Ala Ser Gly Ile Ser Gly Val Val Asp Leu Ala Asn Gln
    50                  55                  60

Ala Val Gln Asn Lys Ile Asn Ser Lys Leu Asp Pro Arg Pro Pro Val
65                  70                  75                  80

Glu


<210> SEQ ID NO 5
<211> LENGTH: 489
<212> TYPE: DNA
<213> ORGANISM: Homo sapiens
```

<400> SEQUENCE: 5

```
tgcacacaac actggcagga tgctgtgcct tggacagaac tcctcagtct acagacagag     60
gatggcttct ggaaacttac accagaactg ggacttatat taaatcttaa tacaaatggt    120
ttgcacagct ttcttaaaca aaaaggcatt caatctctag gtgtaaaagg aagagaatgt    180
ctcctggacc taattgccac aatgctggta ctacagttta ttcgcaccag gttggaaaaa    240
gagggaatag tgttcaaatc actgatgaaa atggatgacc cttctatttc caggaatatt    300
ccctgggctt ttgaggcaat aaagcaagca agtgaatggg taagaagaac tgaaggacag    360
tacccatcta tctgcccacg gcttgaactg ggaacgact gggactctgc caccaagcag     420
ttgctgggac tccagcccat aagcactgtg tcccctcttc atagagtcct ccattacagt    480
caaggctaa                                                            489
```

<210> SEQ ID NO 6
<211> LENGTH: 162
<212> TYPE: PRT
<213> ORGANISM: Homo sapiens

<400> SEQUENCE: 6

```
Cys Thr Gln His Trp Gln Asp Ala Val Pro Trp Thr Glu Leu Leu Ser
1               5                   10                  15

Leu Gln Thr Glu Asp Gly Phe Trp Lys Leu Thr Pro Glu Leu Gly Leu
            20                  25                  30

Ile Leu Asn Leu Asn Thr Asn Gly Leu His Ser Phe Leu Lys Gln Lys
        35                  40                  45

Gly Ile Gln Ser Leu Gly Val Lys Gly Arg Glu Cys Leu Leu Asp Leu
    50                  55                  60

Ile Ala Thr Met Leu Val Leu Gln Phe Ile Arg Thr Arg Leu Glu Lys
65                  70                  75                  80

Glu Gly Ile Val Phe Lys Ser Leu Met Lys Met Asp Asp Pro Ser Ile
                85                  90                  95

Ser Arg Asn Ile Pro Trp Ala Phe Glu Ala Ile Lys Gln Ala Ser Glu
            100                 105                 110

Trp Val Arg Arg Thr Glu Gly Gln Tyr Pro Ser Ile Cys Pro Arg Leu
        115                 120                 125

Glu Leu Gly Asn Asp Trp Asp Ser Ala Thr Lys Gln Leu Leu Gly Leu
    130                 135                 140

Gln Pro Ile Ser Thr Val Ser Pro Leu His Arg Val Leu His Tyr Ser
145                 150                 155                 160

Gln Gly
```

<210> SEQ ID NO 7

<400> SEQUENCE: 7

000

<210> SEQ ID NO 8
<211> LENGTH: 2861
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (3)..(5)
<223> OTHER INFORMATION: a, c, t, g, unknown or other
<220> FEATURE:

<221> NAME/KEY: modified_base
<222> LOCATION: (7)..(7)
<223> OTHER INFORMATION: a, c, t, g, unknown or other

<400> SEQUENCE: 8

```
aannngnatt ttactgtttt cgtacagttt tgtaataaaa aaacctataa atattccgga     60
ttattcatac cgtcccacca tcgggcgcgg atcccggtcc gaagcgcgcg gaattcgcgg    120
ccgcgtcgac tgtggcttgc agctgccagc taccctgcta aatgtttggt gggaaaagct    180
tggggattcac catggccttc agctggggct cgctgtggag cggcattaaa aatttcggtt    240
ccaccgttaa gaacggcctg gtgccgcgcg gcagcgccat ggcaactgaa gaggccatca    300
tccgcatccc cccataccac tacatccatg tgctggacca gaacagtaat gtgtcccgtg    360
tggaggttgg accaaagacc tacatccggc aggacaatga gagggtactg tttgccccag    420
ttcgcatggt gaccgtcccc ccacgccact actgcatagt ggccaaccct gtgtcccggg    480
acacccagag ttctgtgtta tttgacatca caggacaagt ccgactccgg cacgctgacc    540
aggagatccg actagcccag gacccccttcc ccctgtatcc aggggaggtg ctggaaaagg    600
acatcacccc actgcaggtg gttctgccca acacagcact gcatcttaag gcgttgctgg    660
actttgagga taagaatgga gacaaggtca tggcaggaga cgagtggcta tttgagggac    720
ctggcaccta catcccacag aaggaagtgg aagtcgtgga gatcattcag gccacagtca    780
tcaaacagaa ccaagcactg cggctaaggg cccgaaagga gtgctttgac cgggagggca    840
aggggcgcgt gacaggtgag gagtggctgg tccgatccgt gggggcttac ctcccagctg    900
tctttgaaga ggtgctggat ctggtggatg ctgtgatcct tacagaaaag actgccctgc    960
acctccgggc tctgcagaac ttcagggacc ttcggggagt gctccaccgc accggggagg   1020
aatggttagt gacagtgcag gacacagaag cccatgttcc agatgtctat gaggaggtgc   1080
ttggggtagt acccatcacc accctgggac ctcgacacta ctgtgtcatt cttgacccaa   1140
tgggaccaga cggcaagaac cagctgggac aaaagcgtgt tgtcaaggga gagaagtcct   1200
ttttcctcca gccaggagag aggctggagc gaggcatcca ggatgtgtat gtgctgtcag   1260
agcagcaggg gctgctactg aaggcactgc agcccctgga ggagggagag agcgaggaga   1320
aggtctccca tcaggccgga gactgctggc tcatccgtgg gcccctggag tatgtgccat   1380
ctgcaaaagt ggaggtggtg gaggagcgtc aggctatccc tctggaccaa aatgagggca   1440
tctatgtgca ggatgtcaag acggggaagg tgcgggctgt gattggaagc acctacatgc   1500
tgactcagga tgaagtcctg tgggaaaagg agctgccttc tggggtggag gagctgctga   1560
acttggggca tgaccctctg gcagacaggg gtcagaaggg cacagccaag ccccttcagc   1620
cctcagctcc aaggaacaag acccgagtgg tcagctaccg tgtcccgcac aatgcagcgg   1680
tgcaggtcta tgactacaga gccaagagag cccgtgtggt ctttgggccc gagctagtga   1740
cactggatcc tgaggagcag ttcacagtat tgtccctttc tgccgggcga cccaagcgtc   1800
ctcatgcccg ccgtgcactc tgcctactgc tgggacctga tttctttact gatgtcatca   1860
ccatcgaaac tgcagatcat gccaggttgc agctgcagct tgcctacaac tggcactttg   1920
aactgaagaa ccggaatgac cctgcagagg cagccaagct tttctccgtg cctgacttcg   1980
tgggtgacgc ctgcaaggcc attgcatccc gagtccgggg ggctgtagcc tctgtcacct   2040
ttgatgactt ccataaaaac tcagcccgga tcattcgaat ggctgttttt ggctttgaga   2100
tgtctgaaga cacaggtcct gatggcacac tcctgcccaa ggctcgagac caggcagtct   2160
ttccccaaaa cgggctggta gtcagcagtg tggatgtgca gtcagtggag cccgtggacc   2220
```

```
agaggacccg ggatgccctt cagcgcagcg ttcagctggc catcgaaatt accaccaact   2280

cccaggaggc agcagccaag cacgaggctc agagactgga acaggaagcc cgtggtcggc   2340

ttgagaggca gaagatcttg gaccagtcag aagctgaaaa agcccgcaag gaactcttgg   2400

agcttgaggc tatgagcatg gctgtggaga gcacgggtaa tgccaaagca gaggctgagt   2460

cccgtgcaga ggcagcgagg atcgaaggag aaggctctgt gctgcaggcc aagctcaagg   2520

cacaggcgct agccattgag acggaggctg agttggagcg agtaaagaaa gtacgagaga   2580

tggaactgat ctatgcccgg gcccagttgg agctggaggt gagcaaggcg cagcagcttg   2640

ccaatgtgga ggcaaagaag ttcaaggaga tgacagaggc actgggcccc ggcaccatca   2700

gggacctggc tgtggccggg ccagagatgc aggtgaaact tctccagtcc ctgggcctga   2760

aatccactct catcaccgat ggctcgtctc ccatcaacct cttcagcaca gccttcgggt   2820

tgctggggct ggggtctgat ggtcagccgc cagcacagaa g                       2861
```

```
<210> SEQ ID NO 9
<211> LENGTH: 890
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Ala Phe Ser Trp Gly Ser Leu Trp Ser Gly Ile Lys Asn Phe Gly
1               5                   10                  15

Ser Thr Val Lys Asn Gly Leu Val Pro Arg Gly Ser Ala Met Ala Thr
            20                  25                  30

Glu Glu Ala Ile Ile Arg Ile Pro Pro Tyr His Tyr Ile His Val Leu
        35                  40                  45

Asp Gln Asn Ser Asn Val Ser Arg Val Glu Val Gly Pro Lys Thr Tyr
    50                  55                  60

Ile Arg Gln Asp Asn Glu Arg Val Leu Phe Ala Pro Val Arg Met Val
65                  70                  75                  80

Thr Val Pro Pro Arg His Tyr Cys Ile Val Ala Asn Pro Val Ser Arg
                85                  90                  95

Asp Thr Gln Ser Ser Val Leu Phe Asp Ile Thr Gly Gln Val Arg Leu
            100                 105                 110

Arg His Ala Asp Gln Glu Ile Arg Leu Ala Gln Asp Pro Phe Pro Leu
        115                 120                 125

Tyr Pro Gly Glu Val Leu Glu Lys Asp Ile Thr Pro Leu Gln Val Val
    130                 135                 140

Leu Pro Asn Thr Ala Leu His Leu Lys Ala Leu Leu Asp Phe Glu Asp
145                 150                 155                 160

Lys Asn Gly Asp Lys Val Met Ala Gly Asp Glu Trp Leu Phe Glu Gly
                165                 170                 175

Pro Gly Thr Tyr Ile Pro Gln Lys Glu Val Glu Val Val Glu Ile Ile
            180                 185                 190

Gln Ala Thr Val Ile Lys Gln Asn Gln Ala Leu Arg Leu Arg Ala Arg
        195                 200                 205

Lys Glu Cys Phe Asp Arg Glu Gly Lys Gly Arg Val Thr Gly Glu Glu
    210                 215                 220

Trp Leu Val Arg Ser Val Gly Ala Tyr Leu Pro Ala Val Phe Glu Glu
225                 230                 235                 240

Val Leu Asp Leu Val Asp Ala Val Ile Leu Thr Glu Lys Thr Ala Leu
                245                 250                 255
```

```
His Leu Arg Ala Leu Gln Asn Phe Arg Asp Leu Arg Gly Val Leu His
            260                 265                 270

Arg Thr Gly Glu Glu Trp Leu Val Thr Val Gln Asp Thr Glu Ala His
        275                 280                 285

Val Pro Asp Val Tyr Glu Glu Val Leu Gly Val Val Pro Ile Thr Thr
    290                 295                 300

Leu Gly Pro Arg His Tyr Cys Val Ile Leu Asp Pro Met Gly Pro Asp
305                 310                 315                 320

Gly Lys Asn Gln Leu Gly Gln Lys Arg Val Val Lys Gly Glu Lys Ser
                325                 330                 335

Phe Phe Leu Gln Pro Gly Glu Arg Leu Glu Arg Gly Ile Gln Asp Val
            340                 345                 350

Tyr Val Leu Ser Glu Gln Gln Gly Leu Leu Leu Lys Ala Leu Gln Pro
        355                 360                 365

Leu Glu Glu Gly Glu Ser Glu Glu Lys Val Ser His Gln Ala Gly Asp
    370                 375                 380

Cys Trp Leu Ile Arg Gly Pro Leu Glu Tyr Val Pro Ser Ala Lys Val
385                 390                 395                 400

Glu Val Val Glu Glu Arg Gln Ala Ile Pro Leu Asp Gln Asn Glu Gly
                405                 410                 415

Ile Tyr Val Gln Asp Val Lys Thr Gly Lys Val Arg Ala Val Ile Gly
            420                 425                 430

Ser Thr Tyr Met Leu Thr Gln Asp Glu Val Leu Trp Glu Lys Glu Leu
        435                 440                 445

Pro Ser Gly Val Glu Glu Leu Leu Asn Leu Gly His Asp Pro Leu Ala
    450                 455                 460

Asp Arg Gly Gln Lys Gly Thr Ala Lys Pro Leu Gln Pro Ser Ala Pro
465                 470                 475                 480

Arg Asn Lys Thr Arg Val Val Ser Tyr Arg Val Pro His Asn Ala Ala
                485                 490                 495

Val Gln Val Tyr Asp Tyr Arg Ala Lys Arg Ala Arg Val Val Phe Gly
            500                 505                 510

Pro Glu Leu Val Thr Leu Asp Pro Glu Glu Gln Phe Thr Val Leu Ser
        515                 520                 525

Leu Ser Ala Gly Arg Pro Lys Arg Pro His Ala Arg Arg Ala Leu Cys
    530                 535                 540

Leu Leu Leu Gly Pro Asp Phe Phe Thr Asp Val Ile Thr Ile Glu Thr
545                 550                 555                 560

Ala Asp His Ala Arg Leu Gln Leu Gln Leu Ala Tyr Asn Trp His Phe
                565                 570                 575

Glu Leu Lys Asn Arg Asn Asp Pro Ala Glu Ala Ala Lys Leu Phe Ser
            580                 585                 590

Val Pro Asp Phe Val Gly Asp Ala Cys Lys Ala Ile Ala Ser Arg Val
        595                 600                 605

Arg Gly Ala Val Ala Ser Val Thr Phe Asp Asp Phe His Lys Asn Ser
    610                 615                 620

Ala Arg Ile Ile Arg Met Ala Val Phe Gly Phe Glu Met Ser Glu Asp
625                 630                 635                 640

Thr Gly Pro Asp Gly Thr Leu Leu Pro Lys Ala Arg Asp Gln Ala Val
                645                 650                 655

Phe Pro Gln Asn Gly Leu Val Val Ser Ser Val Asp Val Gln Ser Val
            660                 665                 670

Glu Pro Val Asp Gln Arg Thr Arg Asp Ala Leu Gln Arg Ser Val Gln
```

```
        675                 680                 685

Leu Ala Ile Glu Ile Thr Thr Asn Ser Gln Glu Ala Ala Lys His
    690                 695                 700

Glu Ala Gln Arg Leu Glu Gln Glu Ala Arg Gly Arg Leu Glu Arg Gln
705                 710                 715                 720

Lys Ile Leu Asp Gln Ser Glu Ala Glu Lys Ala Arg Lys Glu Leu Leu
                725                 730                 735

Glu Leu Glu Ala Met Ser Met Ala Val Glu Ser Thr Gly Asn Ala Lys
            740                 745                 750

Ala Glu Ala Glu Ser Arg Ala Glu Ala Ala Arg Ile Glu Gly Glu Gly
        755                 760                 765

Ser Val Leu Gln Ala Lys Leu Lys Ala Gln Ala Leu Ala Ile Glu Thr
    770                 775                 780

Glu Ala Glu Leu Glu Arg Val Lys Lys Val Arg Glu Met Glu Leu Ile
785                 790                 795                 800

Tyr Ala Arg Ala Gln Leu Glu Leu Glu Val Ser Lys Ala Gln Gln Leu
                805                 810                 815

Ala Asn Val Glu Ala Lys Lys Phe Lys Glu Met Thr Glu Ala Leu Gly
            820                 825                 830

Pro Gly Thr Ile Arg Asp Leu Ala Val Ala Gly Pro Glu Met Gln Val
        835                 840                 845

Lys Leu Leu Gln Ser Leu Gly Leu Lys Ser Thr Leu Ile Thr Asp Gly
    850                 855                 860

Ser Ser Pro Ile Asn Leu Phe Ser Thr Ala Phe Gly Leu Leu Gly Leu
865                 870                 875                 880

Gly Ser Asp Gly Gln Pro Pro Ala Gln Lys
                885                 890
```

<210> SEQ ID NO 10
<211> LENGTH: 2973
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (3)..(5)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other

<400> SEQUENCE: 10

```
aannngnatt ttactgtttt cgtacagttt tgtaataaaa aaacctataa atattccgga      60

ttattcatac cgtcccacca tcgggcgcgg atcccggtcc gaagcgcgcg gaattcgcgg     120

ccgcgtcgac tgtggcttgc agctgccagc taccctgcta aatgtttggt gggaaaagct     180

tgggattcac catggccttc agctggggct cgctgtggag cggcattaaa aatttcggtt     240

ccaccgttaa gaacggcctg gtgccgcgcg gcagcgccat ggcaactgaa gaggccatca     300

tccgcatccc cccataccac tacatccatg tgctggacca gaacagtaat gtgtcccgtg     360

tggaggttgg accaaagacc tacatccggc aggacaatga gagggtactg tttgccccag     420

ttcgcatggt gaccgtcccc ccacgccact actgcatagt ggccaaccct gtgtcccggg     480

acacccagag ttctgtgtta tttgacatca caggacaagt ccgactccgg cacgctgacc     540

aggagatccg actagcccag gaccccttcc ccctgtatcc aggggaggtg ctggaaaagg     600
```

-continued

```
acatcacccc actgcaggtg gttctgccca acacagcact gcatcttaag gcgttgctgg    660
actttgagga taagaatgga gacaaggtca tggcaggaga cgagtggcta tttgagggac    720
ctggcaccta catcccacag aaggaagtgg aagtcgtgga gatcattcag gccacagtca    780
tcaaacagaa ccaagcactg cggctaaggg cccgaaagga gtgctttgac cgggagggca    840
aggggcgcgt gacaggtgag gagtggctgg tccgatccgt gggggcttac ctcccagctg    900
tctttgaaga ggtgctggat ctggtggatg ctgtgatcct tacagaaaag actgccctgc    960
acctccgggc tctgcagaac ttcagggacc ttcggggagt gctccaccgc accggggagg   1020
aatggttagt gacagtgcag gacacagaag cccatgttcc agatgtctat gaggaggtgc   1080
ttggggtagt acccatcacc accctgggac ctcgacacta ctgtgtcatt cttgacccaa   1140
tgggaccaga cggcaagaac cagctgggac aaaagcgtgt tgtcaaggga gagaagtcct   1200
ttttcctcca gccaggagag aggctggagc gaggcatcca ggatgtgtat gtgctgtcag   1260
agcagcaggg gctgctactg aaggcactgc agcccctgga ggagggagag agcgaggaga   1320
aggtctccca tcaggccgga gactgctggc tcatccgtgg gcccctggag tatgtgccat   1380
ctgcaaaagt ggaggtggtg gaggagcgtc aggctatccc tctggaccaa aatgagggca   1440
tctatgtgca ggatgtcaag acggggaagg tgcgggctgt gattggaagc acctacatgc   1500
tgactcagga tgaagtcctg tgggaaaagg agctgccttc tggggtggag gagctgctga   1560
acttggggca tgaccctctg gcagacaggg gtcagaaggg cacagccaag ccccttcagc   1620
cctcagctcc aaggaacaag acccgagtgg tcagctaccg tgtcccgcac aatgcagcgg   1680
tgcaggtcta tgactacaga gccaagagag cccgtgtggt ctttgggccc gagctagtga   1740
cactggatcc tgaggagcag ttcacagtat tgtccctttc tgccgggcga cccaagcgtc   1800
ctcatgcccg ccgtgcactc tgcctactgc tgggacctga tttctttact gatgtcatca   1860
ccatcgaaac tgcagatcat gccaggttgc agctgcagct tgcctacaac tggcactttg   1920
aactgaagaa ccggaatgac cctgcagagg cagccaagct tttctccgtg cctgacttcg   1980
tgggtgacgc ctgcaaggcc attgcatccc gagtccgggg ggctgtagcc tctgtcacct   2040
ttgatgactt ccataaaaac tcagcccgga tcattcgaat ggctgttttt ggctttgaga   2100
tgtctgaaga cacaggtcct gatggcacac tcctgcccaa ggctcgagac caggcagtct   2160
ttccccaaaa cgggctggta gtcagcagtg tggatgtgca gtcagtggag cccgtggacc   2220
agaggacccg ggatgccctt cagcgcagcg ttcagctggc catcgaaatt accaccaact   2280
cccaggaggc agcagccaag cacgaggctc agagactgga acaggaagcc cgtggtcggc   2340
ttgagaggca gaagatcttg gaccagtcag aagctgaaaa agcccgcaag gaactcttgg   2400
agcttgaggc tatgagcatg gctgtggaga gcacgggtaa tgccaaagca gaggctgagt   2460
cccgtgcaga ggcagcgagg atcgaaggag aaggctctgt gctgcaggcc aagctcaagg   2520
cacaggcgct agccattgag acggaggctg agttggagcg agtaaagaaa gtacgagaga   2580
tggaactgat ctatgcccgg gcccagttgg agctggaggt gagcaaggcg cagcagcttg   2640
ccaatgtgga ggcaaagaag ttcaaggaga tgacagaggc actgggcccc ggcaccatca   2700
gggacctggc tgtggccggg ccagagatgc aggtgaaact tctccagtcc ctgggcctga   2760
aatccactct catcaccgat ggctcgtctc ccatcaacct cttcagcaca gccttcgggt   2820
tgctggggct ggggtctgat ggtcagccgc cagcacagaa gtttaacatg cagcagcagc   2880
gccgctttta cgaggccctg cacgacccca acctgaacga ggagcagcgc aacgccaaga   2940
ttaagagcat tcgcgacgac tagggtacct cag                                 2973
```

<210> SEQ ID NO 11
<211> LENGTH: 923
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 11

```
Met Ala Phe Ser Trp Gly Ser Leu Trp Ser Gly Ile Lys Asn Phe Gly
1               5                   10                  15

Ser Thr Val Lys Asn Gly Leu Val Pro Arg Gly Ser Ala Met Ala Thr
            20                  25                  30

Glu Glu Ala Ile Ile Arg Ile Pro Pro Tyr His Tyr Ile His Val Leu
        35                  40                  45

Asp Gln Asn Ser Asn Val Ser Arg Val Glu Val Gly Pro Lys Thr Tyr
    50                  55                  60

Ile Arg Gln Asp Asn Glu Arg Val Leu Phe Ala Pro Val Arg Met Val
65                  70                  75                  80

Thr Val Pro Pro Arg His Tyr Cys Ile Val Ala Asn Pro Val Ser Arg
                85                  90                  95

Asp Thr Gln Ser Ser Val Leu Phe Asp Ile Thr Gly Gln Val Arg Leu
            100                 105                 110

Arg His Ala Asp Gln Glu Ile Arg Leu Ala Gln Asp Pro Phe Pro Leu
        115                 120                 125

Tyr Pro Gly Glu Val Leu Glu Lys Asp Ile Thr Pro Leu Gln Val Val
    130                 135                 140

Leu Pro Asn Thr Ala Leu His Leu Lys Ala Leu Leu Asp Phe Glu Asp
145                 150                 155                 160

Lys Asn Gly Asp Lys Val Met Ala Gly Asp Glu Trp Leu Phe Glu Gly
                165                 170                 175

Pro Gly Thr Tyr Ile Pro Gln Lys Glu Val Glu Val Val Glu Ile Ile
            180                 185                 190

Gln Ala Thr Val Ile Lys Gln Asn Gln Ala Leu Arg Leu Arg Ala Arg
        195                 200                 205

Lys Glu Cys Phe Asp Arg Glu Gly Lys Gly Arg Val Thr Gly Glu Glu
    210                 215                 220

Trp Leu Val Arg Ser Val Gly Ala Tyr Leu Pro Ala Val Phe Glu Glu
225                 230                 235                 240

Val Leu Asp Leu Val Asp Ala Val Ile Leu Thr Glu Lys Thr Ala Leu
                245                 250                 255

His Leu Arg Ala Leu Gln Asn Phe Arg Asp Leu Arg Gly Val Leu His
            260                 265                 270

Arg Thr Gly Glu Glu Trp Leu Val Thr Val Gln Asp Thr Glu Ala His
        275                 280                 285

Val Pro Asp Val Tyr Glu Glu Val Leu Gly Val Val Pro Ile Thr Thr
    290                 295                 300

Leu Gly Pro Arg His Tyr Cys Val Ile Leu Asp Pro Met Gly Pro Asp
305                 310                 315                 320

Gly Lys Asn Gln Leu Gly Gln Lys Arg Val Val Lys Gly Glu Lys Ser
                325                 330                 335

Phe Phe Leu Gln Pro Gly Glu Arg Leu Glu Arg Gly Ile Gln Asp Val
            340                 345                 350

Tyr Val Leu Ser Glu Gln Gln Gly Leu Leu Leu Lys Ala Leu Gln Pro
        355                 360                 365
```

```
Leu Glu Glu Gly Glu Ser Glu Glu Lys Val Ser His Gln Ala Gly Asp
    370                 375                 380

Cys Trp Leu Ile Arg Gly Pro Leu Glu Tyr Val Pro Ser Ala Lys Val
385                 390                 395                 400

Glu Val Val Glu Glu Arg Gln Ala Ile Pro Leu Asp Gln Asn Glu Gly
                405                 410                 415

Ile Tyr Val Gln Asp Val Lys Thr Gly Lys Val Arg Ala Val Ile Gly
            420                 425                 430

Ser Thr Tyr Met Leu Thr Gln Asp Glu Val Leu Trp Glu Lys Glu Leu
        435                 440                 445

Pro Ser Gly Val Glu Glu Leu Leu Asn Leu Gly His Asp Pro Leu Ala
    450                 455                 460

Asp Arg Gly Gln Lys Gly Thr Ala Lys Pro Leu Gln Pro Ser Ala Pro
465                 470                 475                 480

Arg Asn Lys Thr Arg Val Val Ser Tyr Arg Val Pro His Asn Ala Ala
                485                 490                 495

Val Gln Val Tyr Asp Tyr Arg Ala Lys Arg Ala Arg Val Val Phe Gly
            500                 505                 510

Pro Glu Leu Val Thr Leu Asp Pro Glu Glu Gln Phe Thr Val Leu Ser
        515                 520                 525

Leu Ser Ala Gly Arg Pro Lys Arg Pro His Ala Arg Arg Ala Leu Cys
    530                 535                 540

Leu Leu Leu Gly Pro Asp Phe Phe Thr Asp Val Ile Thr Ile Glu Thr
545                 550                 555                 560

Ala Asp His Ala Arg Leu Gln Leu Gln Leu Ala Tyr Asn Trp His Phe
                565                 570                 575

Glu Leu Lys Asn Arg Asn Asp Pro Ala Glu Ala Ala Lys Leu Phe Ser
            580                 585                 590

Val Pro Asp Phe Val Gly Asp Ala Cys Lys Ala Ile Ala Ser Arg Val
        595                 600                 605

Arg Gly Ala Val Ala Ser Val Thr Phe Asp Asp Phe His Lys Asn Ser
    610                 615                 620

Ala Arg Ile Ile Arg Met Ala Val Phe Gly Phe Glu Met Ser Glu Asp
625                 630                 635                 640

Thr Gly Pro Asp Gly Thr Leu Leu Pro Lys Ala Arg Asp Gln Ala Val
                645                 650                 655

Phe Pro Gln Asn Gly Leu Val Val Ser Ser Val Asp Val Gln Ser Val
            660                 665                 670

Glu Pro Val Asp Gln Arg Thr Arg Asp Ala Leu Gln Arg Ser Val Gln
        675                 680                 685

Leu Ala Ile Glu Ile Thr Thr Asn Ser Gln Glu Ala Ala Ala Lys His
    690                 695                 700

Glu Ala Gln Arg Leu Glu Gln Glu Ala Arg Gly Arg Leu Glu Arg Gln
705                 710                 715                 720

Lys Ile Leu Asp Gln Ser Glu Ala Glu Lys Ala Arg Lys Glu Leu Leu
                725                 730                 735

Glu Leu Glu Ala Met Ser Met Ala Val Glu Ser Thr Gly Asn Ala Lys
            740                 745                 750

Ala Glu Ala Glu Ser Arg Ala Glu Ala Ala Arg Ile Glu Gly Glu Gly
        755                 760                 765

Ser Val Leu Gln Ala Lys Leu Lys Ala Gln Ala Leu Ala Ile Glu Thr
    770                 775                 780

Glu Ala Glu Leu Glu Arg Val Lys Lys Val Arg Glu Met Glu Leu Ile
785                 790                 795                 800
```

```
Tyr Ala Arg Ala Gln Leu Glu Leu Glu Val Ser Lys Ala Gln Gln Leu
                805                 810                 815

Ala Asn Val Glu Ala Lys Lys Phe Lys Glu Met Thr Glu Ala Leu Gly
            820                 825                 830

Pro Gly Thr Ile Arg Asp Leu Ala Val Ala Gly Pro Glu Met Gln Val
        835                 840                 845

Lys Leu Leu Gln Ser Leu Gly Leu Lys Ser Thr Leu Ile Thr Asp Gly
    850                 855                 860

Ser Ser Pro Ile Asn Leu Phe Ser Thr Ala Phe Gly Leu Leu Gly Leu
865                 870                 875                 880

Gly Ser Asp Gly Gln Pro Pro Ala Gln Lys Phe Asn Met Gln Gln Gln
                885                 890                 895

Arg Arg Phe Tyr Glu Ala Leu His Asp Pro Asn Leu Asn Glu Glu Gln
            900                 905                 910

Arg Asn Ala Lys Ile Lys Ser Ile Arg Asp Asp
        915                 920


<210> SEQ ID NO 12
<211> LENGTH: 759
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

atggccttca gctggggctc gctgtggagc ggcattaaaa atttcggttc caccgttaag     60

aactatggca gcaaggcctg gaacagcagc acaggccaga tgctgaggga taagttgaaa    120

gagcaaaatt tccaacaaaa ggtggtagat ggcctggcct ctggcattag cggggtggtg    180

gacctggcca accaggcagt gcaaaataag attaacagta agcttgatcc ccgccctccc    240

gtagagggat ccgaattcgg cacgaggcgg tgcacacaac actggcagga tgctgtgcct    300

tggacagaac tcctcagtct acagacagag gatggcttct ggaaacttac accagaactg    360

ggacttatat taaatcttaa tacaaatggt ttgcacagct ttcttaaaca aaaaggcatt    420

caatctctag gtgtaaaagg aagagaatgt ctcctggacc taattgccac aatgctggta    480

ctacagttta ttcgcaccag gttggaaaaa gagggaatag tgttcaaatc actgatgaaa    540

atggatgacc cttctatttc caggaatatt ccctgggctt ttgaggcaat aaagcaagca    600

agtgaatggg taagaagaac tgaaggacag tacccatcta tctgcccacg gcttgaactg    660

gggaacgact gggactctgc caccaagcag ttgctgggac tccagcccat aagcactgtg    720

tcccctcttc atagagtcct ccattacagt caaggctaa                           759


<210> SEQ ID NO 13
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Ala Phe Ser Trp Gly Ser Leu Trp Ser Gly Ile Lys Asn Phe Gly
1               5                   10                  15

Ser Thr Val Lys Asn Tyr Gly Ser Lys Ala Trp Asn Ser Ser Thr Gly
            20                  25                  30

Gln Met Leu Arg Asp Lys Leu Lys Glu Gln Asn Phe Gln Gln Lys Val
```

```
        35                  40                  45

Val Asp Gly Leu Ala Ser Gly Ile Ser Gly Val Val Asp Leu Ala Asn
    50                  55                  60

Gln Ala Val Gln Asn Lys Ile Asn Ser Lys Leu Asp Pro Arg Pro Pro
65                  70                  75                  80

Val Glu Gly Ser Glu Phe Gly Thr Arg Arg Cys Thr Gln His Trp Gln
                85                  90                  95

Asp Ala Val Pro Trp Thr Glu Leu Leu Ser Leu Gln Thr Glu Asp Gly
            100                 105                 110

Phe Trp Lys Leu Thr Pro Glu Leu Gly Leu Ile Leu Asn Leu Asn Thr
        115                 120                 125

Asn Gly Leu His Ser Phe Leu Lys Gln Lys Gly Ile Gln Ser Leu Gly
    130                 135                 140

Val Lys Gly Arg Glu Cys Leu Leu Asp Leu Ile Ala Thr Met Leu Val
145                 150                 155                 160

Leu Gln Phe Ile Arg Thr Arg Leu Glu Lys Glu Gly Ile Val Phe Lys
                165                 170                 175

Ser Leu Met Lys Met Asp Asp Pro Ser Ile Ser Arg Asn Ile Pro Trp
            180                 185                 190

Ala Phe Glu Ala Ile Lys Gln Ala Ser Glu Trp Val Arg Arg Thr Glu
        195                 200                 205

Gly Gln Tyr Pro Ser Ile Cys Pro Arg Leu Glu Leu Gly Asn Asp Trp
    210                 215                 220

Asp Ser Ala Thr Lys Gln Leu Leu Gly Leu Gln Pro Ile Ser Thr Val
225                 230                 235                 240

Ser Pro Leu His Arg Val Leu His Tyr Ser Gln Gly
                245                 250


<210> SEQ ID NO 14
<211> LENGTH: 1724
<212> TYPE: PRT
<213> ORGANISM: Homo sapiens

<400> SEQUENCE: 14

Met Val Met Gly Ile Phe Ala Asn Cys Ile Phe Cys Leu Lys Val Lys
1               5                   10                  15

Tyr Leu Pro Gln Gln Gln Lys Lys Lys Leu Gln Thr Asp Ile Lys Glu
            20                  25                  30

Asn Gly Gly Lys Phe Ser Phe Ser Leu Asn Pro Gln Cys Thr His Ile
        35                  40                  45

Ile Leu Asp Asn Ala Asp Val Leu Ser Gln Tyr Gln Leu Asn Ser Ile
    50                  55                  60

Gln Lys Asn His Val His Ile Ala Asn Pro Asp Phe Ile Trp Lys Ser
65                  70                  75                  80

Ile Arg Glu Lys Arg Leu Leu Asp Val Lys Asn Tyr Asp Pro Tyr Lys
                85                  90                  95

Pro Leu Asp Ile Thr Pro Pro Pro Asp Gln Lys Ala Ser Ser Ser Glu
            100                 105                 110

Val Lys Thr Glu Gly Leu Cys Pro Asp Ser Ala Thr Glu Glu Glu Asp
        115                 120                 125

Thr Val Glu Leu Thr Glu Phe Gly Met Gln Asn Val Glu Ile Pro His
    130                 135                 140

Leu Pro Gln Asp Phe Glu Val Ala Lys Tyr Asn Thr Leu Glu Lys Val
145                 150                 155                 160

Gly Met Glu Gly Gly Gln Glu Ala Val Val Val Glu Leu Gln Cys Ser
```

```
                165                 170                 175

Arg Asp Ser Arg Asp Cys Pro Phe Leu Ile Ser Ser His Phe Leu Leu
            180                 185                 190

Asp Asp Gly Met Glu Thr Arg Arg Gln Phe Ala Ile Lys Lys Thr Ser
        195                 200                 205

Glu Asp Ala Ser Glu Tyr Phe Glu Asn Tyr Ile Glu Glu Leu Lys Lys
    210                 215                 220

Gln Gly Phe Leu Leu Arg Glu His Phe Thr Pro Glu Ala Thr Gln Leu
225                 230                 235                 240

Ala Ser Glu Gln Leu Gln Ala Leu Leu Leu Glu Glu Val Met Asn Ser
                245                 250                 255

Ser Thr Leu Ser Gln Glu Val Ser Asp Leu Val Glu Met Ile Trp Ala
            260                 265                 270

Glu Ala Leu Gly His Leu Glu His Met Leu Leu Lys Pro Val Asn Arg
        275                 280                 285

Ile Ser Leu Asn Asp Val Ser Lys Ala Glu Gly Ile Leu Leu Leu Val
    290                 295                 300

Lys Ala Ala Leu Lys Asn Gly Glu Thr Ala Glu Gln Leu Gln Lys Met
305                 310                 315                 320

Met Thr Glu Phe Tyr Arg Leu Ile Pro His Lys Gly Thr Met Pro Lys
                325                 330                 335

Glu Val Asn Leu Gly Leu Leu Ala Lys Lys Ala Asp Leu Cys Gln Leu
            340                 345                 350

Ile Arg Asp Met Val Asn Val Cys Glu Thr Asn Leu Ser Lys Pro Asn
        355                 360                 365

Pro Pro Ser Leu Ala Lys Tyr Arg Ala Leu Arg Cys Lys Ile Glu His
    370                 375                 380

Val Glu Gln Asn Thr Glu Glu Phe Leu Arg Val Arg Lys Glu Val Leu
385                 390                 395                 400

Gln Asn His His Ser Lys Ser Pro Val Asp Val Leu Gln Ile Phe Arg
                405                 410                 415

Val Gly Arg Val Asn Glu Thr Thr Glu Phe Leu Ser Lys Leu Gly Asn
            420                 425                 430

Val Arg Pro Leu Leu His Gly Ser Pro Val Gln Asn Ile Val Gly Ile
        435                 440                 445

Leu Cys Arg Gly Leu Leu Leu Pro Lys Val Val Glu Asp Arg Gly Val
    450                 455                 460

Gln Arg Thr Asp Val Gly Asn Leu Gly Ser Gly Ile Tyr Phe Ser Asp
465                 470                 475                 480

Ser Leu Ser Thr Ser Ile Lys Tyr Ser His Pro Gly Glu Thr Asp Gly
                485                 490                 495

Thr Arg Leu Leu Leu Ile Cys Asp Val Ala Leu Gly Lys Cys Met Asp
            500                 505                 510

Leu His Glu Lys Asp Phe Pro Leu Thr Glu Ala Pro Pro Gly Tyr Asp
        515                 520                 525

Ser Val His Gly Val Ser Gln Thr Ala Ser Val Thr Thr Asp Phe Glu
    530                 535                 540

Asp Asp Glu Phe Val Val Tyr Lys Thr Asn Gln Val Lys Met Lys Tyr
545                 550                 555                 560

Ile Ile Lys Phe Ser Met Pro Gly Asp Gln Ile Lys Asp Phe His Pro
                565                 570                 575

Ser Asp His Thr Glu Leu Glu Glu Tyr Arg Pro Glu Phe Ser Asn Phe
            580                 585                 590
```

```
Ser Lys Val Glu Asp Tyr Gln Leu Pro Asp Ala Lys Thr Ser Ser Ser
        595                 600                 605

Thr Lys Ala Gly Leu Gln Asp Ala Ser Gly Asn Leu Val Pro Leu Glu
    610                 615                 620

Asp Val His Ile Lys Gly Arg Ile Ile Asp Thr Val Ala Gln Val Ile
625                 630                 635                 640

Val Phe Gln Thr Tyr Thr Asn Lys Ser His Val Pro Ile Glu Ala Lys
                645                 650                 655

Tyr Ile Phe Pro Leu Asp Asp Lys Ala Ala Val Cys Gly Phe Glu Ala
            660                 665                 670

Phe Ile Asn Gly Lys His Ile Val Gly Glu Ile Lys Glu Lys Glu Glu
        675                 680                 685

Ala Gln Gln Glu Tyr Leu Glu Ala Val Thr Gln Gly His Gly Ala Tyr
    690                 695                 700

Leu Met Ser Gln Asp Ala Pro Asp Val Phe Thr Val Ser Val Gly Asn
705                 710                 715                 720

Leu Pro Pro Lys Ala Lys Val Leu Ile Lys Ile Thr Tyr Ile Thr Glu
                725                 730                 735

Leu Ser Ile Leu Gly Thr Val Gly Val Phe Phe Met Pro Ala Thr Val
            740                 745                 750

Ala Pro Trp Gln Gln Asp Lys Ala Leu Asn Glu Asn Leu Gln Asp Thr
        755                 760                 765

Val Glu Lys Ile Cys Ile Lys Glu Ile Gly Thr Lys Gln Ser Phe Ser
    770                 775                 780

Leu Thr Met Ser Ile Glu Met Pro Tyr Val Ile Glu Phe Ile Phe Ser
785                 790                 795                 800

Asp Thr His Glu Leu Lys Gln Lys Arg Thr Asp Cys Lys Ala Val Ile
                805                 810                 815

Ser Thr Met Glu Gly Ser Ser Leu Asp Ser Ser Gly Phe Ser Leu His
            820                 825                 830

Ile Gly Leu Ser Ala Ala Tyr Leu Pro Arg Met Trp Val Glu Lys His
        835                 840                 845

Pro Glu Lys Glu Ser Glu Ala Cys Met Leu Val Phe Gln Pro Asp Leu
    850                 855                 860

Asp Val Asp Leu Pro Asp Leu Ala Ser Glu Ser Glu Val Ile Ile Cys
865                 870                 875                 880

Leu Asp Cys Ser Ser Ser Met Glu Gly Val Thr Phe Leu Gln Ala Lys
                885                 890                 895

Gln Ile Thr Leu His Ala Leu Ser Leu Val Gly Glu Lys Gln Lys Val
            900                 905                 910

Asn Ile Ile Gln Phe Gly Thr Gly Tyr Lys Glu Leu Phe Ser Tyr Pro
        915                 920                 925

Lys His Ile Thr Ser Asn Thr Thr Ala Ala Glu Phe Ile Met Ser Ala
    930                 935                 940

Thr Pro Thr Met Gly Asn Thr Asp Phe Trp Lys Thr Leu Arg Tyr Leu
945                 950                 955                 960

Ser Leu Leu Tyr Pro Ala Arg Gly Ser Arg Asn Ile Leu Leu Val Ser
                965                 970                 975

Asp Gly His Leu Gln Asp Glu Ser Leu Thr Leu Gln Leu Val Lys Arg
            980                 985                 990

Ser Arg Pro His Thr Arg Leu Phe  Ala Cys Gly Ile Gly  Ser Thr Ala
        995                 1000                 1005

Asn Arg  His Val Leu Arg Ile  Leu Ser Gln Cys Gly  Ala Gly Val
    1010                 1015                 1020
```

```
Phe Glu  Tyr Phe Asn Ala Lys  Ser Lys His Ser Trp  Arg Lys Gln
    1025                 1030                 1035

Ile Glu  Asp Gln Met Thr Arg  Leu Cys Ser Pro Ser  Cys His Ser
    1040                 1045                 1050

Val Ser  Val Lys Trp Gln Gln  Leu Asn Pro Asp Ala  Pro Glu Ala
    1055                 1060                 1065

Leu Gln  Ala Pro Ala Gln Val  Pro Ser Leu Phe Arg  Asn Asp Arg
    1070                 1075                 1080

Leu Leu  Val Tyr Gly Phe Ile  Pro His Cys Thr Gln  Ala Thr Leu
    1085                 1090                 1095

Cys Ala  Leu Ile Gln Glu Lys  Glu Phe Cys Thr Met  Val Ser Thr
    1100                 1105                 1110

Thr Glu  Leu Gln Lys Thr Thr  Gly Thr Met Ile His  Lys Leu Ala
    1115                 1120                 1125

Ala Arg  Ala Leu Ile Arg Asp  Tyr Glu Asp Gly Ile  Leu His Glu
    1130                 1135                 1140

Asn Glu  Thr Ser His Glu Met  Lys Lys Gln Thr Leu  Lys Ser Leu
    1145                 1150                 1155

Ile Ile  Lys Leu Ser Lys Glu  Asn Ser Leu Ile Thr  Gln Phe Thr
    1160                 1165                 1170

Ser Phe  Val Ala Val Glu Lys  Arg Asp Glu Asn Glu  Ser Pro Phe
    1175                 1180                 1185

Pro Asp  Ile Pro Lys Val Ser  Glu Leu Ile Ala Lys  Glu Asp Val
    1190                 1195                 1200

Asp Phe  Leu Pro Tyr Met Ser  Trp Gln Gly Glu Pro  Gln Glu Ala
    1205                 1210                 1215

Val Arg  Asn Gln Ser Leu Leu  Ala Ser Ser Glu Trp  Pro Glu Leu
    1220                 1225                 1230

Arg Leu  Ser Lys Arg Lys His  Arg Lys Ile Pro Phe  Ser Lys Arg
    1235                 1240                 1245

Lys Met  Glu Leu Ser Gln Pro  Glu Val Ser Glu Asp  Phe Glu Glu
    1250                 1255                 1260

Asp Gly  Leu Gly Val Leu Pro  Ala Phe Thr Ser Asn  Leu Glu Arg
    1265                 1270                 1275

Gly Gly  Val Glu Lys Leu Leu  Asp Leu Ser Trp Thr  Glu Ser Cys
    1280                 1285                 1290

Lys Pro  Thr Ala Thr Glu Pro  Leu Phe Lys Lys Val  Ser Pro Trp
    1295                 1300                 1305

Glu Thr  Ser Thr Ser Ser Phe  Phe Pro Ile Leu Ala  Pro Ala Val
    1310                 1315                 1320

Gly Ser  Tyr Leu Thr Pro Thr  Thr Arg Ala His Ser  Pro Ala Ser
    1325                 1330                 1335

Leu Ser  Phe Ala Ser Tyr Arg  Gln Val Ala Ser Phe  Gly Ser Ala
    1340                 1345                 1350

Ala Pro  Pro Arg Gln Phe Asp  Ala Ser Gln Phe Ser  Gln Gly Pro
    1355                 1360                 1365

Val Pro  Gly Thr Cys Ala Asp  Trp Ile Pro Gln Ser  Ala Ser Cys
    1370                 1375                 1380

Pro Thr  Gly Pro Pro Gln Asn  Pro Pro Ser Ala Pro  Tyr Cys Gly
    1385                 1390                 1395

Ile Val  Phe Ser Gly Ser Ser  Leu Ser Ser Ala Gln  Ser Ala Pro
    1400                 1405                 1410

Leu Gln  His Pro Gly Gly Phe  Thr Thr Arg Pro Ser  Ala Gly Thr
```

```
    1415                1420                1425

Phe Pro  Glu Leu Asp Ser Pro  Gln Leu His Phe Ser  Leu Pro Thr
    1430                1435                1440

Asp Pro  Asp Pro Ile Arg Gly  Phe Gly Ser Tyr His  Pro Ser Ala
    1445                1450                1455

Tyr Ser  Pro Phe His Phe Gln  Pro Ser Ala Ala Ser  Leu Thr Ala
    1460                1465                1470

Asn Leu  Arg Leu Pro Met Ala  Ser Ala Leu Pro Glu  Ala Leu Cys
    1475                1480                1485

Ser Gln  Ser Arg Thr Thr Pro  Val Asp Leu Cys Leu  Leu Glu Glu
    1490                1495                1500

Ser Val  Gly Ser Leu Glu Gly  Ser Arg Cys Pro Val  Phe Ala Phe
    1505                1510                1515

Gln Ser  Ser Asp Thr Glu Ser  Asp Glu Leu Ser Glu  Val Leu Gln
    1520                1525                1530

Asp Ser  Cys Phe Leu Gln Ile  Lys Cys Asp Thr Lys  Asp Asp Ser
    1535                1540                1545

Ile Pro  Cys Phe Leu Glu Leu  Lys Glu Glu Asp Glu  Ile Val Cys
    1550                1555                1560

Thr Gln  His Trp Gln Asp Ala  Val Pro Trp Thr Glu  Leu Leu Ser
    1565                1570                1575

Leu Gln  Thr Glu Asp Gly Phe  Trp Lys Leu Thr Pro  Glu Leu Gly
    1580                1585                1590

Leu Ile  Leu Asn Leu Asn Thr  Asn Gly Leu His Ser  Phe Leu Lys
    1595                1600                1605

Gln Lys  Gly Ile Gln Ser Leu  Gly Val Lys Gly Arg  Glu Cys Leu
    1610                1615                1620

Leu Asp  Leu Ile Ala Thr Met  Leu Val Leu Gln Phe  Ile Arg Thr
    1625                1630                1635

Arg Leu  Glu Lys Glu Gly Ile  Val Phe Lys Ser Leu  Met Lys Met
    1640                1645                1650

Asp Asp  Pro Ser Ile Ser Arg  Asn Ile Pro Trp Ala  Phe Glu Ala
    1655                1660                1665

Ile Lys  Gln Ala Ser Glu Trp  Val Arg Arg Thr Glu  Gly Gln Tyr
    1670                1675                1680

Pro Ser  Ile Cys Pro Arg Leu  Glu Leu Gly Asn Asp  Trp Asp Ser
    1685                1690                1695

Ala Thr  Lys Gln Leu Leu Gly  Leu Gln Pro Ile Ser  Thr Val Ser
    1700                1705                1710

Pro Leu  His Arg Val Leu His  Tyr Ser Gln Gly
    1715                1720
```

<210> SEQ ID NO 15
<211> LENGTH: 5175
<212> TYPE: DNA
<213> ORGANISM: Homo sapiens

<400> SEQUENCE: 15

```
atggtgatgg gaatctttgc aaattgtatc ttctgtttga aagtgaagta cttacctcag     60

cagcagaaga aaaagctaca aactgacatt aaggaaaatg gcggaaagtt ttccttttcg    120

ttaaatcctc agtgcacaca tataatctta gataatgctg atgttctgag tcagtaccaa    180

ctgaattcta tccaaaagaa ccacgttcat attgcaaacc cagattttat atggaaatct    240

atcagagaaa agagactctt ggatgtaaag aattatgatc cttataagcc cctggacatc    300
```

```
acaccacctc ctgatcagaa ggcgagcagt tctgaagtga aaacagaagg tctatgcccg    360
gacagtgcca cagaggagga agacactgtg gaactcactg agtttggtat gcagaatgtt    420
gaaattcctc atcttcctca agattttgaa gttgcaaaat ataacacctt ggagaaagtg    480
ggaatggagg gaggccagga agctgtggtg gtggagcttc agtgttcgcg ggactccagg    540
gactgtcctt tcctgatatc ctcacacttc ctcctggatg atggcatgga gactagaaga    600
cagtttgcta taaagaaaac ctctgaagat gcaagtgaat actttgaaaa ttacattgaa    660
gaactgaaga aacaaggatt tctactaaga gaacatttca cacctgaagc aacccaatta    720
gcatctgaac aattgcaagc attgcttttg gaggaagtca tgaattcaag cactctgagc    780
caagaggtga gcgatttagt agagatgatt tgggcagagg ccctgggcca cctggaacac    840
atgcttctca agccagtgaa caggattagc ctcaacgatg tgagcaaggc agaggggatt    900
ctccttctag taaaggcagc actgaaaaat ggagaaacag cagagcaatt gcaaaagatg    960
atgacagagt tttacagact gatacctcac aaaggcacaa tgcccaaaga agtgaacctg   1020
ggactattgg ctaagaaagc agacctctgc cagctaataa gagacatggt taatgtctgt   1080
gaaactaatt tgtccaaacc caacccacca tccctggcca aataccgagc tttgaggtgc   1140
aaaattgagc atgttgaaca gaatactgaa gaatttctca gggttagaaa agaggttttg   1200
cagaatcatc acagtaagag cccagtggat gtcttgcaga tatttagagt tggcagagtg   1260
aatgaaacca cagagttttt gagcaaactt ggtaatgtga ggcccttgtt gcatggttct   1320
cctgtacaaa acatcgtggg aatcttgtgt cgagggttgc ttttacccaa agtagtggaa   1380
gatcgtggtg tgcaaagaac agacgtcgga aaccttggaa gtgggattta tttcagtgat   1440
tcgctcagta caagtatcaa gtactcacac ccgggagaga cagatggcac cagactcctg   1500
ctcatttgtg acgtagccct cggaaagtgt atggacttac atgagaagga ctttccctta   1560
actgaagcac caccaggcta cgacagtgtg catggagttt cacaaacagc ctctgtcacc   1620
acagactttg aggatgatga atttgttgtc tataaaacca atcaggttaa aatgaaatat   1680
attattaaat tttccatgcc tggagatcag ataaaggact ttcatcctag tgatcatact   1740
gaattagagg aatacagacc tgagttttca aatttttcaa aggttgaaga ttaccagtta   1800
ccagatgcca aaacttccag cagcaccaag gccggcctcc aggatgcctc tgggaacttg   1860
gttcctctgg aggatgtcca catcaaaggg agaatcatag acactgtagc ccaggtcatt   1920
gtttttcaga catacacaaa taaaagtcac gtgcccattg aggcaaaata tatctttcct   1980
ttggatgaca aggccgctgt gtgtggcttc gaagccttca tcaatgggaa gcacatagtt   2040
ggagagatta aagagaagga agaagcccag caagagtacc tagaagccgt gacccagggc   2100
catggcgctt acctgatgag tcaggatgct ccggacgttt ttactgtaag tgttggaaac   2160
ttacccccta aggctaaggt tcttataaaa attacctaca tcacagaact cagcatcctg   2220
ggcactgttg gtgtcttttt catgcccgcc accgtagcac cctggcaaca ggacaaggct   2280
ttgaatgaaa accttcagga tacagtagag aagatttgta taaaagaaat aggaacaaag   2340
caaagcttct ctttgactat gtctattgag atgccgtatg tgattgaatt cattttcagt   2400
gatacacatg aactgaaaca aaagcgcaca gactgcaaag ctgtcattag caccatggaa   2460
ggcagctcct tagacagcag tggattttct ctccacatcg gtttgtctgc tgcctatctc   2520
ccaagaatgt gggttgaaaa acatccagaa aaagaaagcg aggcttgcat gcttgtcttt   2580
caacccgatc tcgatgtcga cctccctgac ctagccagtg agagcgaagt gattatttgt   2640
cttgactgct ccagttccat ggagggtgtg acattcttgc aagccaagca aatcaccttg   2700
```

```
catgcgctgt ccttggtggg tgagaagcag aaagtaaata ttatccagtt cggcacaggt   2760
tacaaggagc tattttcgta tcctaagcat atcacaagca ataccacggc agcagagttc   2820
atcatgtctg ccacacctac catggggaac acagacttct ggaaaacact ccgatatctt   2880
agcttattgt accctgctcg agggtcacgg aacatcctcc tggtgtctga tgggcacctc   2940
caggatgaga gcctgacatt acagctcgtg aagaggagcc gcccgcacac caggttattc   3000
gcctgcggta tcggttctac agcaaatcgt cacgtcttaa ggattttgtc ccagtgtggt   3060
gccggagtat ttgaatattt taatgcaaaa tccaagcata gttggagaaa acagatagaa   3120
gaccaaatga ccaggctatg ttctccgagt tgccactctg tctccgtcaa atggcagcaa   3180
ctcaatccag atgcgcccga ggccctgcag gccccagccc aggtgccatc cttgtttcgc   3240
aatgatcgac tccttgtcta tggattcatt cctcactgca cacaagcaac tctgtgtgca   3300
ctaattcaag agaaagaatt ttgtacaatg gtgtcgacta ctgagcttca gaagacaact   3360
ggaactatga tccacaagct ggcagcccga gctctaatca gagattatga agatggcatt   3420
cttcacgaaa atgaaaccag tcatgagatg aaaaaacaaa ccttgaaatc tctgattatt   3480
aaactcagta aagaaaactc tctcataaca caatttacaa gctttgtggc agttgagaaa   3540
agggatgaga atgagtcgcc ttttcctgat attccaaaag tttctgaact tattgccaaa   3600
gaagatgtag acttcctgcc ctacatgagc tggcaggggg agccccaaga agccgtcagg   3660
aaccagtctc ttttagcatc ctctgagtgg ccagaattac gtttatccaa acgaaaacat   3720
aggaaaattc cattttccaa aagaaaaatg gaattatctc agccagaagt ttctgaagat   3780
tttgaagagg atggcttagg tgtactacca gctttcacat caaatttgga acgtggaggt   3840
gtggaaaagc tattggattt aagttggaca gagtcatgta aaccaacagc aactgaacca   3900
ctatttaaga aagtcagtcc atgggaaaca tctacttcta gctttttttcc tattttggct   3960
ccggccgttg gttcctatct taccccgact acccgcgctc acagtcctgc ttccttgtct   4020
tttgcctcat atcgtcaggt agctagtttc ggttcagctg ctcctcccag acagtttgat   4080
gcatctcaat tcagccaagg ccctgtgcct ggcacttgtg ctgactggat cccacagtcg   4140
gcgtcttgtc ccacaggacc tccccagaac ccaccttctg caccctattg tggcattgtt   4200
ttttcaggga gctcattaag ctctgcacag tctgctccac tgcaacatcc tggaggcttt   4260
actaccaggc cttctgctgg caccttccct gagctggatt ctccccagct tcatttctct   4320
cttcctacag accctgatcc catcagaggt tttgggtctt atcatccctc tgcttactct   4380
ccttttcatt ttcaaccttc cgcagcctct ttgactgcca accttaggct gccaatggcc   4440
tctgctttac ctgaggctct ttgcagtcag tcccggacta ccccagtaga tctctgtctt   4500
ctagaagaat cagtaggcag tctcgaagga agtcgatgtc ctgtctttgc ttttcaaagt   4560
tctgacacag aaagtgatga gctatcagaa gtacttcaag acagctgctt tttacaaata   4620
aagtgtgata caaaagatga cagtatcccg tgctttctgg aattaaaaga agaggatgaa   4680
atagtgtgca cacaacactg gcaggatgct gtgccttgga cagaactcct cagtctacag   4740
acagaggatg gcttctggaa acttacacca gaactgggac ttatattaaa tcttaataca   4800
aatggtttgc acagctttct taaacaaaaa ggcattcaat ctctaggtgt aaaaggaaga   4860
gaatgtctcc tggacctaat tgccacaatg ctggtactac agtttattcg caccaggttg   4920
gaaaaagagg gaatagtgtt caaatcactg atgaaaatgg atgacccttc tatttccagg   4980
aatattccct gggcttttga ggcaataaag caagcaagtg aatgggtaag aagaactgaa   5040
ggacagtacc catctatctg cccacggctt gaactgggga acgactggga ctctgccacc   5100
```

aagcagttgc tgggactcca gcccataagc actgtgtccc ctcttcatag agtcctccat 5160
tacagtcaag gctaa 5175

<210> SEQ ID NO 16
<211> LENGTH: 893
<212> TYPE: PRT
<213> ORGANISM: Homo sapiens

<400> SEQUENCE: 16

Met Ala Thr Glu Glu Phe Ile Ile Arg Ile Pro Pro Tyr His Tyr Ile
1 5 10 15

His Val Leu Asp Gln Asn Ser Asn Val Ser Arg Val Glu Val Gly Pro
20 25 30

Lys Thr Tyr Ile Arg Gln Asp Asn Glu Arg Val Leu Phe Ala Pro Met
35 40 45

Arg Met Val Thr Val Pro Pro Arg His Tyr Cys Thr Val Ala Asn Pro
50 55 60

Val Ser Arg Asp Ala Gln Gly Leu Val Leu Phe Asp Val Thr Gly Gln
65 70 75 80

Val Arg Leu Arg His Ala Asp Leu Glu Ile Arg Leu Ala Gln Asp Pro
85 90 95

Phe Pro Leu Tyr Pro Gly Glu Val Leu Glu Lys Asp Ile Thr Pro Leu
100 105 110

Gln Val Val Leu Pro Asn Thr Ala Leu His Leu Lys Ala Leu Leu Asp
115 120 125

Phe Glu Asp Lys Asp Gly Asp Lys Val Val Ala Gly Asp Glu Trp Leu
130 135 140

Phe Glu Gly Pro Gly Thr Tyr Ile Pro Arg Lys Glu Val Glu Val Val
145 150 155 160

Glu Ile Ile Gln Ala Thr Ile Ile Arg Gln Asn Gln Ala Leu Arg Leu
165 170 175

Arg Ala Arg Lys Glu Cys Trp Asp Arg Asp Gly Lys Glu Arg Val Thr
180 185 190

Gly Glu Glu Trp Leu Val Thr Thr Val Gly Ala Tyr Leu Pro Ala Val
195 200 205

Phe Glu Glu Val Leu Asp Leu Val Asp Ala Val Ile Leu Thr Glu Lys
210 215 220

Thr Ala Leu His Leu Arg Ala Arg Arg Asn Phe Arg Asp Phe Arg Gly
225 230 235 240

Val Ser Arg Arg Thr Gly Glu Glu Trp Leu Val Thr Val Gln Asp Thr
245 250 255

Glu Ala His Val Pro Asp Val His Glu Glu Val Leu Gly Val Val Pro
260 265 270

Ile Thr Thr Leu Gly Pro His Asn Tyr Cys Val Ile Leu Asp Pro Val
275 280 285

Gly Pro Asp Gly Lys Asn Gln Leu Gly Gln Lys Arg Val Val Lys Gly
290 295 300

Glu Lys Ser Phe Phe Leu Gln Pro Gly Glu Gln Leu Glu Gln Gly Ile
305 310 315 320

Gln Asp Val Tyr Val Leu Ser Glu Gln Gln Gly Leu Leu Leu Arg Ala
325 330 335

Leu Gln Pro Leu Glu Glu Gly Glu Asp Glu Glu Lys Val Ser His Gln
340 345 350

Ala Gly Asp His Trp Leu Ile Arg Gly Pro Leu Glu Tyr Val Pro Ser
355 360 365

```
Ala Lys Val Glu Val Val Glu Glu Arg Gln Ala Ile Pro Leu Asp Glu
    370                 375                 380

Asn Glu Gly Ile Tyr Val Gln Asp Val Lys Thr Gly Lys Val Arg Ala
385                 390                 395                 400

Val Ile Gly Ser Thr Tyr Met Leu Thr Gln Asp Glu Val Leu Trp Glu
                405                 410                 415

Lys Glu Leu Pro Pro Gly Val Glu Glu Leu Leu Asn Lys Gly Gln Asp
            420                 425                 430

Pro Leu Ala Asp Arg Gly Glu Lys Asp Thr Ala Lys Ser Leu Gln Pro
        435                 440                 445

Leu Ala Pro Arg Asn Lys Thr Arg Val Val Ser Tyr Arg Val Pro His
    450                 455                 460

Asn Ala Ala Val Gln Val Tyr Asp Tyr Arg Glu Lys Arg Ala Arg Val
465                 470                 475                 480

Val Phe Gly Pro Glu Leu Val Ser Leu Gly Pro Glu Glu Gln Phe Thr
                485                 490                 495

Val Leu Ser Leu Ser Ala Gly Arg Pro Lys Arg Pro His Ala Arg Arg
            500                 505                 510

Ala Leu Cys Leu Leu Leu Gly Pro Asp Phe Phe Thr Asp Val Ile Thr
        515                 520                 525

Ile Glu Thr Ala Asp His Ala Arg Leu Gln Leu Gln Leu Ala Tyr Asn
    530                 535                 540

Trp His Phe Glu Val Asn Asp Arg Lys Asp Pro Gln Glu Thr Ala Lys
545                 550                 555                 560

Leu Phe Ser Val Pro Asp Phe Val Gly Asp Ala Cys Lys Ala Ile Ala
                565                 570                 575

Ser Arg Val Arg Gly Ala Val Ala Ser Val Thr Phe Asp Asp Phe His
            580                 585                 590

Lys Asn Ser Ala Arg Ile Ile Arg Thr Ala Val Phe Gly Phe Glu Thr
        595                 600                 605

Ser Glu Ala Lys Gly Pro Asp Gly Met Ala Leu Pro Arg Pro Arg Asp
    610                 615                 620

Gln Ala Val Phe Pro Gln Asn Gly Leu Val Val Ser Ser Val Asp Val
625                 630                 635                 640

Gln Ser Val Glu Pro Val Asp Gln Arg Thr Arg Asp Ala Leu Gln Arg
                645                 650                 655

Ser Val Gln Leu Ala Ile Glu Ile Thr Thr Asn Ser Gln Glu Ala Ala
            660                 665                 670

Ala Lys His Glu Ala Gln Arg Leu Glu Gln Glu Ala Arg Gly Arg Leu
        675                 680                 685

Glu Arg Gln Lys Ile Leu Asp Gln Ser Glu Ala Glu Lys Ala Arg Lys
    690                 695                 700

Glu Leu Leu Glu Leu Glu Ala Leu Ser Met Ala Val Glu Ser Thr Gly
705                 710                 715                 720

Thr Ala Lys Ala Glu Ala Glu Ser Arg Ala Glu Ala Ala Arg Ile Glu
                725                 730                 735

Gly Glu Gly Ser Val Leu Gln Ala Lys Leu Lys Ala Gln Ala Leu Ala
            740                 745                 750

Ile Glu Thr Glu Ala Glu Leu Gln Arg Val Gln Lys Val Arg Glu Leu
        755                 760                 765

Glu Leu Val Tyr Ala Arg Ala Gln Leu Glu Leu Glu Val Ser Lys Ala
    770                 775                 780

Gln Gln Leu Ala Glu Val Glu Val Lys Lys Phe Lys Gln Met Thr Glu
```

785 790 795 800

Ala Ile Gly Pro Ser Thr Ile Arg Asp Leu Ala Val Ala Gly Pro Glu
805 810 815

Met Gln Val Lys Leu Leu Gln Ser Leu Gly Leu Lys Ser Thr Leu Ile
820 825 830

Thr Asp Gly Ser Thr Pro Ile Asn Leu Phe Asn Thr Ala Phe Gly Leu
835 840 845

Leu Gly Met Gly Pro Glu Gly Gln Pro Leu Gly Arg Arg Val Ala Ser
850 855 860

Gly Pro Ser Pro Gly Glu Gly Ile Ser Pro Gln Ser Ala Gln Ala Pro
865 870 875 880

Gln Ala Pro Gly Asp Asn His Val Val Pro Val Leu Arg
885 890

<210> SEQ ID NO 17
<211> LENGTH: 2682
<212> TYPE: DNA
<213> ORGANISM: Homo sapiens

<400> SEQUENCE: 17
atggcaactg aagagttcat catccgcatc cccccatacc actatatcca tgtgctggac 60
cagaacagca acgtgtcccg tgtggaggtc gggccaaaga cctacatccg gcaggacaat 120
gagagggtac tgtttgcccc catgcgcatg gtgaccgtcc ccccacgtca ctactgcaca 180
gtggccaacc ctgtgtctcg ggatgcccag ggcttggtgc tgtttgatgt cacagggcaa 240
gttcggcttc gccacgctga cctcgagatc cggctggccc aggacccctt cccccctgtac 300 ccaggggagg tgctggaaaa ggacatcaca cccctgcagg tggttctgcc caacactgcc 360
ctccatctaa aggcgctgct tgattttgag gataaagatg gagacaaggt ggtggcagga 420
gatgagtggc ttttcgaggg acctggcacg tacatccccc ggaaggaagt ggaggtcgtg 480
gagatcattc aggccaccat catcaggcag aaccaggctc tgcggctcag ggcccgcaag 540
gagtgctggg accgggacgg caaggagagg gtgacagggg aagaatggct ggtcaccaca 600
gtaggggcgt acctcccagc ggtgtttgag gaggttctgg atttggtgga cgccgtcatc 660
cttacggaaa agacagccct gcacctccgg gctcggcgga acttccggga cttcagggga 720
gtgtcccgcc gcactgggga ggagtggctg gtaacagtgc aggacacaga ggcccacgtg 780
ccagatgtcc acgaggaggt gctgggggtt gtgcccatca ccaccctggg cccccacaac 840
tactgcgtga ttctcgaccc tgtcggaccg gatggcaaga atcagctggg gcagaagcgc 900
gtggtcaagg gagagaagtc ttttttcctc cagccaggag agcagctgga acaaggcatc 960
caggatgtgt atgtgctgtc ggagcagcag gggctgctgc tgagggccct gcagcccctg 1020
gaggaggggg aggatgagga gaaggtctca caccaggctg gggaccactg gctcatccgc 1080
ggacccctgg agtatgtgcc atctgccaaa gtggaggtgg tggaggagcg ccaggccatc 1140
cctctagacg agaacgaggg catctatgtg caggatgtca agaccggaaa ggtgcgcgct 1200
gtgattggaa gcacctacat gctgacccag gacgaagtcc tgtgggagaa agagctgcct 1260
cccggggtgg aggagctgct gaacaagggg caggaccctc tggcagacag gggtgagaag 1320
gacacagcta agagcctcca gcccttggcg ccccggaaca agacccgtgt ggtcagctac 1380
cgcgtgcccc acaacgctgc ggtgcaggtg tacgactacc gagagaagcg agcccgcgtg 1440
gtcttcgggc ctgagctggt gtcgctgggt cctgaggagc agttcacagt gttgtccctc 1500
tcagctgggc ggcccaagcg tccccatgcc cgccgtgcgc tctgcctgct gctggggcct 1560

```
gacttcttca cagacgtcat caccatcgaa acggcggatc atgccaggct gcaactgcag   1620

ctggcctaca actggcactt tgaggtgaat gaccggaagg acccccaaga gacggccaag   1680

ctcttttcag tgccagactt tgtaggtgat gcctgcaaag ccatcgcatc ccgggtgcgg   1740

ggggccgtgg cctctgtcac tttcgatgac ttccataaga actcagcccg catcattcgc   1800

actgctgtct ttggctttga gacctcggaa gcgaagggcc ccgatggcat ggccctgccc   1860

aggccccggg accaggctgt cttcccccaa aacgggctgg tggtcagcag tgtggacgtg   1920

cagtcagtgg agcctgtgga tcagaggacc cgggacgccc tgcaacgcag cgtccagctg   1980

gccatcgaga tcaccaccaa ctcccaggaa gcggcggcca agcatgaggc tcagagactg   2040

gagcaggaag cccgcggccg gcttgagcgg cagaagatcc tggaccagtc agaagccgag   2100

aaagctcgca aggaactttt ggagctggag gctctgagca tggccgtgga gagcaccggg   2160

actgccaagg cggaggccga gtcccgtgcg gaggcagccc ggattgaggg agaagggtcc   2220

gtgctgcagg ccaagctaaa agcacaggcc ttggccattg aaacggaggc tgagctccag   2280

agggtccaga aggtccgaga gctggaactg gtctatgccc gggcccagct ggagctggag   2340

gtgagcaagg ctcagcagct ggctgaggtg gaggtgaaga agttcaagca gatgacagag   2400

gccataggcc ccagcaccat cagggacctt gctgtggctg ggcctgagat gcaggtaaaa   2460

ctgctccagt ccctgggcct gaaatcaacc ctcatcaccg atggctccac tcccatcaac   2520

ctcttcaaca cagcctttgg gctgctgggg atgggcccg agggtcagcc cctgggcaga   2580

agggtggcca gtgggcccag ccctggggag ggatatccc cccagtctgc tcaggcccct   2640

caagctcctg gagacaacca cgtggtgcct gtactgcgct aa                      2682
```

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

```
Met Ala Gly Cys Gly Cys Pro Cys Gly Cys Gly Ala
1               5                   10
```

<210> SEQ ID NO 19
<211> LENGTH: 905
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

```
Met Ala Gly Cys Gly Cys Pro Cys Gly Cys Gly Ala Met Ala Thr Glu
1               5                   10                  15

Glu Phe Ile Ile Arg Ile Pro Pro Tyr His Tyr Ile His Val Leu Asp
            20                  25                  30

Gln Asn Ser Asn Val Ser Arg Val Glu Val Gly Pro Lys Thr Tyr Ile
        35                  40                  45

Arg Gln Asp Asn Glu Arg Val Leu Phe Ala Pro Met Arg Met Val Thr
    50                  55                  60

Val Pro Pro Arg His Tyr Cys Thr Val Ala Asn Pro Val Ser Arg Asp
65                  70                  75                  80

Ala Gln Gly Leu Val Leu Phe Asp Val Thr Gly Gln Val Arg Leu Arg
                85                  90                  95
```

```
His Ala Asp Leu Glu Ile Arg Leu Ala Gln Asp Pro Phe Pro Leu Tyr
            100                 105                 110

Pro Gly Glu Val Leu Glu Lys Asp Ile Thr Pro Leu Gln Val Val Leu
        115                 120                 125

Pro Asn Thr Ala Leu His Leu Lys Ala Leu Leu Asp Phe Glu Asp Lys
    130                 135                 140

Asp Gly Asp Lys Val Val Ala Gly Asp Glu Trp Leu Phe Glu Gly Pro
145                 150                 155                 160

Gly Thr Tyr Ile Pro Arg Lys Glu Val Glu Val Val Glu Ile Ile Gln
                165                 170                 175

Ala Thr Ile Ile Arg Gln Asn Gln Ala Leu Arg Leu Arg Ala Arg Lys
            180                 185                 190

Glu Cys Trp Asp Arg Asp Gly Lys Glu Arg Val Thr Gly Glu Glu Trp
        195                 200                 205

Leu Val Thr Thr Val Gly Ala Tyr Leu Pro Ala Val Phe Glu Glu Val
    210                 215                 220

Leu Asp Leu Val Asp Ala Val Ile Leu Thr Glu Lys Thr Ala Leu His
225                 230                 235                 240

Leu Arg Ala Arg Arg Asn Phe Arg Asp Phe Arg Gly Val Ser Arg Arg
                245                 250                 255

Thr Gly Glu Glu Trp Leu Val Thr Val Gln Asp Thr Glu Ala His Val
            260                 265                 270

Pro Asp Val His Glu Glu Val Leu Gly Val Val Pro Ile Thr Thr Leu
        275                 280                 285

Gly Pro His Asn Tyr Cys Val Ile Leu Asp Pro Val Gly Pro Asp Gly
    290                 295                 300

Lys Asn Gln Leu Gly Gln Lys Arg Val Val Lys Gly Glu Lys Ser Phe
305                 310                 315                 320

Phe Leu Gln Pro Gly Glu Gln Leu Glu Gln Gly Ile Gln Asp Val Tyr
                325                 330                 335

Val Leu Ser Glu Gln Gln Gly Leu Leu Leu Arg Ala Leu Gln Pro Leu
            340                 345                 350

Glu Glu Gly Glu Asp Glu Glu Lys Val Ser His Gln Ala Gly Asp His
        355                 360                 365

Trp Leu Ile Arg Gly Pro Leu Glu Tyr Val Pro Ser Ala Lys Val Glu
    370                 375                 380

Val Val Glu Glu Arg Gln Ala Ile Pro Leu Asp Glu Asn Glu Gly Ile
385                 390                 395                 400

Tyr Val Gln Asp Val Lys Thr Gly Lys Val Arg Ala Val Ile Gly Ser
                405                 410                 415

Thr Tyr Met Leu Thr Gln Asp Glu Val Leu Trp Glu Lys Glu Leu Pro
            420                 425                 430

Pro Gly Val Glu Glu Leu Leu Asn Lys Gly Gln Asp Pro Leu Ala Asp
        435                 440                 445

Arg Gly Glu Lys Asp Thr Ala Lys Ser Leu Gln Pro Leu Ala Pro Arg
    450                 455                 460

Asn Lys Thr Arg Val Val Ser Tyr Arg Val Pro His Asn Ala Ala Val
465                 470                 475                 480

Gln Val Tyr Asp Tyr Arg Glu Lys Arg Ala Arg Val Val Phe Gly Pro
                485                 490                 495

Glu Leu Val Ser Leu Gly Pro Glu Glu Gln Phe Thr Val Leu Ser Leu
            500                 505                 510

Ser Ala Gly Arg Pro Lys Arg Pro His Ala Arg Arg Ala Leu Cys Leu
```

```
        515                 520                 525

Leu Leu Gly Pro Asp Phe Phe Thr Asp Val Ile Thr Ile Glu Thr Ala
    530                 535                 540

Asp His Ala Arg Leu Gln Leu Gln Leu Ala Tyr Asn Trp His Phe Glu
545                 550                 555                 560

Val Asn Asp Arg Lys Asp Pro Gln Glu Thr Ala Lys Leu Phe Ser Val
                565                 570                 575

Pro Asp Phe Val Gly Asp Ala Cys Lys Ala Ile Ala Ser Arg Val Arg
            580                 585                 590

Gly Ala Val Ala Ser Val Thr Phe Asp Asp Phe His Lys Asn Ser Ala
        595                 600                 605

Arg Ile Ile Arg Thr Ala Val Phe Gly Phe Glu Thr Ser Glu Ala Lys
    610                 615                 620

Gly Pro Asp Gly Met Ala Leu Pro Arg Pro Arg Asp Gln Ala Val Phe
625                 630                 635                 640

Pro Gln Asn Gly Leu Val Val Ser Ser Val Asp Val Gln Ser Val Glu
                645                 650                 655

Pro Val Asp Gln Arg Thr Arg Asp Ala Leu Gln Arg Ser Val Gln Leu
            660                 665                 670

Ala Ile Glu Ile Thr Thr Asn Ser Gln Glu Ala Ala Ala Lys His Glu
        675                 680                 685

Ala Gln Arg Leu Glu Gln Glu Ala Arg Gly Arg Leu Glu Arg Gln Lys
    690                 695                 700

Ile Leu Asp Gln Ser Glu Ala Glu Lys Ala Arg Lys Glu Leu Leu Glu
705                 710                 715                 720

Leu Glu Ala Leu Ser Met Ala Val Glu Ser Thr Gly Thr Ala Lys Ala
                725                 730                 735

Glu Ala Glu Ser Arg Ala Glu Ala Ala Arg Ile Glu Gly Glu Gly Ser
            740                 745                 750

Val Leu Gln Ala Lys Leu Lys Ala Gln Ala Leu Ala Ile Glu Thr Glu
        755                 760                 765

Ala Glu Leu Gln Arg Val Gln Lys Val Arg Glu Leu Glu Leu Val Tyr
    770                 775                 780

Ala Arg Ala Gln Leu Glu Leu Glu Val Ser Lys Ala Gln Gln Leu Ala
785                 790                 795                 800

Glu Val Glu Val Lys Lys Phe Lys Gln Met Thr Glu Ala Ile Gly Pro
                805                 810                 815

Ser Thr Ile Arg Asp Leu Ala Val Ala Gly Pro Glu Met Gln Val Lys
            820                 825                 830

Leu Leu Gln Ser Leu Gly Leu Lys Ser Thr Leu Ile Thr Asp Gly Ser
        835                 840                 845

Thr Pro Ile Asn Leu Phe Asn Thr Ala Phe Gly Leu Leu Gly Met Gly
    850                 855                 860

Pro Glu Gly Gln Pro Leu Gly Arg Arg Val Ala Ser Gly Pro Ser Pro
865                 870                 875                 880

Gly Glu Gly Ile Ser Pro Gln Ser Ala Gln Ala Pro Gln Ala Pro Gly
                885                 890                 895

Asp Asn His Val Val Pro Val Leu Arg
            900                 905
```

<210> SEQ ID NO 20
<211> LENGTH: 2718
<212> TYPE: DNA
<213> ORGANISM: Artificial Sequence
<220> FEATURE:

<223> OTHER INFORMATION: Description of Artificial Sequence: Synthetic polynucleotide

<400> SEQUENCE: 20

```
atggcaggct gcggttgtcc atgcggttgt ggcgccatgg caactgaaga gttcatcatc     60
cgcatccccc cataccacta tatccatgtg ctggaccaga acagcaacgt gtcccgtgtg    120
gaggtcgggc caaagaccta catccggcag gacaatgaga gggtactgtt tgcccccatg    180
cgcatggtga ccgtcccccc acgtcactac tgcacagtgg ccaaccctgt gtctcgggat    240
gcccagggct tggtgctgtt tgatgtcaca gggcaagttc ggcttcgcca cgctgacctc    300
gagatccggc tggcccagga ccccttcccc ctgtacccag gggaggtgct ggaaaaggac    360
atcacacccc tgcaggtggt tctgcccaac actgccctcc atctaaaggc gctgcttgat    420
tttgaggata aagatggaga caaggtggtg gcaggagatg agtggctttt cgagggacct    480
ggcacgtaca tcccccggaa ggaagtggag gtcgtggaga tcattcaggc caccatcatc    540
aggcagaacc aggctctgcg gctcagggcc cgcaaggagt gctgggaccg ggacggcaag    600
gagagggtga caggggaaga atggctggtc accacagtag ggcgtacctt cccagcggtg    660
tttgaggagg ttctggattt ggtggacgcc gtcatcctta cggaaaagac agccctgcac    720
ctccgggctc ggcggaactt ccgggacttc aggggagtgt cccgccgcac tggggaggag    780
tggctggtaa cagtgcagga cacagaggcc cacgtgccag atgtccacga ggaggtgctg    840
ggggttgtgc ccatcaccac cctgggcccc cacaactact gcgtgattct cgaccctgtc    900
ggaccggatg gcaagaatca gctggggcag aagcgcgtgg tcaagggaga gaagtctttt    960
ttcctccagc caggagagca gctggaacaa ggcatccagg atgtgtatgt gctgtcggag   1020
cagcaggggc tgctgctgag ggccctgcag cccctggagg agggggagga tgaggagaag   1080
gtctcacacc aggctgggga ccactggctc atccgcggac ccctggagta tgtgccatct   1140
gccaaagtgg aggtggtgga ggagcgccag gccatccctc tagacgagaa cgagggcatc   1200
tatgtgcagg atgtcaagac cggaaaggtg cgcgctgtga ttggaagcac ctacatgctg   1260
acccaggacg aagtcctgtg ggagaaagag ctgcctcccg ggtggaggga gctgctgaac   1320
aaggggcagg accctctggc agacaggggt gagaaggaca cagctaagag cctccagccc   1380
ttggcgcccc ggaacaagac ccgtgtggtc agctaccgcg tgccccacaa cgctgcggtg   1440
caggtgtacg actaccgaga gaagcgagcc cgcgtggtct tcgggcctga gctggtgtcg   1500
ctgggtcctg aggagcagtt cacagtgttg tccctctcag ctgggcggcc caagcgtccc   1560
catgcccgcc gtgcgctctg cctgctgctg gggcctgact tcttcacaga cgtcatcacc   1620
atcgaaacgg cggatcatgc caggctgcaa ctgcagctgg cctacaactg gcactttgag   1680
gtgaatgacc ggaaggaccc ccaagagacg gccaagctct tttcagtgcc agactttgta   1740
ggtgatgcct gcaaagccat cgcatcccgg gtgcgggggg ccgtggcctc tgtcactttc   1800
gatgacttcc ataagaactc agcccgcatc attcgcactg ctgtctttgg ctttgagacc   1860
tcggaagcga agggccccga tggcatggcc ctgcccaggc cccgggacca ggctgtcttc   1920
ccccaaaacg ggctggtggt cagcagtgtg gacgtgcagt cagtggagcc tgtggatcag   1980
aggacccggg acgccctgca acgcagcgtc cagctggcca tcgagatcac caccaactcc   2040
caggaagcgg cggccaagca tgaggctcag agactggagc aggaagcccg cggccggctt   2100
gagcggcaga agatcctgga ccagtcagaa gccgagaaag ctcgcaagga acttttggag   2160
ctggaggctc tgagcatggc cgtggagagc accgggactg ccaaggcgga ggccgagtcc   2220
cgtgcggagg cagcccggat tgagggagaa gggtccgtgc tgcaggccaa gctaaaagca   2280
```

```
caggccttgg ccattgaaac ggaggctgag ctccagaggg tccagaaggt ccgagagctg   2340

gaactggtct atgcccgggc ccagctggag ctggaggtga gcaaggctca gcagctggct   2400

gaggtggagg tgaagaagtt caagcagatg acagaggcca taggccccag caccatcagg   2460

gaccttgctg tggctgggcc tgagatgcag gtaaaactgc tccagtccct gggcctgaaa   2520

tcaaccctca tcaccgatgg ctccactccc atcaacctct tcaacacagc ctttgggctg   2580

ctggggatgg ggcccgaggg tcagcccctg ggcagaaggg tggccagtgg gcccagccct   2640

ggggagggga tatcccccca gtctgctcag gcccctcaag ctcctggaga caaccacgtg   2700

gtgcctgtac tgcgctaa                                                 2718
```

```
<210> SEQ ID NO 21
<211> LENGTH: 2627
<212> TYPE: PRT
<213> ORGANISM: Homo sapiens

<400> SEQUENCE: 21

Met Glu Lys Leu His Gly His Val Ser Ala His Pro Asp Ile Leu Ser
1               5                   10                  15

Leu Glu Asn Arg Cys Leu Ala Met Leu Pro Asp Leu Gln Pro Leu Glu
            20                  25                  30

Lys Leu His Gln His Val Ser Thr His Ser Asp Ile Leu Ser Leu Lys
        35                  40                  45

Asn Gln Cys Leu Ala Thr Leu Pro Asp Leu Lys Thr Met Glu Lys Pro
    50                  55                  60

His Gly Tyr Val Ser Ala His Pro Asp Ile Leu Ser Leu Glu Asn Gln
65                  70                  75                  80

Cys Leu Ala Thr Leu Ser Asp Leu Lys Thr Met Glu Lys Pro His Gly
                85                  90                  95

His Val Ser Ala His Pro Asp Ile Leu Ser Leu Glu Asn Arg Cys Leu
            100                 105                 110

Ala Thr Leu Pro Ser Leu Lys Ser Thr Val Ser Ala Ser Pro Leu Phe
        115                 120                 125

Gln Ser Leu Gln Ile Ser His Met Thr Gln Ala Asp Leu Tyr Arg Val
    130                 135                 140

Asn Asn Ser Asn Cys Leu Leu Ser Glu Pro Pro Ser Trp Arg Ala Gln
145                 150                 155                 160

His Phe Ser Lys Gly Leu Asp Leu Ser Thr Cys Pro Ile Ala Leu Lys
                165                 170                 175

Ser Ile Ser Ala Thr Glu Thr Ala Gln Glu Ala Thr Leu Gly Arg Trp
            180                 185                 190

Phe Asp Ser Glu Glu Lys Lys Gly Ala Glu Thr Gln Met Pro Ser Tyr
        195                 200                 205

Ser Leu Ser Leu Gly Glu Glu Glu Glu Val Glu Asp Leu Ala Val Lys
    210                 215                 220

Leu Thr Ser Gly Asp Ser Glu Ser His Pro Glu Pro Thr Asp His Val
225                 230                 235                 240

Leu Gln Glu Lys Lys Met Ala Leu Leu Ser Leu Leu Cys Ser Thr Leu
                245                 250                 255

Val Ser Glu Val Asn Met Asn Asn Thr Ser Asp Pro Thr Leu Ala Ala
            260                 265                 270

Ile Phe Glu Ile Cys Arg Glu Leu Ala Leu Leu Glu Pro Glu Phe Ile
        275                 280                 285

Leu Lys Ala Ser Leu Tyr Ala Arg Gln Gln Leu Asn Val Arg Asn Val
```

```
    290                 295                 300

Ala Asn Asn Ile Leu Ala Ile Ala Ala Phe Leu Pro Ala Cys Arg Pro
305                 310                 315                 320

His Leu Arg Arg Tyr Phe Cys Ala Ile Val Gln Leu Pro Ser Asp Trp
                325                 330                 335

Ile Gln Val Ala Glu Leu Tyr Gln Ser Leu Ala Glu Gly Asp Lys Asn
            340                 345                 350

Lys Leu Val Pro Leu Pro Ala Cys Leu Arg Thr Ala Met Thr Asp Lys
        355                 360                 365

Phe Ala Gln Phe Asp Glu Tyr Gln Leu Ala Lys Tyr Asn Pro Arg Lys
    370                 375                 380

His Arg Ala Lys Arg His Pro Arg Arg Pro Pro Arg Ser Pro Gly Met
385                 390                 395                 400

Glu Pro Pro Phe Ser His Arg Cys Phe Pro Arg Tyr Ile Gly Phe Leu
                405                 410                 415

Arg Glu Glu Gln Arg Lys Phe Glu Lys Ala Gly Asp Thr Val Ser Glu
            420                 425                 430

Lys Lys Asn Pro Pro Arg Phe Thr Leu Lys Lys Leu Val Gln Arg Leu
        435                 440                 445

His Ile His Lys Pro Ala Gln His Val Gln Ala Leu Leu Gly Tyr Arg
    450                 455                 460

Tyr Pro Ser Asn Leu Gln Leu Phe Ser Arg Ser Arg Leu Pro Gly Pro
465                 470                 475                 480

Trp Asp Ser Ser Arg Ala Gly Lys Arg Met Lys Leu Ser Arg Pro Glu
                485                 490                 495

Thr Trp Glu Arg Glu Leu Ser Leu Arg Gly Asn Lys Ala Ser Val Trp
            500                 505                 510

Glu Glu Leu Ile Glu Asn Gly Lys Leu Pro Phe Met Ala Met Leu Arg
        515                 520                 525

Asn Leu Cys Asn Leu Leu Arg Val Gly Ile Ser Ser Arg His His Glu
    530                 535                 540

Leu Ile Leu Gln Arg Leu Gln His Gly Lys Ser Val Ile His Ser Arg
545                 550                 555                 560

Gln Phe Pro Phe Arg Phe Leu Asn Ala His Asp Ala Ile Asp Ala Leu
                565                 570                 575

Glu Ala Gln Leu Arg Asn Gln Ala Leu Pro Phe Pro Ser Asn Ile Thr
            580                 585                 590

Leu Met Arg Arg Ile Leu Thr Arg Asn Glu Lys Asn Arg Pro Arg Arg
        595                 600                 605

Arg Phe Leu Cys His Leu Ser Arg Gln Gln Leu Arg Met Ala Met Arg
    610                 615                 620

Ile Pro Val Leu Tyr Glu Gln Leu Lys Arg Glu Lys Leu Arg Val His
625                 630                 635                 640

Lys Ala Arg Gln Trp Lys Tyr Asp Gly Glu Met Leu Asn Arg Tyr Arg
                645                 650                 655

Gln Ala Leu Glu Thr Ala Val Asn Leu Ser Val Lys His Ser Leu Pro
            660                 665                 670

Leu Leu Pro Gly Arg Thr Val Leu Val Tyr Leu Thr Asp Ala Asn Ala
        675                 680                 685

Asp Arg Leu Cys Pro Lys Ser Asn Pro Gln Gly Pro Pro Leu Asn Tyr
    690                 695                 700

Ala Leu Leu Leu Ile Gly Met Met Ile Thr Arg Ala Glu Gln Val Asp
705                 710                 715                 720
```

```
Val Val Leu Cys Gly Gly Asp Thr Leu Lys Thr Ala Val Leu Lys Ala
                725                 730                 735

Glu Glu Gly Ile Leu Lys Thr Ala Ile Lys Leu Gln Ala Gln Val Gln
            740                 745                 750

Glu Phe Asp Glu Asn Asp Gly Trp Ser Leu Asn Thr Phe Gly Lys Tyr
        755                 760                 765

Leu Leu Ser Leu Ala Gly Gln Arg Val Pro Val Asp Arg Val Ile Leu
    770                 775                 780

Leu Gly Gln Ser Met Asp Asp Gly Met Ile Asn Val Ala Lys Gln Leu
785                 790                 795                 800

Tyr Trp Gln Arg Val Asn Ser Lys Cys Leu Phe Val Gly Ile Leu Leu
                805                 810                 815

Arg Arg Val Gln Tyr Leu Ser Thr Asp Leu Asn Pro Asn Asp Val Thr
            820                 825                 830

Leu Ser Gly Cys Thr Asp Ala Ile Leu Lys Phe Ile Ala Glu His Gly
        835                 840                 845

Ala Ser His Leu Leu Glu His Val Gly Gln Met Asp Lys Ile Phe Lys
    850                 855                 860

Ile Pro Pro Pro Pro Gly Lys Thr Gly Val Gln Ser Leu Arg Pro Leu
865                 870                 875                 880

Glu Glu Asp Thr Pro Ser Pro Leu Ala Pro Val Ser Gln Gln Gly Trp
                885                 890                 895

Arg Ser Ile Arg Leu Phe Ile Ser Ser Thr Phe Arg Asp Met His Gly
            900                 905                 910

Glu Arg Asp Leu Leu Leu Arg Ser Val Leu Pro Ala Leu Gln Ala Arg
        915                 920                 925

Ala Ala Pro His Arg Ile Ser Leu His Gly Ile Asp Leu Arg Trp Gly
    930                 935                 940

Val Thr Glu Glu Glu Thr Arg Arg Asn Arg Gln Leu Glu Val Cys Leu
945                 950                 955                 960

Gly Glu Val Glu Asn Ala Gln Leu Phe Val Gly Ile Leu Gly Ser Arg
                965                 970                 975

Tyr Gly Tyr Ile Pro Pro Ser Tyr Asn Leu Pro Asp His Pro His Phe
            980                 985                 990

His Trp Ala Gln Gln Tyr Pro Ser  Gly Arg Ser Val Thr  Glu Met Glu
        995                 1000                1005

Val Met  Gln Phe Leu Asn Arg  Asn Gln Arg Leu Gln  Pro Ser Ala
    1010                 1015                 1020

Gln Ala  Leu Ile Tyr Phe Arg  Asp Ser Ser Phe Leu  Ser Ser Val
    1025                 1030                 1035

Pro Asp  Ala Trp Lys Ser Asp  Phe Val Ser Glu Ser  Glu Glu Ala
    1040                 1045                 1050

Ala Cys  Arg Ile Ser Glu Leu  Lys Ser Tyr Leu Ser  Arg Gln Lys
    1055                 1060                 1065

Gly Ile  Thr Cys Arg Arg Tyr  Pro Cys Glu Trp Gly  Gly Val Ala
    1070                 1075                 1080

Ala Gly  Arg Pro Tyr Val Gly  Gly Leu Glu Glu Phe  Gly Gln Leu
    1085                 1090                 1095

Val Leu  Gln Asp Val Trp Asn  Met Ile Gln Lys Leu  Tyr Leu Gln
    1100                 1105                 1110

Pro Gly  Ala Leu Leu Glu Gln  Pro Val Ser Ile Pro  Asp Asp Asp
    1115                 1120                 1125

Leu Val  Gln Ala Thr Phe Gln  Gln Leu Gln Lys Pro  Pro Ser Pro
    1130                 1135                 1140
```

```
Ala Arg  Pro Arg Leu Leu Gln  Asp Thr Val Gln Gln  Leu Met Leu
    1145                 1150                 1155

Pro His  Gly Arg Leu Ser Leu  Val Thr Gly Gln Ser  Gly Gln Gly
    1160                 1165                 1170

Lys Thr  Ala Phe Leu Ala Ser  Leu Val Ser Ala Leu  Gln Ala Pro
    1175                 1180                 1185

Asp Gly  Ala Lys Val Ala Pro  Leu Val Phe Phe His  Phe Ser Gly
    1190                 1195                 1200

Ala Arg  Pro Asp Gln Gly Leu  Ala Leu Thr Leu Leu  Arg Arg Leu
    1205                 1210                 1215

Cys Thr  Tyr Leu Arg Gly Gln  Leu Lys Glu Pro Gly  Ala Leu Pro
    1220                 1225                 1230

Ser Thr  Tyr Arg Ser Leu Val  Trp Glu Leu Gln Gln  Arg Leu Leu
    1235                 1240                 1245

Pro Lys  Ser Ala Glu Ser Leu  His Pro Gly Gln Thr  Gln Val Leu
    1250                 1255                 1260

Ile Ile  Asp Gly Ala Asp Arg  Leu Val Asp Gln Asn  Gly Gln Leu
    1265                 1270                 1275

Ile Ser  Asp Trp Ile Pro Lys  Lys Leu Pro Arg Cys  Val His Leu
    1280                 1285                 1290

Val Leu  Ser Val Ser Ser Asp  Ala Gly Leu Gly Glu  Thr Leu Glu
    1295                 1300                 1305

Gln Ser  Gln Gly Ala His Val  Leu Ala Leu Gly Pro  Leu Glu Ala
    1310                 1315                 1320

Ser Ala  Arg Ala Arg Leu Val  Arg Glu Glu Leu Ala  Leu Tyr Gly
    1325                 1330                 1335

Lys Arg  Leu Glu Glu Ser Pro  Phe Asn Asn Gln Met  Arg Leu Leu
    1340                 1345                 1350

Leu Val  Lys Arg Glu Ser Gly  Arg Pro Leu Tyr Leu  Arg Leu Val
    1355                 1360                 1365

Thr Asp  His Leu Arg Leu Phe  Thr Leu Tyr Glu Gln  Val Ser Glu
    1370                 1375                 1380

Arg Leu  Arg Thr Leu Pro Ala  Thr Val Pro Leu Leu  Leu Gln His
    1385                 1390                 1395

Ile Leu  Ser Thr Leu Glu Lys  Glu His Gly Pro Asp  Val Leu Pro
    1400                 1405                 1410

Gln Ala  Leu Thr Ala Leu Glu  Val Thr Arg Ser Gly  Leu Thr Val
    1415                 1420                 1425

Asp Gln  Leu His Gly Val Leu  Ser Val Trp Arg Thr  Leu Pro Lys
    1430                 1435                 1440

Gly Thr  Lys Ser Trp Glu Glu  Ala Val Ala Ala Gly  Asn Ser Gly
    1445                 1450                 1455

Asp Pro  Tyr Pro Met Gly Pro  Phe Ala Cys Leu Val  Gln Ser Leu
    1460                 1465                 1470

Arg Ser  Leu Leu Gly Glu Gly  Pro Leu Glu Arg Pro  Gly Ala Arg
    1475                 1480                 1485

Leu Cys  Leu Pro Asp Gly Pro  Leu Arg Thr Ala Ala  Lys Arg Cys
    1490                 1495                 1500

Tyr Gly  Lys Arg Pro Gly Leu  Glu Asp Thr Ala His  Ile Leu Ile
    1505                 1510                 1515

Ala Ala  Gln Leu Trp Lys Thr  Cys Asp Ala Asp Ala  Ser Gly Thr
    1520                 1525                 1530

Phe Arg  Ser Cys Pro Pro Glu  Ala Leu Gly Asp Leu  Pro Tyr His
```

```
    1535                1540                1545

Leu Leu Gln Ser Gly Asn Arg Gly Leu Leu Ser Lys Phe Leu Thr
    1550                1555                1560

Asn Leu His Val Val Ala Ala His Leu Glu Leu Gly Leu Val Ser
    1565                1570                1575

Arg Leu Leu Glu Ala His Ala Leu Tyr Ala Ser Ser Val Pro Lys
    1580                1585                1590

Glu Glu Gln Lys Leu Pro Glu Ala Asp Val Ala Val Phe Arg Thr
    1595                1600                1605

Phe Leu Arg Gln Gln Ala Ser Ile Leu Ser Gln Tyr Pro Arg Leu
    1610                1615                1620

Leu Pro Gln Gln Ala Ala Asn Gln Pro Leu Asp Ser Pro Leu Cys
    1625                1630                1635

His Gln Ala Ser Leu Leu Ser Arg Arg Trp His Leu Gln His Thr
    1640                1645                1650

Leu Arg Trp Leu Asn Lys Pro Arg Thr Met Lys Asn Gln Gln Ser
    1655                1660                1665

Ser Ser Leu Ser Leu Ala Val Ser Ser Ser Pro Thr Ala Val Ala
    1670                1675                1680

Phe Ser Thr Asn Gly Gln Arg Ala Ala Val Gly Thr Ala Asn Gly
    1685                1690                1695

Thr Val Tyr Leu Leu Asp Leu Arg Thr Trp Gln Glu Glu Lys Ser
    1700                1705                1710

Val Val Ser Gly Cys Asp Gly Ile Ser Ala Cys Leu Phe Leu Ser
    1715                1720                1725

Asp Asp Thr Leu Phe Leu Thr Ala Phe Asp Gly Leu Leu Glu Leu
    1730                1735                1740

Trp Asp Leu Gln His Gly Cys Arg Val Leu Gln Thr Lys Ala His
    1745                1750                1755

Gln Tyr Gln Ile Thr Gly Cys Cys Leu Ser Pro Asp Cys Arg Leu
    1760                1765                1770

Leu Ala Thr Val Cys Leu Gly Gly Cys Leu Lys Leu Trp Asp Thr
    1775                1780                1785

Val Arg Gly Gln Leu Ala Phe Gln His Thr Tyr Pro Lys Ser Leu
    1790                1795                1800

Asn Cys Val Ala Phe His Pro Glu Gly Gln Val Ile Ala Thr Gly
    1805                1810                1815

Ser Trp Ala Gly Ser Ile Ser Phe Phe Gln Val Asp Gly Leu Lys
    1820                1825                1830

Val Thr Lys Asp Leu Gly Ala Pro Gly Ala Ser Ile Arg Thr Leu
    1835                1840                1845

Ala Phe Asn Val Pro Gly Gly Val Val Ala Val Gly Arg Leu Asp
    1850                1855                1860

Ser Met Val Glu Leu Trp Ala Trp Arg Glu Gly Ala Arg Leu Ala
    1865                1870                1875

Ala Phe Pro Ala His His Gly Phe Val Ala Ala Ala Leu Phe Leu
    1880                1885                1890

His Ala Gly Cys Gln Leu Leu Thr Ala Gly Glu Asp Gly Lys Val
    1895                1900                1905

Gln Val Trp Ser Gly Ser Leu Gly Arg Pro Arg Gly His Leu Gly
    1910                1915                1920

Ser Leu Ser Leu Ser Pro Ala Leu Ser Val Ala Leu Ser Pro Asp
    1925                1930                1935
```

```
Gly Asp  Arg Val Ala Val Gly  Tyr Arg Ala Asp Gly  Ile Arg Ile
    1940                 1945                 1950

Tyr Lys  Ile Ser Ser Gly Ser  Gln Gly Ala Gln Gly  Gln Ala Leu
    1955                 1960                 1965

Asp Val  Ala Val Ser Ala Leu  Ala Trp Leu Ser Pro  Lys Val Leu
    1970                 1975                 1980

Val Ser  Gly Ala Glu Asp Gly  Ser Leu Gln Gly Trp  Ala Leu Lys
    1985                 1990                 1995

Glu Cys  Ser Leu Gln Ser Leu  Trp Leu Leu Ser Arg  Phe Gln Lys
    2000                 2005                 2010

Pro Val  Leu Gly Leu Ala Thr  Ser Gln Glu Leu Leu  Ala Ser Ala
    2015                 2020                 2025

Ser Glu  Asp Phe Thr Val Gln  Leu Trp Pro Arg Gln  Leu Leu Thr
    2030                 2035                 2040

Arg Pro  His Lys Ala Glu Asp  Phe Pro Cys Gly Thr  Glu Leu Arg
    2045                 2050                 2055

Gly His  Glu Gly Pro Val Ser  Cys Cys Ser Phe Ser  Thr Asp Gly
    2060                 2065                 2070

Gly Ser  Leu Ala Thr Gly Gly  Arg Asp Arg Ser Leu  Leu Cys Trp
    2075                 2080                 2085

Asp Val  Arg Thr Pro Lys Thr  Pro Val Leu Ile His  Ser Phe Pro
    2090                 2095                 2100

Ala Cys  His Arg Asp Trp Val  Thr Gly Cys Ala Trp  Thr Lys Asp
    2105                 2110                 2115

Asn Leu  Leu Ile Ser Cys Ser  Ser Asp Gly Ser Val  Gly Leu Trp
    2120                 2125                 2130

Asp Pro  Glu Ser Gly Gln Arg  Leu Gly Gln Phe Leu  Gly His Gln
    2135                 2140                 2145

Ser Ala  Val Ser Ala Val Ala  Ala Val Glu Glu His  Val Val Ser
    2150                 2155                 2160

Val Ser  Arg Asp Gly Thr Leu  Lys Val Trp Asp His  Gln Gly Val
    2165                 2170                 2175

Glu Leu  Thr Ser Ile Pro Ala  His Ser Gly Pro Ile  Ser His Cys
    2180                 2185                 2190

Ala Ala  Ala Met Glu Pro Arg  Ala Ala Gly Gln Pro  Gly Ser Glu
    2195                 2200                 2205

Leu Leu  Val Val Thr Val Gly  Leu Asp Gly Ala Thr  Arg Leu Trp
    2210                 2215                 2220

His Pro  Leu Leu Val Cys Gln  Thr His Thr Leu Leu  Gly His Ser
    2225                 2230                 2235

Gly Pro  Val Arg Ala Ala Ala  Val Ser Glu Thr Ser  Gly Leu Met
    2240                 2245                 2250

Leu Thr  Ala Ser Glu Asp Gly  Ser Val Arg Leu Trp  Gln Val Pro
    2255                 2260                 2265

Lys Glu  Ala Asp Asp Thr Cys  Ile Pro Arg Ser Ser  Ala Ala Val
    2270                 2275                 2280

Thr Ala  Val Ala Trp Ala Pro  Asp Gly Ser Met Ala  Val Ser Gly
    2285                 2290                 2295

Asn Gln  Ala Gly Glu Leu Ile  Leu Trp Gln Glu Ala  Lys Ala Val
    2300                 2305                 2310

Ala Thr  Ala Gln Ala Pro Gly  His Ile Gly Ala Leu  Ile Trp Ser
    2315                 2320                 2325

Ser Ala  His Thr Phe Phe Val  Leu Ser Ala Asp Glu  Lys Ile Ser
    2330                 2335                 2340
```

```
Glu Trp  Gln Val Lys Leu Arg  Lys Gly Ser Ala Pro  Gly Asn Leu
    2345                 2350                 2355

Ser Leu  His Leu Asn Arg Ile  Leu Gln Glu Asp Leu  Gly Val Leu
    2360                 2365                 2370

Thr Ser  Leu Asp Trp Ala Pro  Asp Gly His Phe Leu  Ile Leu Ala
    2375                 2380                 2385

Lys Ala  Asp Leu Lys Leu Leu  Cys Met Lys Pro Gly  Asp Ala Pro
    2390                 2395                 2400

Ser Glu  Ile Trp Ser Ser Tyr  Thr Glu Asn Pro Met  Ile Leu Ser
    2405                 2410                 2415

Thr His  Lys Glu Tyr Gly Ile  Phe Val Leu Gln Pro  Lys Asp Pro
    2420                 2425                 2430

Gly Val  Leu Ser Phe Leu Arg  Gln Lys Glu Ser Gly  Glu Phe Glu
    2435                 2440                 2445

Glu Arg  Leu Asn Phe Asp Ile  Asn Leu Glu Asn Pro  Ser Arg Thr
    2450                 2455                 2460

Leu Ile  Ser Ile Thr Gln Ala  Lys Pro Glu Ser Glu  Ser Ser Phe
    2465                 2470                 2475

Leu Cys  Ala Ser Ser Asp Gly  Ile Leu Trp Asn Leu  Ala Lys Cys
    2480                 2485                 2490

Ser Pro  Glu Gly Glu Trp Thr  Thr Gly Asn Met Trp  Gln Lys Lys
    2495                 2500                 2505

Ala Asn  Thr Pro Glu Thr Gln  Thr Pro Gly Thr Asp  Pro Ser Thr
    2510                 2515                 2520

Cys Arg  Glu Ser Asp Ala Ser  Met Asp Ser Asp Ala  Ser Met Asp
    2525                 2530                 2535

Ser Glu  Pro Thr Pro His Leu  Lys Thr Arg Gln Arg  Arg Lys Ile
    2540                 2545                 2550

His Ser  Gly Ser Val Thr Ala  Leu His Val Leu Pro  Glu Leu Leu
    2555                 2560                 2565

Val Thr  Ala Ser Lys Asp Arg  Asp Val Lys Leu Trp  Glu Arg Pro
    2570                 2575                 2580

Ser Met  Gln Leu Leu Gly Leu  Phe Arg Cys Glu Gly  Ser Val Ser
    2585                 2590                 2595

Cys Leu  Glu Pro Trp Leu Gly  Ala Asn Ser Thr Leu  Gln Leu Ala
    2600                 2605                 2610

Val Gly  Asp Val Gln Gly Asn  Val Tyr Phe Leu Asn  Trp Glu
    2615                 2620                 2625
```

<210> SEQ ID NO 22
<211> LENGTH: 7884
<212> TYPE: DNA
<213> ORGANISM: Homo sapiens

<400> SEQUENCE: 22

```
atggaaaaac tccatgggca tgtgtctgcc catccagaca tcctctcctt ggagaaccgg     60

tgcctggcta tgctccctga cttacagccc ttggagaaac tacatcagca tgtatctacc    120

cactcagata tcctctcctt gaagaaccag tgcctagcca cgcttcctga cctgaagacc    180

atggaaaaac cacatggata tgtgtctgcc cacccagaca tcctctcctt ggagaaccag    240

tgcctggcca cactttctga cctgaagacc atggagaaac cacatggaca tgtttctgcc    300

cacccagaca tcctctcctt ggagaaccgg tgcctggcca ccctccctag tctaaagagc    360

actgtgtctg ccagcccctt gttccagagt ctacagatat ctcacatgac gcaagctgat    420
```

```
ttgtaccgtg tgaacaacag caattgcctg ctctctgagc ctccaagttg gagggctcag    480
catttctcta agggactaga cctttcaacc tgccctatag ccctgaaatc catctctgcc    540
acagagacag ctcaggaagc aactttgggt cgttggtttg attcagaaga gaagaaaggg    600
gcagagaccc aaatgccttc ttatagtctg agcttgggag aggaggagga ggtggaggat    660
ctggccgtga agctcacctc tggagactct gaatctcatc cagagcctac tgaccatgtc    720
cttcaggaaa agaagatggc tctactgagc ttgctgtgct ctactctggt ctcagaagta    780
aacatgaaca atacatctga ccccaccctg gctgccattt ttgaaatctg tcgtgaactt    840
gccctcctgg agcctgagtt tatcctcaag gcatctttgt atgccaggca gcagctgaac    900
gtccggaatg tggccaataa catcttggcc attgctgctt tcttgccggc gtgtcgcccc    960
cacctgcgac gatatttctg tgccattgtc cagctgcctt ctgactggat ccaggtggct   1020
gagctttacc agagcctggc tgagggagat aagaataagc tggtgcccct gcccgcctgt   1080
ctccgtactg ccatgacgga caaatttgcc cagtttgacg agtaccagct ggctaagtac   1140
aaccctcgga agcaccgggc caagagacac ccccgccggc cacccccgctc tccagggatg   1200
gagcctccat tttctcacag atgttttcca aggtacatag ggtttctcag agaagagcag   1260
agaaagtttg agaaggccgg tgatacagtg tcagagaaaa agaatcctcc aaggttcacc   1320
ctgaagaagc tggttcagcg actgcacatc cacaagcctg cccagcacgt tcaagccctg   1380
ctgggttaca gatacccctc caacctacag ctcttttctc gaagtcgcct tcctgggcct   1440
tgggattcta gcagagctgg gaagaggatg aagctgtcta ggccagagac ctgggagcgg   1500
gagctgagcc tacgggggaa caaagcgtcg gtctgggagg aactcattga aaatgggaag   1560
cttcccttca tggccatgct tcggaacctg tgcaacctgc tgcgggttgg aatcagttcc   1620
cgccaccatg agctcattct ccagagactc cagcatggga agtcggtgat ccacagtcgg   1680
cagtttccat tcagatttct taacgcccat gatgccattg atgccctcga ggctcaactc   1740
agaaatcaag cattgccctt tccttcgaat ataacactga tgaggcggat actaactaga   1800
aatgaaaaga accgtcccag gcggaggttt ctttgccacc taagccgtca gcagcttcgt   1860
atggcaatga ggatacctgt gttgtatgag cagctcaaga gggagaagct gagagtacac   1920
aaggccagac agtggaaata tgatggtgag atgctgaaca ggtaccgaca ggccctagag   1980
acagctgtga acctctctgt gaagcacagc ctgcccctgc tgccaggccg cactgtcttg   2040
gtctatctga cagatgctaa tgcagacagg ctctgtccaa agagcaaccc acaagggccc   2100
ccgctgaact atgcactgct gttgattggg atgatgatca cgagggcgga gcaggtggac   2160
gtcgtgctgt gtggaggtga cactctgaag actgcagtgc ttaaggcaga agaaggcatc   2220
ctgaagactg ccatcaagct ccaggctcaa gtccaggagt ttgatgaaaa tgatggatgg   2280
tccctgaata cttttgggaa atacctgctg tctctggctg gccaaagggt tcctgtggac   2340
agggtcatcc tccttggcca aagcatggat gatggaatga taaatgtggc caaacagctt   2400
tactggcagc gtgtgaattc caagtgcctc tttgttggta tcctcctaag aagggtacaa   2460
tacctgtcaa cagatttgaa tcccaatgat gtgacactct caggctgtac tgatgcgata   2520
ctgaagttca ttgcagagca tggggcctcc catcttctgg aacatgtggg ccaaatggac   2580
aaaatattca agattccacc acccccagga aagacagggg tccagtctct ccggccactg   2640
gaagaggaca ctccaagccc cttggctcct gtttcccagc aaggatggcg cagcatccgg   2700
cttttcattt catccacttt ccgagacatg cacggggagc gggacctgct gctgaggtct   2760
gtgctgccag cactgcaggc ccgagcggcc cctcaccgta tcagccttca cggaatcgac   2820
```

```
ctccgctggg gcgtcactga ggaggagacc cgtaggaaca gacaactgga agtgtgcctt   2880
ggggaggtgg agaacgcaca gctgtttgtg ggattctgg gctcccgtta tggatacatt    2940
ccccccagct acaaccttcc tgaccatcca cacttccact gggcccagca gtacccttca   3000
gggcgctctg tgacagagat ggaggtgatg cagttcctga accggaacca acgtctgcag   3060
ccctctgccc aagctctcat ctacttccgg gattccagct tcctcagctc tgtgccagat   3120
gcctggaaat ctgactttgt ttctgagtct gaagaggccg catgtcggat ctcagaactg   3180
aagagctacc taagcagaca gaaagggata acctgccgca gatacccctg tgagtggggg   3240
ggtgtggcag ctggccggcc ctatgttggc gggctggagg agtttgggca gttggttctg   3300
caggatgtat ggaatatgat ccagaagctc tacctgcagc ctggggccct gctggagcag   3360
ccagtgtcca tcccagacga tgacttggtc caggccacct tccagcagct gcagaagcca   3420
ccgagtcctg cccggccacg ccttcttcag gacacagtgc aacagctgat gctgccccac   3480
ggaaggctga gcctggtgac ggggcagtca ggacagggca agacagcctt cctggcatct   3540
cttgtgtcag ccctgcaggc tcctgatggg gccaaggtgg caccattagt cttcttccac   3600
ttttctgggg ctcgtcctga ccagggtctt gccctcactc tgctcagacg cctctgtacc   3660
tatctgcgtg gccaactaaa agagccaggt gccctcccca gcacctaccg aagcctggtg   3720
tgggagctgc agcagaggct gctgcccaag tctgctgagt ccctgcatcc tggccagacc   3780
caggtcctga tcatcgatgg ggctgatagg ttagtggacc agaatgggca gctgatttca   3840
gactggatcc caaagaagct tccccggtgt gtacacctgg tgctgagtgt gtctagtgat   3900
gcaggcctag gggagaccct tgagcagagc cagggtgccc acgtgctggc cttggggcct   3960
ctggaggcct ctgctcgggc ccggctggtg agagaggagc tggccctgta cgggaagcgg   4020
ctggaggagt caccatttaa caaccagatg cgactgctgc tggtgaagcg ggaatcaggc   4080
cggccgctct acctgcgctt ggtcaccgat cacctgaggc tcttcacgct gtatgagcag   4140
gtgtctgaga gactccggac cctgcctgcc actgtccccc tgctgctgca gcacatcctg   4200
agcacactgg agaaggagca cgggcctgat gtccttcccc aggccttgac tgccctagaa   4260
gtcacacgga gtggtttgac tgtggaccag ctgcacggag tgctgagtgt gtggcggaca   4320
ctaccgaagg ggactaagag ctgggaagaa gcagtggctg ctggtaacag tggagacccc   4380
taccccatgg gcccgtttgc ctgcctcgtc cagagtctgc gcagtttgct aggggagggc   4440
cctctggagc gccctggtgc ccggctgtgc ctccctgatg ggcccctgag aacagcagct   4500
aaacgttgct atgggaagag gccagggcta gaggacacgg cacacatcct cattgcagct   4560
cagctctgga agacatgtga cgctgatgcc tcaggcacct tccgaagttg ccctcctgag   4620
gctctgggag acctgcctta ccacctgctc cagagcggga accgtggact tctttcgaag   4680
ttccttacca acctccatgt ggtggctgca cacttggaat tgggtctggt ctctcggctc   4740
ttggaggccc atgccctcta tgcttcttca gtccccaaag aggaacaaaa gctccccgag   4800
gctgacgttg cagtgtttcg caccttcctg aggcagcagg cttcaatcct cagccagtac   4860
ccccggctcc tgccccagca ggcagccaac cagcccctgg actcacctct ttgccaccaa   4920
gcctcgctgc tctcccggag atggcacctc caacacacac tacgatggct taataaaccc   4980
cggaccatga aaaatcagca aagctccagc ctgtctctgg cagtttcctc atcccctact   5040
gctgtggcct tctccaccaa tgggcaaaga gcagctgtgg gcactgccaa tgggacagtt   5100
tacctgttgg acctgagaac ttggcaggag gagaagtctg tggtgagtgg ctgtgatgga   5160
atctctgctt gtttgttcct ctccgatgat acactctttc ttactgcctt cgacgggctc   5220
```

```
ctggagctct gggacctgca gcatggttgt cgggtgctgc agactaaggc tcaccagtac   5280
caaatcactg gctgctgcct gagcccagac tgccggctgc tagccaccgt gtgcttggga   5340
ggatgcctaa agctgtggga cacagtccgt gggcagctgg ccttccagca cacctacccc   5400
aagtccctga actgtgttgc cttccaccca gaggggcagg taatagccac aggcagctgg   5460
gctggcagca tcagcttctt ccaggtggat gggctcaaag tcaccaagga cctgggggca   5520
cccggagcct ctatccgtac cttggccttc aatgtgcctg ggggggttgt ggctgtgggc   5580
cggctggaca gtatggtgga gctgtgggcc tggcgagaag ggcacggct ggctgccttc   5640
cctgcccacc atggctttgt tgctgctgcg cttttcctgc atgcgggttg ccagttactg   5700
acggctggag aggatggcaa ggttcaggtg tggtcagggt ctctgggtcg gccccgtggg   5760
cacctgggtt ccctttctct ctctcctgcc ctctctgtgg cactcagccc agatggtgat   5820
cgggtggctg ttggatatcg agcggatggc attaggatct acaaaatctc ttcaggttcc   5880
cagggggctc agggtcaggc actggatgtg gcagtgtccg ccctggcctg gctaagcccc   5940
aaggtattgg tgagtggtgc agaagatggg tccttgcagg gctgggcact caaggaatgc   6000
tcccttcagt ccctctggct cctgtccaga ttccagaagc ctgtgctagg actggccact   6060
tcccaggagc tcttggcttc tgcctcagag gatttcacag tgcagctgtg gccaaggcag   6120
ctgctgacgc ggccacacaa ggcagaagac tttccctgtg gcactgagct gcggggacat   6180
gagggccctg tgagctgctg tagtttcagc actgatggag gcagcctggc caccgggggc   6240
cgggatcgga gtctcctctg ctgggacgtg aggacaccca aaacccctgt tttgatccac   6300
tccttccctg cctgtcaccg tgactgggtc actggctgtg cctggaccaa agataaccta   6360
ctgatatcct gctccagtga tggctctgtg gggctctggg acccagagtc aggacagcgg   6420
cttggtcagt tcctgggtca tcagagtgct gtgagcgctg tggcagctgt ggaggagcac   6480
gtggtgtctg tgagccggga tgggaccttg aaagtgtggg accatcaagg cgtggagctg   6540
accagcatcc ctgctcactc aggacccatt agccactgtg cagctgccat ggagccccgt   6600
gcagctggac agcctgggtc agagcttctg gtggtaaccg tcgggctaga tggggccaca   6660
cggttatggc atccactctt ggtgtgccaa acccacaccc tcctgggaca cagcggccca   6720
gtccgtgctg ctgctgtttc agaaacctca ggcctcatgc tgaccgcctc tgaggatggt   6780
tctgtacggc tctggcaggt tcctaaggaa gcagatgaca catgtatacc aaggagttct   6840
gcagccgtca ctgctgtggc ttgggcacca gatggttcca tggcagtatc tggaaatcaa   6900
gctggggaac taatcttgtg gcaggaagct aaggctgtgg ccacagcaca ggctccaggc   6960
cacattggtg ctctgatctg gtcctcggca cacacctttt ttgtcctcag tgctgatgag   7020
aaaatcagcg agtggcaagt gaaactgcgg aagggttcgg cacccggaaa tttgagtctt   7080
cacctgaacc gaattctaca ggaggactta ggggtgctga caagtctgga ttgggctcct   7140
gatggtcact ttctcatctt ggccaaagca gatttgaagt tactttgcat gaagccaggg   7200
gatgctccat ctgaaatctg gagcagctat acagaaaatc ctatgatatt gtccacccac   7260
aaggagtatg gcatatttgt cctgcagccc aaggatcctg gagttctttc tttcttgagg   7320
caaaaggaat caggagagtt tgaagagagg ctgaactttg atataaactt agagaatcct   7380
agtaggaccc taatatcgat aactcaagcc aaacctgaat ctgagtcctc atttttgtgt   7440
gccagctctg atgggatcct atggaacctg gccaaatgca gcccagaagg agaatggacc   7500
acaggtaaca tgtggcagaa aaaagcaaac actccagaaa cccaaactcc agggacagac   7560
ccatctacct gcagggaatc tgatgccagc atggatagtg atgccagcat ggatagtgag   7620
```

```
ccaacaccac atctaaagac acggcagcgt agaaagattc actcgggctc tgtcacagcc   7680

ctccatgtgc tacctgagtt gctggtgaca gcttcgaagg acagagatgt taagctatgg   7740

gagagaccca gtatgcagct gctgggcctg ttccgatgcg aagggtcagt gagctgcctg   7800

gaaccttggc tgggcgctaa ctccaccctg cagcttgccg tgggagacgt gcagggcaat   7860

gtgtactttc tgaattggga atga                                           7884


<210> SEQ ID NO 23
<211> LENGTH: 98
<212> TYPE: RNA
<213> ORGANISM: Homo sapiens

<400> SEQUENCE: 23

ggcuggcuuu agcucagcgg uuacuucgac aguucuuuaa uugaaacaag caaccugucu     60

ggguuguucg agacccgcgg gcgcucucca guccuuuu                             98


<210> SEQ ID NO 24
<211> LENGTH: 88
<212> TYPE: RNA
<213> ORGANISM: Homo sapiens

<400> SEQUENCE: 24

ggcuggcuuu agcucagcgg uuacuucgag uacauuguaa ccaccucucu gggugguucg     60

agacccgcgg gugcuuucca gcucuuuu                                        88


<210> SEQ ID NO 25
<211> LENGTH: 88
<212> TYPE: RNA
<213> ORGANISM: Homo sapiens

<400> SEQUENCE: 25

ggcuggcuuu agcucagcgg uuacuucgcg ugucaucaaa ccaccucucu ggguuguucg     60

agacccgcgg gcgcucucca gcccucuu                                        88


<210> SEQ ID NO 26
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

atggtgagca agggcgagga ggataacatg gccatcatca aggagttcat gcgcttcaag     60

gtgcacatgg agggctccgt gaacggccac gagttcgaga tcgagggcga gggcgagggc    120

cgcccctacg agggcaccca gaccgccaag ctgaaggtga ccaagggtgg ccccctgccc    180

ttcgcctggg acatcctgtc ccctcagttc atgtacggct ccaaggccta cgtgaagcac    240

cccgccgaca tccccgacta cttgaagctg tccttccccg agggcttcaa gtgggagcgc    300

gtgatgaact tcgaggacgg cggcgtggtg accgtgaccc aggactcctc cctgcaggac    360

ggcgagttca tctacaaggt gaagctgcgc ggcaccaact tcccctccga cggccccgta    420

atgcagaaga agaccatggg ctgggaggcc tcctccgagc ggatgtaccc cgaggacggc    480

gccctgaagg gcgagatcaa gcagaggctg aagctgaagg acggcggcca ctacgacgct    540

gaggtcaaga ccacctacaa ggccaagaag cccgtgcagc tgcccggcgc ctacaacgtc    600

aacatcaagt tggacatcac ctcccacaac gaggactaca ccatcgtgga acagtacgaa    660

cgcgccgagg gccgccactc caccggcggc atggacgagc tgtacaagta a             711
```

<210> SEQ ID NO 27
<211> LENGTH: 237
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (237)..(237)
<223> OTHER INFORMATION: Any amino acid

<400> SEQUENCE: 27

```
Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys Xaa
225                 230                 235
```

<210> SEQ ID NO 28
<211> LENGTH: 1200
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28

```
atggtgagca agggcgagga ggataacatg gccatcatca aggagttcat gcgcttcaag     60

gtgcacatgg agggctccgt gaacggccac gagttcgaga tcgagggcga gggcgagggc    120

cgcccctacg agggcaccca gaccgccaag ctgaaggtga ccaagggtgg cccccctgccc    180

ttcgcctggg acatcctgtc ccctcagttc atgtacggct ccaaggccta cgtgaagcac    240
```

```
cccgccgaca tccccgacta cttgaagctg tccttccccg agggcttcaa gtgggagcgc    300

gtgatgaact tcgaggacgg cggcgtggtg accgtgaccc aggactcctc cctgcaggac    360

ggcgagttca tctacaaggt gaagctgcgc ggcaccaact tcccctccga cggccccgta    420

atgcagaaga agaccatggg ctgggaggcc tcctccgagc ggatgtaccc cgaggacggc    480

gccctgaagg gcgagatcaa gcagaggctg aagctgaagg acggcggcca ctacgacgct    540

gaggtcaaga ccacctacaa ggccaagaag cccgtgcagc tgcccggcgc ctacaacgtc    600

aacatcaagt tggacatcac ctcccacaac gaggactaca ccatcgtgga acagtacgaa    660

cgcgccgagg gccgccactc caccggcggc atggacgagc tgtacaagta atgcacacaa    720

cactggcagg atgctgtgcc ttggacagaa ctcctcagtc tacagacaga ggatggcttc    780

tggaaactta caccagaact gggacttata ttaaatctta atacaaatgg tttgcacagc    840

tttcttaaac aaaaaggcat tcaatctcta ggtgtaaaag gaagagaatg tctcctggac    900

ctaattgcca caatgctggt actacagttt attcgcacca ggttggaaaa agagggaata    960

gtgttcaaat cactgatgaa aatggatgac ccttctattt ccaggaatat tccctgggct   1020

tttgaggcaa taaagcaagc aagtgaatgg gtaagaagaa ctgaaggaca gtacccatct   1080

atctgcccac ggcttgaact ggggaacgac tgggactctg ccaccaagca gttgctggga   1140

ctccagccca taagcactgt gtcccctctt catagagtcc tccattacag tcaaggctaa   1200
```

```
<210> SEQ ID NO 29
<211> LENGTH: 399
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (237)..(237)
<223> OTHER INFORMATION: Any amino acid

<400> SEQUENCE: 29

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175
```

```
His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys Xaa Cys Thr Gln
225                 230                 235                 240

His Trp Gln Asp Ala Val Pro Trp Thr Glu Leu Leu Ser Leu Gln Thr
            245                 250                 255

Glu Asp Gly Phe Trp Lys Leu Thr Pro Glu Leu Gly Leu Ile Leu Asn
            260                 265                 270

Leu Asn Thr Asn Gly Leu His Ser Phe Leu Lys Gln Lys Gly Ile Gln
        275                 280                 285

Ser Leu Gly Val Lys Gly Arg Glu Cys Leu Leu Asp Leu Ile Ala Thr
    290                 295                 300

Met Leu Val Leu Gln Phe Ile Arg Thr Arg Leu Glu Lys Glu Gly Ile
305                 310                 315                 320

Val Phe Lys Ser Leu Met Lys Met Asp Asp Pro Ser Ile Ser Arg Asn
            325                 330                 335

Ile Pro Trp Ala Phe Glu Ala Ile Lys Gln Ala Ser Glu Trp Val Arg
            340                 345                 350

Arg Thr Glu Gly Gln Tyr Pro Ser Ile Cys Pro Arg Leu Glu Leu Gly
        355                 360                 365

Asn Asp Trp Asp Ser Ala Thr Lys Gln Leu Leu Gly Leu Gln Pro Ile
    370                 375                 380

Ser Thr Val Ser Pro Leu His Arg Val Leu His Tyr Ser Gln Gly
385                 390                 395
```

```
<210> SEQ ID NO 30
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30

cgggatccgc cttcagctgg ggctcgctct ggagc                               35


<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31

cgggaattct tacagaccca cgatgctgtt cag                                 33


<210> SEQ ID NO 32
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

cgggatccgc cttcagctgg ggctcgctct ggagc                               35
```

<210> SEQ ID NO 33
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
cgggaattct tactctcggg agggcgggga tc 32

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
aaaggatcct atggcagcaa ggc 23

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
aaagaattct tacagaccca cgatgctgtt 30

<210> SEQ ID NO 36
<211> LENGTH: 80
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
cgggatccgc cttcagctgg ggctcgctgt ggagcggcat taaaaatttc ggttccaccg 60
ttaagaacta tgaattccgg 80

<210> SEQ ID NO 37
<211> LENGTH: 80
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
ccggaattca tagttcttaa cggtggaacc gaaattttta atgccgctcc acagcgagcc 60
ccagctgaag gcggatcccg 80

<210> SEQ ID NO 38
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
cgggattcgg cggcgaattc gatttacgat atcccaacga ccgaa 45

<210> SEQ ID NO 39
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
cccctcgagt tagccttgac tgtaatggag gactctatg 39

<210> SEQ ID NO 40
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
ctctgctagc caccatggcc ttcagctggg gctcg 35

<210> SEQ ID NO 41
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
ggggccatgg cgctgccgcg cggcaccagg ccgttcttaa cggtggaacc g 51

<210> SEQ ID NO 42
<211> LENGTH: 252
<212> TYPE: PRT
<213> ORGANISM: Homo sapiens

<400> SEQUENCE: 42

```
Ala Asn Leu Arg Leu Pro Met Ala Ser Ala Leu Pro Glu Ala Leu Cys
1               5                   10                  15

Ser Gln Ser Arg Thr Thr Pro Val Asp Leu Cys Leu Leu Glu Glu Ser
            20                  25                  30

Val Gly Ser Leu Glu Gly Ser Arg Cys Pro Val Phe Ala Phe Gln Ser
        35                  40                  45

Ser Asp Thr Glu Ser Asp Glu Leu Ser Glu Val Leu Gln Asp Ser Cys
    50                  55                  60

Phe Leu Gln Ile Lys Cys Asp Thr Lys Asp Asp Ser Ile Pro Cys Phe
65                  70                  75                  80

Leu Glu Leu Lys Glu Glu Asp Glu Ile Val Cys Thr Gln His Trp Gln
                85                  90                  95

Asp Ala Val Pro Trp Thr Glu Leu Leu Ser Leu Gln Thr Glu Asp Gly
            100                 105                 110

Phe Trp Lys Leu Thr Pro Glu Leu Gly Leu Ile Leu Asn Leu Asn Thr
        115                 120                 125

Asn Gly Leu His Ser Phe Leu Lys Gln Lys Gly Ile Gln Ser Leu Gly
    130                 135                 140

Val Lys Gly Arg Glu Cys Leu Leu Asp Leu Ile Ala Thr Met Leu Val
145                 150                 155                 160
```

```
Leu Gln Phe Ile Arg Thr Arg Leu Glu Lys Glu Gly Ile Val Phe Lys
                165                 170                 175

Ser Leu Met Lys Met Asp Asp Pro Ser Ile Ser Arg Asn Ile Pro Trp
            180                 185                 190

Ala Phe Glu Ala Ile Lys Gln Ala Ser Glu Trp Val Arg Arg Thr Glu
        195                 200                 205

Gly Gln Tyr Pro Ser Ile Cys Pro Arg Leu Glu Leu Gly Asn Asp Trp
    210                 215                 220

Asp Ser Ala Thr Lys Gln Leu Leu Gly Leu Gln Pro Ile Ser Thr Val
225                 230                 235                 240

Ser Pro Leu His Arg Val Leu His Tyr Ser Gln Gly
                245                 250


<210> SEQ ID NO 43
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43

cgggatccgc cttcagctgg ggctcgctct ggagc                              35


<210> SEQ ID NO 44
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44

cgggaattct tacagaccca cgatgctgtt cag                                33


<210> SEQ ID NO 45
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45

cgggatccgc cttcagctgg ggctcgctct ggagc                              35


<210> SEQ ID NO 46
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46

cgggaattct tactctcggg agggcgggga tc                                 32


<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
```

aaaggatcct atggcagcaa ggc 23

<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
aaagaattct tacagaccca cgatgctgtt 30

<210> SEQ ID NO 49
<211> LENGTH: 80
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
cgggatccgc cttcagctgg ggctcgctgt ggagcggcat taaaaatttc ggttccaccg 60
ttaagaacta tgaattccgg 80

<210> SEQ ID NO 50
<211> LENGTH: 80
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
ccggaattca tagttcttaa cggtggaacc gaaattttta atgccgctcc acagcgagcc 60
ccagctgaag gcggatcccg 80

<210> SEQ ID NO 51
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
cgggattcgg cggcgaattc gatttacgat atcccaacga ccgaa 45

<210> SEQ ID NO 52
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
cccctcgagt tagccttgac tgtaatggag gactctatg 39

<210> SEQ ID NO 53
<211> LENGTH: 51
<212> TYPE: DNA
<213> ORGANISM: Artificial Sequence
<220> FEATURE:
<223> OTHER INFORMATION: Description of Artificial Sequence: Synthetic primer

```
<400> SEQUENCE: 53

ggggccatgg cgctgccgcg cggcaccagg ccgttcttaa cggtggaacc g            51


<210> SEQ ID NO 54
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54

ctctgctagc caccatggcc ttcagctggg gctcg                              35


<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 55

His His His His His His
1               5
```